US011752175B2

(12) United States Patent
Pena et al.

(10) Patent No.: US 11,752,175 B2
(45) Date of Patent: Sep. 12, 2023

(54) COMPOSITIONS AND METHODS FOR GLAUCOMA

(71) Applicants: AUFBAU MEDICAL INNOVATIONS LIMITED, Dublin (IE); CORNELL UNIVERSITY, Ithaca, NY (US)

(72) Inventors: John T. G. Pena, New York, NY (US); James Murray Mitchell, Danville, CA (US); Harmon Lawrence Remmel, New York, NY (US)

(73) Assignee: Cornell University, Ithaca, NY (US)

( * ) Notice: Subject to any disclaimer, the term of this patent is extended or adjusted under 35 U.S.C. 154(b) by 686 days.

(21) Appl. No.: 16/578,320

(22) Filed: Sep. 21, 2019

(65) Prior Publication Data
US 2020/0121724 A1 Apr. 23, 2020

Related U.S. Application Data

(60) Provisional application No. 62/734,699, filed on Sep. 21, 2018.

(51) Int. Cl.
*A61K 35/30* (2015.01)
*C12N 5/079* (2010.01)
*A61K 9/127* (2006.01)

(52) U.S. Cl.
CPC ............ *A61K 35/30* (2013.01); *A61K 9/1271* (2013.01); *C12N 5/0621* (2013.01); *C12N 2509/00* (2013.01); *C12N 2521/00* (2013.01); *C12N 2525/00* (2013.01); *C12N 2527/00* (2013.01)

(58) Field of Classification Search
CPC .............................. A61K 35/30; C12N 5/0621
See application file for complete search history.

(56) References Cited

U.S. PATENT DOCUMENTS

| | | |
|---|---|---|
| 2007/0009497 A1 | 1/2007 | Steinman |
| 2007/0172954 A1 | 7/2007 | Ismagilov |
| 2008/0004657 A1 | 1/2008 | Obermiller |
| 2008/0070324 A1 | 3/2008 | Floyd |
| 2008/0128341 A1 | 6/2008 | Jang |
| 2009/0239792 A1 | 9/2009 | Vaara |
| 2009/0318512 A1 | 12/2009 | Yu |
| 2010/0075315 A1 | 3/2010 | Pieterzkowski |
| 2010/0233706 A1 | 9/2010 | Tuschl |
| 2010/0310642 A1 | 12/2010 | Mitra |
| 2013/0184318 A1 | 7/2013 | Russell |
| 2013/0288375 A1 | 10/2013 | Zhang |
| 2013/0302856 A1 | 11/2013 | Yoo |
| 2014/0038221 A1 | 2/2014 | Bergkvist |
| 2014/0081012 A1 | 3/2014 | Desimone |
| 2014/0220574 A1 | 8/2014 | Tuschl |
| 2014/0257075 A1 | 9/2014 | Kagemann |
| 2014/0349306 A1 | 11/2014 | Chung |
| 2015/0037422 A1 | 2/2015 | Kaplan |
| 2015/0038335 A1 | 2/2015 | Skog |
| 2015/0050328 A1 | 2/2015 | Feinstein |
| 2015/0306236 A1 | 10/2015 | Linder |
| 2016/0040212 A1 | 2/2016 | Aiden |
| 2016/0206780 A1 | 7/2016 | Wang |
| 2016/0245809 A1 | 8/2016 | Connor |
| 2016/0313306 A1 | 10/2016 | Ingber |
| 2017/0051050 A1 | 2/2017 | Pereira Martins |
| 2017/0137469 A1 | 5/2017 | Li |
| 2017/0229043 A1 | 8/2017 | Huh |
| 2017/0258320 A1 | 9/2017 | Abreu |
| 2017/0284975 A1 | 10/2017 | Zhong |
| 2017/0362649 A1 | 12/2017 | Lieberman-Aiden |
| 2018/0085065 A1 | 3/2018 | Haffner |
| 2018/0104186 A1 | 4/2018 | Badiavas |
| 2018/0178142 A1 | 6/2018 | Gjerde |
| 2018/0305682 A1 | 10/2018 | Craighead |
| 2019/0112666 A1 | 4/2019 | Barbie |
| 2019/0216857 A1 | 7/2019 | Pena |

FOREIGN PATENT DOCUMENTS

| | | |
|---|---|---|
| JP | 2016211925 A | 12/2016 |
| RU | 2576778 C1 | 3/2016 |
| WO | 2003102585 A2 | 12/2003 |
| WO | 2009100029 A1 | 8/2009 |
| WO | 2011044216 A1 | 4/2011 |
| WO | 2011090731 A1 | 7/2011 |
| WO | 2011143540 A1 | 11/2011 |
| WO | 2012021891 A1 | 2/2012 |
| WO | 2013016712 A2 | 1/2013 |
| WO | 2013106852 A1 | 7/2013 |
| WO | 2014068408 A2 | 5/2014 |
| WO | 2014159662 A1 | 10/2014 |
| WO | 2014205374 A1 | 12/2014 |
| WO | 2015002975 A1 | 1/2015 |
| WO | 2015080758 A1 | 6/2015 |
| WO | 2015171736 A2 | 11/2015 |
| WO | 2016201064 A1 | 12/2016 |
| WO | 2017087940 A1 | 5/2017 |
| WO | 2017130178 A2 | 8/2017 |
| WO | 2017136430 A1 | 8/2017 |
| WO | 2017190142 A1 | 11/2017 |
| WO | 2018049284 A1 | 3/2018 |

(Continued)

OTHER PUBLICATIONS

Linares et al. High-speed centrifugation induces aggregation of extracellular vesicles 2015. Journal of Extracellular Vesicles 2015, 4 : 29509 (Year: 2015).*

(Continued)

*Primary Examiner* — Taeyoon Kim
*Assistant Examiner* — Alexandra F Connors
(74) *Attorney, Agent, or Firm* — FisherBroyles LLP; Richard R. Eckman; Andrew K. Gonsalves

(57) ABSTRACT

This invention relates to methods and compositions for detecting, identifying and treating glaucoma diseases. More particularly, this invention discloses compositions and methods for affecting intraocular pressure and increasing ocular outflows in glaucoma. Compositions and methods provided include purified and synthesized extracellular vesicle complexes from glaucoma ocular humor for use in methods and devices for detecting, characterizing and treating glaucoma diseases along with active agents. The presence of extracellular vesicle complexes in glaucoma can also be used as a biomarker.

9 Claims, 24 Drawing Sheets

(56) References Cited

FOREIGN PATENT DOCUMENTS

| | | |
|---|---|---|
| WO | 2019109077 A1 | 6/2019 |
| WO | 2019144056 A1 | 7/2019 |

OTHER PUBLICATIONS

Perkumas et al. Myocilin-associated exosomes in human ocular samples Experimental Eye Research 84 (2007) 209-212 (Year: 2007).*
Hoboro et al. An evaluation of fixation methods: Spatial and compositional cellular changes observed by Raman imaging Jul. 2017. Vibrational Spectroscopy 91: 31-45 (Year: 2017).*
Lavik et al. Novel drug delivery systems for glaucoma Eye (2011) 25, 578-586 (Year: 2011).*
Wu et al. Exosomes: Improved methods to characterize their morphology, RNA content, and surface protein biomarkers Analyst. Oct. 7, 2015; 140(19): 6631-6642 (Year: 2015).*
Griffith, Epithelial-mesenchymal transformation during palatal fusion: carboxyfluorescein traces cells at light and electron microscopic levels, Development vol. 116, pp. 1087-1099 (1992).
Dragovic, Sizing and phenotyping of cellular vesicles using Nanoparticle Tracking Analysis, Nanomedicine vol. 7, pp. 780-788 (2011).
Van Der Pol, Recent developments in the nomenclature, presence, isolation, detection and clinical impact of extracellular vesicles, J Thromb Haemost vol. 14, pp. 48-56 (2016).
Suzuki, DNA staining for fluorescence and laser confocal microscopy, J Histochem Cytochem vol. 45, pp. 49-53 (1997).
Thakur, Double-stranded DNA in exosomes: a novel biomarker in cancer detection, Cell Res vol. 24, pp. 766-769 (2014).
Skog, Glioblastoma microvesicles transport RNA and proteins that promote tumour growth and provide diagnostic biomarkers, Nat Cell Biol vol. 10, pp. 1470-1476 (2008).
Mallawaaratchy, Comprehensive proteome profiling of glioblastoma-derived extracellular vesicles identifies markers for more aggressive disease, J. Neurooncol. vol. 131, pp. 233-244 (2017).
Keerthikumar, Proteogenomic analysis reveals exosomes are more oncogenic than ectosomes, Oncotarget vol. 6, pp. 15375-15396 (2015).
Vargas, Neutrophil-derived exosomes: a new mechanism contributing to airway smooth muscle remodeling, Am. J. Respir. Cell and Mol. Biol. vol. 55, pp. 450-461 (2015).
Saari, Photochemistry and stereoselectivity of cellular retinaldehyde-binding protein from bovine retina, J. Biol. Chem. vol. 262, pp. 7618-7622 (1987).
Crabb, Structural and functional characterization of recombinant human cellular retinaldehyde-binding protein, Protein Sci. vol. 7, pp. 746-757 (1998).
Li, Secretory defect and cytotoxicity: the potential disease mechanisms for the retinitis pigmentosa (RP)-associated interphotoreceptor retinoid-binding protein (IRBP), J. Biol. Chem. vol. 288, pp. 11395-11406 (2013).
Den Hollander, A homozygous missense mutation in the IRBP gene (RBP3) associated with autosomal recessive retinitis pigmentosa, Invest. Ophthalmol. Vis. Sci. vol. 50, pp. 1864-1872 (2009).
Friedman, Protein localization in the human eye and genetic screen of opticin, Hum. Mol. Genet. vol. 11, pp. 1333-1342 (2002).
Reardon, Identification in vitreous and molecular cloning of opticin, a novel member of the family of leucine-rich repeat proteins of the extracellular matrix, J. Biol. Chem. vol. 275, pp. 2123-2129 (2000).
Van Pelt-Verkuil, The Use of a Carbodiimide-Containing Fixative for the Immunohistochemical Demonstration of Coagulation Factor VIII in Rat Vascular Tissue, Histochemistry, vol. 71, pp. 187-194 (1981).
Aran, Microfiltration platform for continuous blood plasma protein extraction from whole blood during cardiac surgery, Lab Chip, vol. 11, pp. 2858-2868 (2011).
Thery, Isolation and Characterization of Exosomes from Cell Culture Supernatants and Biological Fluids, Current Protocols in Cell Biology, Supplement 30, vol. 3.22.1-3.22.29, pp. 1-29 (2006).

Bergamaschi, Extracellular matrix signature identifies breast cancer subgroups with different clinical outcome, J. Pathol., vol. 214, pp. 357-367 (2008).
Hollands, Do findings on routine examination identify patients at risk for primary open-angle glaucoma? The rationa clinical examination systematic review, JAMA, vol. 309, pp. 2035-2042 (2013).
Zode, Bone morphogenetic protein 4 inhibits TGF-βstimulation of extracellular matrix proteins in optic nerve head cells: role of gremlin in ECM modulation, Glia, vol. 57, pp. 755-766 (2009).
Ausubul, et al., Informatics for Molecular Biologists, Current Protocols in Molecular Biology, Supplement 33, Unit 19.0.3, pp. 1-2 (1996).
Cox, et al., "MaxQuant Enables High Peptide Identification Rates, Individualized p.p.b.-Range Mass Accuracies and Proteome-Wide Protein Quantification", Nat Biotechnol vol. 26, pp. 1367-1372 (2008).
Debruijn, "Glycogen, Its Chemistry and Morphologic Appearance in the Electron Microscope. I. A Modified $OsO_4$ Fixative Which Selectively Contrasts Glycogen", J Ultrastruct Res, vol. 42, pp. 29-50 (1973).
Fox, Formaldehyde Fixation, J Histochem. Cytochem, vol. 33, pp. 845-853 (1985).
Fraenkel-Conrat, Reaction of Formaldehyde with Proteins, VI. Cross-Linking of Amino Groups with Phenol, Imidazole, and Indole Groups, J Biol. Chem, vol. 174, pp. 827-843 (1948).
Fraenkel-Conrat, et al., The Reaction of Formaldehyde with Proteins, IV. Participation of Indole Groups, J. Biol. Chem. vol. 168, pp. 99-118 (1947).
Ishihama, et al., "Modular Stop and go Extraction Tips with Stacked Disks for Parallel and Multidimensional Peptide Fractionation in Proteomics", J Proteome Res, vol. 5, pp. 988-994 (2006).
Ji, et al., "Proteome Profiling of Exomones Derived from Human Primary and Metastatic Colorectal Cancer Cells Reveal Differential Expression of Key Metastatic Factors and Signal Transduction Components", Proteomics, vol. 13, pp. 1672-1686 (2013).
Jones, "Reactions of Aldehyde with Unsaturated Fatty Acids During Histological Fixation", Histochemical J, vol. 4, pp. 421-465 (1972).
Kunkel, Contact-site cross-linking agents, Mol. Cell. Biochem, vol. 34, pp. 3-13 (1981).
Luga, et al., "Exosomes Mediate Stromal Mobilization of Autocrine Wnt-PCP Signaling in Breast Cancer Cell Migration", Cell, vol. 151, pp. 1542-1556 (2012).
McPhail et al., "Stage at Diagnosis and Early Mortality from Cancer in England", Br J Cancer, vol. 112, pp. S108-S115 (2015).
Renwick, et al., "Multiplexed miRNA Fluorescence in situ Hybridization for Formalin-Fixed Paraffin-Embedded Tissues", Methods Mol Biol, vol. 1211, pp. 171-187 (2014).
Schwanhausser, et al., "Global Quantification of Mammalian Gene Expression Control", Nature vol. 473, pp. 337-342 and Correction vol. 495, pp. 126-127 (2011).
Sung, et al., "Directional Cell Movement Through Tissues Is Controlled by Exosome Secretion", Nat Commun, vol. 6, at 7164, pp. 1-14 (2015).
Torre, et al., "A Global Cancer Incidence and Mortality Rates and Trends—An Update", Cancer Epidemiol Biomarkers & Prevention, vol. 25, pp. 16-27 (2016).
Uniprot C, UniProt: A Hub for Protein Information:, Nucleic Acids Res, vol. 43, pp. D204-D212 (2014).
Venable, et al., "A Simplified Lead Citrate Stain for Use in Electron Microscopy", J Cell Biol, vol. 25, pp. 407-408 (1965).
Voloboueva, et al., "(R)-Alpha-Lipoic Acid Protects Retinal Pigment Epithelial Cells from Oxidative Damage", Invest Ophthalmol Vis Sci, vol. 46, at 4302-4310, pp. 1-24 (2005).
Faivre, In frame fibrillin-1 gene deletion in autosomal dominant Weill-Marchesani syndrome, J. Med. Genet. vol. 40, pp. 34-36 (2003).
Hubmacher, Human eye development is characterized by coordinated expression of fibrillin isoforms, Invest. Ophthalmol. Vis. Sci. vol. 55, pp. 7934-7944 (2014).
Sakuma, Isolation and characterization of the human X-arrestin gene, Gene vol. 224, pp. 87-95 (1998).

(56) References Cited

OTHER PUBLICATIONS

Dryja, Mutations within the rhodopsin gene in patients with autosomal dominant retinitis pigmentosa. N. Eng. J. Med. vol. 323, pp. 1302-1307 (1990).
Liden, Biochemical defects in 11-cis retinol dehydrogenase mutants associated with fundus albipunctatus, J. Biol. Chem. vol. 276, pp. 49251-49257 (2001).
Moiseyev, RPE65 is the isomerohydrolase in the retinoid visual cycle, Proc. Natl. Acad. Sci. vol. 102, pp. 12413-12418 (2005).
Merdes, The 47-kDa lens-specific protein phakinin is a tailless intermediate filament protein and an assembly partner of filensin, J. Cell. Biol. vol. 123, pp. 1507-1516 (1993).
Schindelin, Fiji: an open-source platform for biological-image analysis, Nat. Methods vol. 9, pp. 676-682 (2012).
Schneider, NIH Image to Imaged: 25 years of image analysis, Nat. Methods vol. 9, pp. 671-675 (2012).
Siegel, Cancer Statistics, 2017, CA Cancer J Clin vol. 67, pp. 7-30, (2017).
Luga, Exosomes mediate stromal mobilization of autocrine Wnt-PCP signaling in breast cancer cell migration, Cell vol. 151, pp. 1542-1556, (2012).
Cho, Exosomes from breast cancer cells can convert adipose tissue-derived mesenchymal stem cells into myofibroblast-like cells, Int J Oncol vol. 40, pp. 130-138, (2012).
Lee, Exosomes derived from mesenchymal stem cells suppress angiogenesis by down-regulating VEGF expression in breast cancer cells, PLoS One, vol. 8, pp. e84256 (2013).
Nilsson, Prostate cancer-derived urine exosomes: a novel approach to biomarkers for prostate cancer, Br J Cancer vol. 100, pp. 1603-1607, (2009).
Wysoczynski, Lung cancer secreted microvesicles: underappreciated modulators of microenvironment in expanding tumors, Int J Cancer vol. 125, pp. 1595-1603, (2009).
Janowska-Wieczorek, Microvesicles derived from activated platelets induce metastasis and angiogenesis in lung cancer, Int J Cancer vol. 113, pp. 752-760, (2005).
Silva, Expression and cellular localization of microRNA-29b and RAX, an activator of the RNA-dependent protein kinase (PKR), in the retina of streptozotocin-induced diabetic rats, Mol Vis vol. 17, pp. 2228-2240 (2011).
Wheatley, Immunohistochemical localization of fibrillin in human ocular tissues Relevance to the Marfan syndrome, Arch. Ophthalmol. vol. 113, pp. 103-109 (1996).
Wald, The light reaction in the bleaching of rhodopsin, Science vol. 111, pp. 179-181 (1950).
Dryja, A point mutation of the rhodopsin gene in one form of retinitis pigmentosa, Nature vol. 343, pp. 354-366 (1990).
Yamamoto, Mutations in the gene encoding 11-cis retinol dehydrogenase cause delayed dark adaption and fundus albipunctatus, Nat. Genet. vol. 22, pp. 188-191 (1999).
Carter, Mapping of the human CP49 gene and identification of an intragenic polymorphic marker to allow genetic inkage analysis in autosomal congenital cataract, Biochem. Biophys. Res. Commun. vol. 270, pp. 432-436 (2000).
Rabinowits, Exosomal microRNA: a diagnostic marker for lung cancer, Clin Lung Cancer vol. 10, pp. 42-46, (2009).
Bouremel, A novel 3D printed eye flow resistance model for intraocular pressure after glaucoma surgery: R1, R2 and R3, Investigative Ophthalmology and Visual Sci, vol. 59, pp Abstract Arvo Annual Meeting (2018).
Camras, Advances in glaucoma management: risk factors, diagnostic tools, therapies and the role of prostaglandin analogs, Foreword. Surv Ophthalmol, vol. 53 (Suppl1), pp. S1-S2 (2008.
Stone et al., Missense Variations in the Fibulin 5 Gene and Age-Related Macular Degeneration, N Engl J Med 351, 346-353 (2004).
Shen et al., A Human Opsin-Related Gene That Encodes a Retinaldehyde-Binding Protein, Biochemistry 33, 13117-13125 (1994).

Conde-Vancells, Characterization and Comprehensive Proteome Profiling of Exosomes Secreted by Hepatocytes, J. et al. J Proteome Res 7, 5157-5166 (2008).
Thery, C. et al., Molecular Characterization of Dendritic Cell-derived Exosomes: Selective Accumulation of the Heat Shock Protein hsc73, J Cell Biol 147, 599-610 (1999).
Vlassov, A. et al . . . Exosomes: Current knowledge of their composition, biological functions, and diagnostic and therapeutic potentials, Biochim Biophys Acta 1820, 940-948 (2012).
Higashiyama, S. et al., The Membrane Protein CD9/DRAP 27 Potentiates the Juxtacrine Growth Factor Activity of the Membrane-anchored Heparin-binding EGF-like Growth Factor, J Cell Biol 128, 929-938 (1995).
Keerthikumar, S. et al., ExoCarta: A web-based compendium of exosomal cargo, J Mal Biol 428, 688-692 (2016).
Nickells, Under pressure: cellular and molecular responses during glaucoma, a common neurodegeneration with axonopathy, Annu Rev Neurosci, vol. 35, pp. 153-179 (2012).
Collaborative Normal-Tension Glaucoma Study Group, Comparison of glaucomatous progression between untreated patients with normal-tension glaucoma and patients with therapeutically reduced IOPs, Am J Ophthalmol, vol. 126, pp. 487-497 (1998).
Drance, The Collaborative Normal-Tension Glaucoma Study and some of its lessons, Can J Ophthalmol, vol. 34, pp. 1-6 (1999).
Sommer, Collaborative normal-tension glaucoma study, Am J Ophthalmol, vol. 128, pp. 776-777 (1999).
Dvorak, Tumor Shedding and Coagulation, Science, vol. 212, pp. 923-924 (1981).
Brubaker, Mechanism of action of bimatoprost (Lumigan), Surv Ophthalmol, vol. 45 (Suppl 4), pp. S347-S351 (2001).
Nicoletti, Molecular characterization of the human gene encoding an abundant 61 kDa protein specific to the retinal pigment epithelium, Hum. Mol. Genetic vol. 4, pp. 641-649 (1995).
Morimura et al., Mutations in RGR, encoding a light-sensitive opsin homologue, in patients with retinitis pigmentosa, Nat Genet 23, 393-394 (1999).
Bronner-Fraser, Alterations in neural crest migration by a monoclonal antibody that affects cell adhesion, J Cell Biol vol. 101, pp. 610-617 (1985).
Rowland, The Effects of Crosslinking of Scaffolds Engineered from Cartilage ECM on the Chrondrogenic Differentiation of MSCs, Biomaterials, vol. 34, pp. 5802-5812 (2013).
Lamichhane, Exogenous DNA Loading into Extracellular Vesicles via Electroporation is Size-Dependent and Enables Limited Gene Delivery, Mol Pharm. vol. 12(10), pp. 3650-3657 (2015).
Dismuke, Human aqueous humor exosomes, Exp Eye Res., vol. 132, pp. 73-77 (2015).
Ohno, Focus on Extracellular Vesicles: Development of Extracellular Vesicle-Based Therapeutic Systems, Int J Mol Sci. vol. 17(2), pp. 1-19 (2016).
Tanaka, Profiles of Extracellular miRNAs in the Aqueous Humor of Glaucoma Patients Assessed with a Microarray System, Sci Rep. vol. 4, pp. 5089 (2014).
Lerner, Extracellular vesicles mediate signaling between the aqueous humor producing and draining cells in the ocular system, PloS One, vol. 12(2), pp. e0171153 (2017).
Abu-Hassan, The Trabecular Meshwork: A Basic Review of Form and Function, J Ocul Biol, vol. 2(1), pp. 1-22 (2014).
Burnouf, An overview of plasma fractionation, Annals of Blood, vol. 3, pp. 1-10 (2018).
Zhou, Discovery of a Potential Plasma Protein Biomarker Panel for Acute-on-Chronic Liver Failure Induced by Hepatitis B Virus, Frontiers in Physiology, vol. 8, pp. 1-12 (2017).
Chen, Development and validation of a panel of five proteins as blood biomarkers for early detection of colorectal cancer, Clinical Epidemiology, vol. 9, pp. 517-526 (2017).
Kim, Protein immobilization techniques for microfluidic assays, Biomicrofluidics, vol. 7, pp. 1-47 (2013).
Skubitz, Simultaneous Measurement of 92 Serum Protein Biomarkers for the Development of a Multiprotein Classifier for Ovarian Cancer Detection, Cancer Prev Res, vol. 12, pp. 171-184 (2019).

(56) References Cited

OTHER PUBLICATIONS

Rusling, Measurement of biomarker proteins for point-of-care early detection and monitoring of cancer, analyst, vol. 135, pp. 2496-2511 (2010).
Naba, The matrisome: in silico and in vivo characterization by proteomics of normal and tumor extracellular matrices, Mol. Cell. Proteomics, vol. 11 (M111.014647 ), pp. 1-18 (2012).
Provenzano, Enzymatic targeting of the stroma ablates physical barriers to treatment of pancreatic ductal adenocarcinoma, Cancer Cell, vol. 21, pp. 418-429 (2012).
Barsky, Increased content of type V collagen in desmoplasia of human breast carcinoma, Am. J. Pathol., vol. 108, pp. 276-283 (1982).
Riaz, High TWIST1 mRNA expression is associated with poor prognosis in lymph node-negative and estrogen receptor-positive human breast cancer and is co-expressed with stromal as well as ECM related genes, Breast Cancer Res., vol. 14, pp. 1-15 (2012).
Weinreb, The pathophysiology and treatment of glaucoma: a review, JAMA, vol. 311, pp. 1901-1911 (2014).
Quigley, The number of people with glaucoma worldwide in 2010 and 2020, Br J Ophthalmol, vol. 90, pp. 262-267 (2006).
Zha, Extracellular vesicles: An overview of biogenesis, function, and role in breast cancer, Tumour Biol, vol. 39, pp. 1-7 (2017).
Stradleigh, Fixation strategies for retinal immunohistochemistry, Progress in retinal and eye research, vol. 48, pp. 181-202 (2015).
Anand, "Mechanism of Corneal Permeation of L-valyl Ester of Acyclovir: Targeting the Oligopeptide Transporter on the Rabbit Cornea", Pharm Res, vol. 19, pp. 1194-1202 (2002).
Anand, "Amino Acid Prodrugs of Acyclovir as Possible Antiviral Agents against Ocular HSV-1 Infections: Interactions with the Neutral and Cationic Amino Acid Transporter on the Corneal Epithelium", Curr Eye Res, vol. 29, pp. 153-166 (2004).
Dalpiaz, et al., "Molecular Mechanism Involved in the Transport of a Prodrug Dopamine Glycosyl Conjugate", Int J Pharm., vol. 336, pp. 133-139 (2007).
Dun, et al., "Functional and Molecular Analysis of D-serine Transport in Retinal Muller Cells", Exp Eye Res., vol. 84, pp. 191-199 (2007).
Gunda, et al., "Corneal Absorption and Anterior Chamber Pharmacokinetics of Dipeptide Monoester Prodrugs of Ganciclovir (GCV): In vivo Comparative Evaluation of these Prodrugs with Val-GCV and GCV in Rabbits", J Ocul Pharmacol and Ther, vol. 22, pp. 465-476 (2006).
Janoria, et al., "Vitreal Pharmacokinetics of Biotinylated Ganciclovir: Role of Sodium-dependent Multibitamin Transporter Expressed on Retina", J Ocul Pharmacol and Ther, vol. 25, pp. 39-49 (2009).
Kaiser, et al., "RNAi-based treatment for neovascular age-related macular degeneration by SiRNA-027", Am J Ophthalmol., vol. 150, pp. 33-39 (2010).
Kansara, et al., "Dipeptide Monoester Ganciclovir Prodrugs for Transscleral Drug Delivery: Targeting the Dligopeptide Transporter on Rabbit Retina", J Ocul Pharmacol and Ther., vol. 23, pp. 321-334 (2007).
Katragadda, et al., "Modulation of P-glycoprotein-mediated Efflux by Prodrug Derivatization: an Approach Involving Peptide Transporter-mediated Influx across Rabbit Cornea", J Ocul Pharmacol and Ther., vol. 22, pp. 110-120 (2006).
Kim, et al., "Genome Surgery Using Cas9 Ribonucleoproteins for the Treatment of Age-Related Macular Degeneration", Genome Research, vol. 27, pp. 419-426 (2017).
Liu, et al., "Gene Therapy for Ocular Diseases", Postgrad. Med. J., vol. 87, at 487-495 pp. 1-16 (2011).
Majumdar, et al., "Dipeptide Monoester Ganciclovir Prodrugs for Treating HSV-1-induced Corneal Epithelial and Stromal Keratitis: In vitro and In vivo Evaluations", J Ocul Pharmacol and Ther., vol. 21, pp. 463-474 (2005).
Majumdar, et al., "Transcorneal Permeation of L- and D-aspartate Ester Prodrugs of Acyclovir: Delineation of Passive Diffusion Versus Transporter involvement", Pharm Res., vol. 26, pp. 1261-1269 (2009).

Malecaze, et al., "Detection of Vascular Endothelial Growth Factor Messenger RNA and Vascular Endothelial Growth Factor-like Activity in Proliferative Diabetic Retinopathy", Arch Ophthalmol, vol. 112, pp. 1476-1482 (1994).
Nguyen, et al., "Dose-ranging evaluation of intravitreal siRNA PF-04523655 for diabetic macular edema (the DEGAS Study)", Invest Ophthalmol & Vis Sci., vol. 53, pp. 7666-7674 (2012).
Nguyen, et al., "Phase 1 dose-escalation study of a siRNA targeting the RTP801 gene in age-related macular degeneration patients", Eye (Lend), vol. 26, pp. 1099-1105 (2012).
O'Reilly, et al., "RNA interference-mediated suppression and replacement of human rhodopsin in vivo", Am J Hum Genet., vol. 81, pp. 127-135 (2007).
Rosca, et al., "Anti-angiogenic Peptides for Cancer Therapeutics", Curr. Pharm. Biotechol., vol. 12, at 1101-1116 pp. 1-31 (2011).
Tyanova, et al., "The Perseus Computational Platform for Comprehensive Analysis of (Prote)omics Data", Nat Methods, vol. 13, pp. 731-740 (2016).
Zhu, et al., "Gene and Mutation Independent Therapy via CRISPR-Cas9 Mediated Cellular Reprogramming in Rod Photoreceptors", Cell Res., vol. 27, pp. 830-833 (2017).
Trams, Exfoliation of membrane ecto-enzymes in the form of micro-vesicles, Biochim Biophys Acta vol. 645, pp. 63-70 (1981).
Consortium, EV-Track: transparent reporting and centralizing knowledge in extracellular vesicle research, Nat Methods vol. 14, pp. 228-232 (2017).
Brodeur, Neuroblastoma: Biological Insights Into A Clinical Enigma, Nature Reviews, vol. 3, pp. 203-216 (2003).
Drolet, Fit for the Eye: Aptamers in Ocular Disorders, Nucleic Acid Therapeutics, vol. 26, pp. 127-146 (2016).
Guzman-Aranguez, Small-interfering RNAs (siRNAs) as a Promising Tool for Ocular Therapy, British Journal of Pharmacology, vol. 170, pp. 730-747 (2013).
Harris, American Society of Clinical Oncology 2007 Update of Recommendations for the Use of Tumor Markers in Breast Cancer, Journal of Clinical Oncology, vol. 25, pp. 5287-5312 (2007).
Ito, Formaldehyde-Glutaraldehyde Fixatives Containing Trinitro Compounds, The Journal of Cell Biology, Abstract 418, vol. 39, pp. 168a-169a (1968).
Valadi, Exosome-mediated transfer of mRNAs and microRNAs is a novel mechanism of genetic exchange between cells, Nat Cell Biol vol. 9, pp. 654-659 and S1-S11 (2007).
Peinado, The secreted factors responsible for pre-metastatic niche formation: Old sayings and new thoughts, Semin Cancer Biol vol. 21, pp. 139-146 (2011).
Pulaski, Mouse 4T1 breast tumor model, Curr Protoc Immunol Chapter 20, Unit 20 22 (2001).
Ji, Proteome profiling of exosomes derived from human primary and metastatic colorectal cancer cells reveal differential expression of key metastatic factors and signal transduction components, Proteomics vol. 13, pp. 1672-1686 (2013).
Koppen, Proteomics analyses of microvesicles released by *Drosophila* Kc167 and S2 cells, Proteomics vol. 11, pp. 4397-4410 (2011).
Baietti, Syndecan-syntenin-ALIX regulates the biogenesis of exosomes, Nat. Cell Biol. vol. 14, pp. 677-685 and S1-S18 (2012).
Kim, Proteomic analysis of microvesicles derived from human mesenchymal stem cells, J. Proteome Res. vol. 11, pp. 839-849 (2012).
Inui, Annexin VI binds to a synaptic vesicle protein, synapsin I, J. Neurochem. vol. 63, pp. 1917-1923 (1994).
Wolfers, Tumor-derived exosomes are a source of shared tumor rejection antigens for CTL cross-priming, Nature Med. vol. 7, pp. 297-303 (2001).
Maw, Mutation of the gene encoding cellular retinaldehyde binding protein in autosomal recessive retinitis pigmentosa, Nat. Genet. vol. 17, pp. 198-200 (1997).
Weidle, The Emerging Role of New Protein Scaffold-based Agents for the Treatment of Cancer, Cancer Genomics & Proteomics, vol. 10, pp. 155-168 (2013).
Klingeborn, Roles of Exosomes in the Normal and Diseased Eye, Progress in Retinal and Eye Research, vol. 59, pp. 158-177 (2017).

(56) References Cited

OTHER PUBLICATIONS

Keller, The Juxtacanalicular Region of Ocular Trabecular Meshwork: A Tissue with a Unique Extracellular Matrix and Specialized Function, J Ocular Biology, vol. 1, pp. 1-15 (2013).
Gyorgy, Membrane vesicles, current state-of-the-art: emerging role of extracellular vesicles. Cell Mol Life Sci vol. 68, pp. 2667-2688 (2011).
Zhang, Identification of distinct nanoparticles and subsets of extracellular vesicles by asymmetric flow field-flow fractionation, Nat Cell Biol vol. 20, pp. 332-343 (2018).
Hristov, Apoptotic bodies from endothelial cells enhance the number and initiate the differentiation of human endothelial progenitor cells in vitro, Blood vol. 104, pp. 2761-2766 (2004).
Raposo, Extracellular vesicles: exosomes, microvesicles, and friends. J Cell Biol vol. 200, pp. 373-383 (2013).
Gatti, Microvesicles derived from human adult mesenchymal stem cells protect against ischaemia-reperfusion-induced acute and chronic kidney injury, Nephrol Dial Transplant vol. 26, pp. 1474-1483 (2011).
Zomer, In Vivo imaging reveals extracellular vesicle-mediated phenocopying of metastatic behavior, Cell vol. 161, pp. 1046-1057 (2015).
Becker, Extracellular Vesicles in Cancer: Cell-to-Cell Mediators of Metastasis, Cancer Cell vol. 30, pp. 836-848 (2016).
Zappulli, Extracellular vesicles and intercellular communication within the nervous system, J Clin Invest vol. 126, pp. 1198-1207 (2016).
D'Souza-Schorey, Tumor-derived microvesicles: shedding light on novel microenvironment modulators and prospective cancer biomarkers, Genes Dev vol. 26, pp. 1287-1299 (2012).
Bellingham, Exosomes: vehicles for the transfer of toxic proteins associated with neurodegenerative diseases? Front Physiol vol. 3, article 124, pp. 1-12 (2012).
Lai, Visualization and tracking of tumour extracellular vesicle delivery and RNA translation using multiplexed reporters, Nat Commun vol. 6, pp. 7029 (2015).
Ridder, Extracellular vesicle-mediated transfer of functional RNA in the tumor microenvironment, Oncoimmunology vol. 4, pp. e1008371 (2015).
Tkach, Communication by Extracellular Vesicles: Where We Are and Where We Need to Go, Cell vol. 164, pp. 1226-1232(2016).
Le Goff, Adult vitreous structure and postnatal changes, Eye (Lond) vol. 22, pp. 1214-1222 (2008).
Ragusa, miRNA profiling in vitreous humor, vitreal exosomes and serum from uveal melanoma patients: Pathological and diagnostic implications, Cancer Biol Ther vol. 16, pp. 1387-1396 (2015).
Shi, Antigen retrieval in formalin-fixed, paraffin-embedded tissues: an enhancement method for immunohistochemical staining based on microwave oven heating of tissue sections, J Histochem Cytochem vol. 39, pp. 741-748 (1991).
Ikeda, Extraction and analysis of diagnostically useful proteins from formalin-fixed, paraffin-embedded tissue sections, J Histochem Cytochem vol. 46, pp. 397-403 (1998).
Pena, miRNA in situ hybridization in formaldehyde and EDC-fixed tissues, Nat Methods vol. 6, pp. 139-141 (2009).
Raposo, B lymphocytes secrete antigen-presenting vesicles, J Exp Med vol. 183, pp. 1161-1172 (1996).
Batrakova, Using exosomes, naturally-equipped nanocarriers, for drug delivery, 2015, J Control Release, vol. 219, pp. 396-405.
Narumi, A survey of vitreous cell components performed using liquid-based cytology, Acta Ophthalmol, 2015, vol. 93 pp. e386-e390.
Wu, Exosomes: Improved methods to characterize their morphology, RNA content, and surface protein biomarkers, Analyst, 2015, vol. 140, pp. 6631-6642.
Hoffman, Regulation of Myocilin-Associated Exosome Release from Human Trabecular Meshwork Cells, Investigative Ophthalmology & Visual Science, 2009, vol. 50, pp. 1313-1318.
Stamer, Protein Profile of Exosomes from Trabecular Meshwork Cells, J Proteomics, 2011, vol. 74, pp. 796-804.
Renwick, Multicolor microRNA FISH effectively differentiates tumor types, J Clin. Invest., vol. 123 (6), pp. 2694-2702, 2013.
Hauser, Apoptotic Bodies: Selective Detection in Extracellular Vesicles, Signal Transduction Immunohistochemistry, Chapter 12, pp. 193-199, Oct. 2, 2017.

\* cited by examiner

COMPOSITIONS AND METHODS FOR GLAUCOMA

BACKGROUND

Glaucoma diseases are a world-wide leading cause of vision loss and affect an estimated 70 million people. Glaucoma is a permanently blinding disease that is asymptomatic until patients experience advanced vision loss. Diagnosis of glaucoma is often delayed.

Forms of glaucoma are described as open angle glaucoma or closed angle glaucoma. Primary open-angle glaucoma (POAG) is most prevalent, about 75% of cases. Narrow angle glaucoma and other less common forms account for the other 25%. In POAG, the anterior chamber angle appears healthy and open and there is elevated intraocular pressure (IOP) with no underlying disease.

Risk factors for POAG include elevated IOP, advancing age, family history, African ancestry, myopia, and associations with diabetes or hypertension. The pathophysiology responsible for glaucoma is related to increased resistance to aqueous outflow, but the direct mediator of this process remains unknown. The etiology of glaucoma is poorly understood and the factors contributing to its progression have not been identified.

Signs and symptoms of glaucoma include damage to the optic nerve, with degeneration of retinal ganglion cells, changes to the optic nerve head, and corresponding visual field loss. Elevation of IOP is related to retinal ganglion cell (RGC) death and ultimately visual field (VF) loss. IOP-related optic nerve damage is important in the pathogenesis of POAG. Patients with POAG and ocular hypertension (OHT) have elevated IOP. Raised IOP is a significant risk factor for the progression from OHT to POAG. Raised IOP is the only common clinical finding in a wide variety of secondary glaucomas. Reduction of IOP was shown to lower the risk of progression in NTG. In animal models, raised IOP precedes glaucomatous nerve damage. In general, the etiology of elevated IOP may be due to reduced aqueous outflow.

Pharmaceutical treatment of glaucoma is directed to lowering IOP which may slow disease progression in some patients. Drawbacks of current treatments include lack of efficacy and side effects of medications.

What is needed are effective methods and compositions for glaucoma, as well as modalities for lowering IOP and improving ocular outflows.

There is an urgent need for methods, kits, and compositions for detecting, identifying and treating glaucoma.

BRIEF SUMMARY

This invention relates to methods and compositions for detecting, identifying and treating glaucoma diseases. More particularly, this invention discloses compositions and methods for affecting intraocular pressure and increasing ocular outflows in glaucoma.

This invention provides methods, compositions, devices, kits and reagents for detecting, identifying and treating glaucoma diseases.

In some aspects, this invention provides methods and compositions for reducing intraocular pressure and increasing ocular outflows in glaucoma subjects. Aspects of this invention can reduce formation and presence of aggregational features and structures in ocular humor.

In further aspects, this disclosure provides therapeutic compositions for glaucoma.

Embodiments of this invention provide devices for measuring and characterizing glaucoma aggregational features, as well as intraocular pressure and ocular outflows.

Additional aspects of this disclosure include diagnostic and screening modalities for glaucoma. Further embodiments include kits and reagents for carrying out the foregoing.

Embodiments of this invention include the following:

A composition, comprising purified extracellular vesicle complexes from glaucoma ocular humor. The composition can be purified from animal or clinical sources. The extracellular vesicle complexes can be aggregates of extracellular vesicles. The extracellular vesicle complexes can be aggregates of at least 10 extracellular vesicles.

In some embodiment, the extracellular vesicles may be exomeres, exosomes, multivesicular bodies, intraluminal vesicles (ILVs), multivesicular endosomes (MVEs), oncosomes, micro-vesicles, apoptotic bodies, or vesicles originating from endosome or plasma membranes.

In further embodiments, the aggregates may be composed of extracellular vesicles, wherein the aggregates may have a diameter from about 360 to about 21,000 nanometers, or from 360 to 10,000 nanometers, or from 360 to 5,000 nanometers, or from 360 to 3,000 nanometers, or from 360 to 1,000 nanometers. In certain embodiments, the aggregates may be composed of extracellular vesicles, and at least 50% of the aggregates have a diameter from 360 to 21,000 nanometers.

A composition, comprising purified extracellular vesicle complexes from glaucoma ocular humor, wherein the extracellular vesicle complexes are cross linked. Cross linking can be done by contacting the extracellular vesicle complexes with a cross linking compound. Extracellular vesicle complexes that are cross linked can be reversibly cross linked, or non-reversibly cross linked.

A composition, comprising purified extracellular vesicle complexes from glaucoma ocular humor, wherein the extracellular vesicle complexes are stabilized by a fixative. Extracellular vesicle complexes may be stabilized by contacting with a fixative.

A composition, comprising purified extracellular vesicle complexes from glaucoma ocular humor, wherein the extracellular vesicle complexes are prepared by ultracentrifugation. The purified extracellular vesicle complexes may be re-suspended in buffered saline.

A composition, comprising purified extracellular vesicle complexes from glaucoma ocular humor, further comprising a drug delivery excipient.

This invention further contemplates a composition comprising synthesized extracellular vesicle complexes. The composition can be synthesized from animal or clinical sources. The extracellular vesicle complexes can be aggregates of extracellular vesicles. The extracellular vesicle complexes may be aggregates of at least 10 extracellular vesicles. The aggregates can be composed of extracellular vesicles, and can have a diameter from 360 to 3,000 nanometers. The extracellular vesicles may be exomeres, exosomes, multivesicular bodies, intraluminal vesicles (ILVs), multivesicular endosomes (MVEs), oncosomes, or micro-vesicles. The composition may further comprise a cross linking compound or agent, a fixative, or a drug delivery excipient.

In additional embodiments, this disclosure includes compounds made by the method comprising purifying extracellular vesicle complexes from glaucoma ocular humor.

The composition may be purified from animal or clinical sources, by a step of centrifugation, differential centrifugation, density gradient centrifugation, or ultracentrifugation, or by a step of precipitation with a precipitation reagent selected from polymeric precipitation reagents, protamine, sodium acetate, and organic solvents, or by a step of immunoaffinity capture of extracellular vesicle complexes, or by a step of microfluidic separation or sequential filtration of extracellular vesicle complexes.

The extracellular vesicle complexes can be composed of extracellular vesicles, the complexes having a diameter from 360 to 21,000 nanometers, or from 360 to 3,000 nanometers. The extracellular vesicles may be exomeres, exosomes, multivesicular bodies, intraluminal vesicles (ILVs), multivesicular endosomes (MVEs), oncosomes, micro-vesicles, apoptotic bodies, or vesicles originating from endosome or plasma membranes.

A compound made by the method comprising purifying extracellular vesicle complexes from glaucoma ocular humor. The composition can be purified from animal or clinical sources. The method may further comprise a step of centrifugation, differential centrifugation, density gradient centrifugation, or ultracentrifugation. The method may further comprise a step of precipitation with a precipitation reagent selected from polymeric precipitation reagents, protamine, sodium acetate, and organic solvents. The method may further comprise a step of immunoaffinity capture of extracellular vesicle complexes. The method may further comprise a step of microfluidic separation or sequential filtration of extracellular vesicle complexes. The extracellular vesicle complexes can be composed of extracellular vesicles, and can have a diameter from 360 to 21,000 nanometers, or from 360 to 3,000 nanometers. The extracellular vesicles may be exomeres, exosomes, multivesicular bodies, intraluminal vesicles (ILVs), multivesicular endosomes (MVEs), oncosomes, micro-vesicles, apoptotic bodies, or vesicles originating from endosome or plasma membranes.

In further embodiments, the purified extracellular vesicle complexes from glaucoma ocular humor may be cross linked.

Embodiments of this invention further provide treating a glaucoma disease. A glaucoma disease may be treated by administering a surface active agent for affecting EV-complexes. A surface active agent can be used for ameliorating at least one symptom or condition of a glaucoma disorder.

Additional embodiments of this disclosure can provide devices for measuring pressure and flow rate of a fluid composition, comprising: a channel having an inlet at a first end and an outlet at a second end, wherein the inlet and outlet are in fluid communication; a meshwork composition lodged in the channel for providing resistance to flow, wherein the meshwork composition comprises any one or more or all of: a uveal meshwork; a corneoscleral meshwork; and a juxtacanalicular meshwork; a fluid reservoir for holding the fluid composition, wherein the fluid reservoir is in fluid communication with the inlet of the channel for introducing the fluid composition into the inlet of the channel; a pressure source for applying pressure to the fluid composition in the fluid reservoir for introducing the fluid composition into the inlet of the channel; a flow sensor in fluid communication with the fluid composition for measuring the flow rate and pressure of the fluid composition at the inlet of the channel and transmitting the flow rate and pressure to a processor; and a processor for receiving and displaying the flow rate and pressure.

In some embodiments, the channel may be a microfluidic channel. The channel can be within a microfluidic chip. The meshwork composition can comprise glass beads, magnetic beads, gel particles, dextran particles, or polymer particles. The meshwork composition may comprise glass fibers, polymeric fibers, inorganic fibers, or metal fibers. The uveal meshwork can comprise fenestrations of about 25 micrometers. The corneoscleral meshwork can comprise fenestrations of about 2-15 micrometers. The juxtacanalicular meshwork may comprise fenestrations of about 1 to 4 micrometers or less.

In additional embodiments, the device may further comprise one or more detectors for analyzing the fluid composition within the channel or exiting the outlet of the channel. The meshwork composition may comprise an anterior half of an animal eye with lens, wherein the TM of the eye is oriented in between the inlet and the outlet of the channel. The meshwork composition can comprise a purified or synthetic compound or composition as described above.

In additional embodiments, a device may comprise one or more of the purified or synthetic compositions described above, including a composition containing purified extracellular vesicle complexes from glaucoma ocular humor. A device of this disclosure can include a meshwork composition lodged in the channel for providing resistance to flow, wherein the meshwork composition comprises any one or more or all of: a uveal meshwork; a corneoscleral meshwork; and a juxtacanalicular meshwork; wherein at least a portion of a meshwork can be composed of purified extracellular vesicle complexes from glaucoma ocular humor. In further embodiments, a device of this invention can include a meshwork composed of purified extracellular vesicle complexes from glaucoma ocular humor, wherein the device can be used for test samples for diagnosis, monitoring or prognosis of subjects for glaucoma, or for detecting the effects of various compounds, compositions or drugs on the stability of purified extracellular vesicle complexes from glaucoma ocular humor.

This invention can further provide a composition for reducing extracellular vesicle complexes in glaucoma ocular humor, wherein the extracellular vesicle complexes are aggregates composed of extracellular vesicles, and can have a diameter from 360 to 21,000 nanometers, the composition comprising a carrier and one or more active agents.

A composition above may further comprise one or more of a solubilizing agent, a surfactant, a phospholipid, a thickener, a tonicifier tonicity adjusting agent, and a preservative. The composition may be for use in reducing intraocular pressure in glaucoma, or for use in increasing ocular outflows in glaucoma.

A composition above may further comprise one or more active agents that have been modified for delivery or metabolic acceptability, or have been PEGylated with a polyethylene glycol or polypropylene glycol chain.

In further aspects, this disclosure provides methods for increasing ocular outflows in a subject in need, the method comprising administering a composition described above. The method may further comprise providing an aqueous humor sample from the subject after the administration; measuring a quantity of glaucoma extracellular vesicle complexes in the sample; and re-administering the composition based on the quantity exceeding a reference value. The quantity can include one or more of the number, size, density, morphology, and spatial distribution of the extracellular vesicle complexes. The reference value can be a quantity of glaucoma extracellular vesicle complexes in a reference population of healthy individuals.

In additional aspects, this disclosure provides methods for reducing intraocular pressure in a subject in need, the methods comprising administering a composition as described above.

The method can further comprise providing an aqueous humor sample from the subject after the administration; measuring a quantity of glaucoma extracellular vesicle complexes in the sample; and re-administering the composition based on the quantity exceeding a reference value. The quantity can include one or more of the number, size, density, morphology, and spatial distribution of the extracellular vesicle complexes. The reference value can be a quantity of glaucoma extracellular vesicle complexes in a reference population of healthy individuals.

Also contemplated in this invention are methods for treating glaucoma in a subject in need, the methods comprising administering a composition as described above.

The methods may further comprise providing an aqueous humor sample from the subject after the administration; measuring a quantity of glaucoma extracellular vesicle complexes in the sample; and administering or re-administering the composition based on the quantity exceeding a reference value. The quantity can include one or more of the number, size, density, morphology, and spatial distribution of the extracellular vesicle complexes. The reference value is a quantity of glaucoma extracellular vesicle complexes in a reference population of healthy individuals.

Additional aspects include methods for treating glaucoma in a subject in need, the methods comprising: obtaining an aqueous humor sample from the subject; analyzing the sample for a quantity of glaucoma extracellular vesicle complexes; administering a glaucoma active agent to the subject based on the quantity exceeding a reference value. The quantity can include one or more of the number, size, density, morphology, and spatial distribution of the extracellular vesicle complexes. The reference value may be a quantity of glaucoma extracellular vesicle complexes in a reference population of healthy individuals. The glaucoma extracellular vesicle complexes can be aggregates of extracellular vesicles, or may be extracellular vesicles having a diameter greater than 300 nanometers.

In certain embodiments, this invention provides methods for identifying glaucoma or pre-glaucoma in a subject, the methods comprising: obtaining an aqueous humor sample from the subject; analyzing the sample for a quantity of glaucoma extracellular vesicle complexes; identifying the subject as having glaucoma or pre-glaucoma based on the quantity exceeding a reference value. The quantity can include one or more of the number, size, density, morphology, and spatial distribution of the extracellular vesicle complexes. The reference value may be a quantity of glaucoma extracellular vesicle complexes in a reference population of healthy individuals. The glaucoma extracellular vesicle complexes can be aggregates of extracellular vesicles or are extracellular vesicles having a diameter greater than 300 nanometers.

The methods for identifying glaucoma or pre-glaucoma in a subject may further comprise contacting the sample with a fixative, a non-reversible cross-linking compound or agent, and an aldehyde-containing fixative. The non-reversible cross-linking agent can be selected from a water-soluble carbodiimide, cyanogen halide, and mixtures thereof. The non-reversible cross-linking agent can be selected from 1-ethyl-3-(3-dimethylaminopropyl)-carbodiimide, cyanogen bromide, cyanogen fluoride, cyanogen chloride, and cyanogen iodide.

The methods may further comprise contacting the sample with an additional cross-linking agent.

The analyzing can comprise imaging selected from microscopy, color metric assay, chemiluminescence assay, spectrophotometry, positron emission tomography, computerized tomography, and magnetic resonance imaging.

Further embodiments include kits for detecting glaucoma or pre-glaucoma, the kits comprising reagents for detecting glaucoma aqueous humor extracellular vesicle complexes in an isolate sample.

BRIEF DESCRIPTION OF THE DRAWINGS

(FIG. 12) Representative transmission electron microscopy photographs show human aqueous humor collected from a patient with POAG and no treatment (placebo, control, buffered saline) shows evidence of glaucoma associated-EV-complexes. Images show large electron dense glaucoma associated-EV-complexes in all panels. The placebo treatment had no effect the glaucoma associated-EV-complexes. Scale bars are marked on the figures.

(FIG. 13) Representative photographs show POAG aqueous humor from Subject #2 samples treated with bimatoprost show a disruption of the large electron dense glaucoma-associated-EV-aggregates. The glaucoma-associated-EV-aggregates were smaller in size, when compared to the controls (shown in FIG. 12). On high power imaging, we do not observe many aggregated EVs. Scale bars are marked on the figures.

DETAILED DESCRIPTION OF THE INVENTION

This invention provides methods, compositions, devices, kits and reagents for detecting, identifying and treating glaucoma disease. Embodiments of this invention utilize ultrastructural features of ocular aqueous humor as guides and markers for glaucoma therapeutic modalities.

In some aspects, this invention provides methods and compositions for reducing intraocular pressure and increasing ocular outflows in glaucoma subjects. Aspects of this invention can reduce formation and presence of aggregational features and structures in ocular humor.

In further aspects, this disclosure provides therapeutic compositions for glaucoma.

Embodiments of this invention provide devices for measuring and characterizing glaucoma aggregational features, as well as intraocular pressure and ocular outflows.

Additional aspects of this disclosure include diagnostic and screening modalities for glaucoma. Further embodiments include kits and reagents for carrying out the foregoing.

Embodiments of this invention can provide glaucoma diagnosis based on a unique and reliable ultrastructural biomarker herein identified. The ultrastructural component can block the trabecular meshwork, increasing IOP and, over time, ocular aqueous outflow resistance increases leading to elevated intraocular pressure, and eventual vision loss. The ultrastructural component in the humor fluid of a patient with POAG can be reflected in EV aggregates formed together in large EV-complexes. The EV-complexes can be multiple microns in size and are glaucoma-associated-EV-complexes. The EV-complexes may be present in glaucoma patient samples and sizeable enough to block the trabecular meshwork.

Embodiments of this invention can provide compositions and methods for purifying and/or synthesizing EV-complexes of this ultrastructural component for use in therapeutic and biological methods.

Embodiments of this invention can provide compositions and methods for therapeutics and treatment of POAG and testing POAG aqueous humor specimens.

In some embodiments, glaucoma-associated-EV-complexes can be reduced by dissociation and other routes.

In additional embodiments, compositions and methods of this invention can reduce intraocular pressure and/or increase ocular outflows.

Embodiments of this invention further contemplate methods for treating glaucoma.

In certain aspects, a glaucoma disease may be treated by administering a surface active agent for affecting EV-complexes. A surface active agent may be used for ameliorating, alleviating, inhibiting, lessening, delaying, and/or preventing at least one symptom or condition of a glaucoma disorder.

Figure 1:
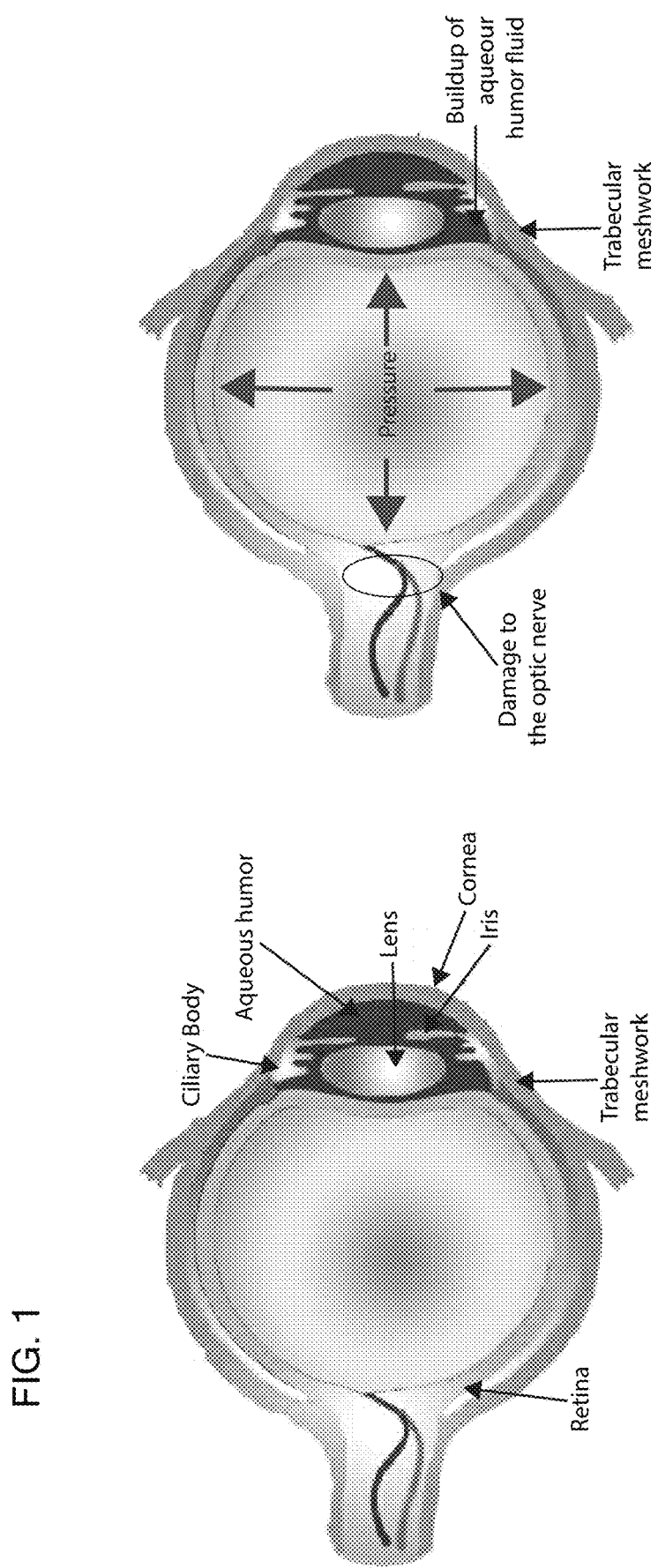
FIG. 1 shows an illustration of normal eye (left) anatomy compared to glaucomatous eye (right).
Figure 2:
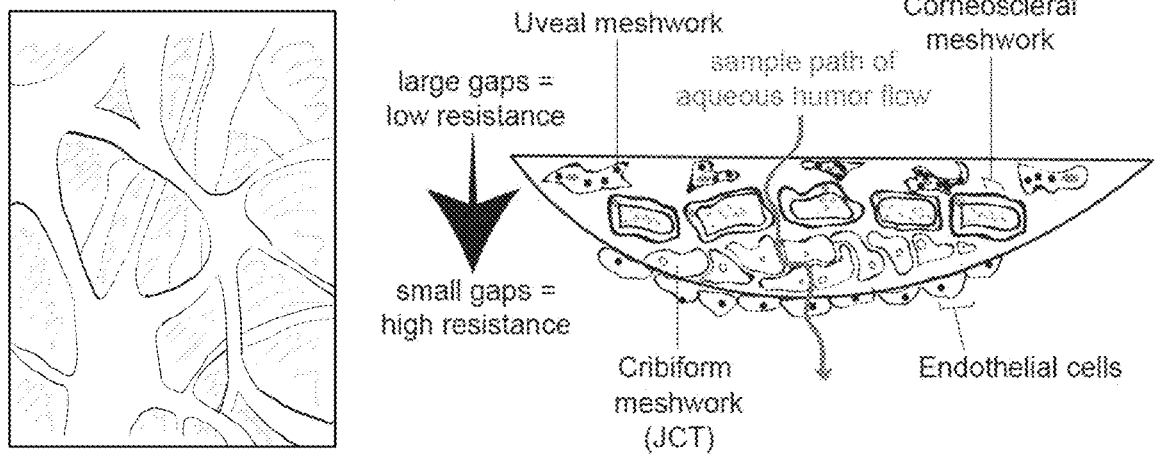
FIG. 2 shows an electron micrograph of a sample of trabecular meshwork (left), and an illustration of aqueous humor flow in eye trabecular meshwork (right).

The eye can be viewed as a closed chamber. (FIG. 1, left) IOP can be determined by the rate of aqueous humor formation and the rate fluid exit. (FIG. 1, right) In general, reduced aqueous outflow in glaucoma can be related to raised IOP. Aqueous humor outflow can be related to elevated IOP and glaucomatous visual damage. Aqueous humor exits the eye via two pathways: the trabecular meshwork and to a lesser extent the uveolscleral outflow. (FIG. 2)

Abnormal aqueous humor outflow can cause elevated IOP. The trabecular meshwork (TM) can be a major site of outflow. The TM is a filter-like tissue composed of a series of fenestrated striations that allow aqueous humor to flow and exit the anterior chamber via Schlemm's canal. The primary function of the TM is to allow aqueous humor to exit the eye and establish IOP.

The juxtacanalicular tissue (JCT) or cribriform region is next to Schlemm's canal and is the region of the TM that may be implicated in establishing IOP. The site of most resistance to the aqueous outflow can be the JCT tissue, which measures approximately 2-20 µm. JCT is composed of the loosely arranged extracellular matrix (ECM) into which cells are embedded.

Abnormal regulation of aqueous flow through the TM may be associated with elevated IOP. The ECM of the TM can be a barrier that may isolate the ocular fluid outflow.

Ultrastructural features or compositions in the aqueous humor of patients with glaucoma that are physically larger than the fenestrations of the JCT outlet, or that of other TM tissues, can block the TM.

Ultrastructural features or compositions in the aqueous humor can include structures based on extracellular vesicles (EV). EVs are transport nano-vesicles related to intercellular communication via transfer of biomolecules such as proteins, lipids, and nucleic acids from one cell to another.

In general, various cell types secrete EVs into fluids like blood, cerebrospinal fluid, and urine. Examples include exomeres approximately 35 nm, exosomes about 40-100 nm, larger micro-vesicles about 100-1000 nm, and apoptotic bodies about 1-5 µm. EVs can be associated with pathophysiology of disease.

In some embodiments of this invention, ultrastructural features and compositions based on EVs are utilized in characterizing ocular fluids.

In further embodiments, ultrastructural features and compositions based on EVs can be utilized in devices for determining IOP. Ultrastructural features and compositions based on EVs can be monitored for determining therapeutic effects in reducing IOP. Ultrastructural features and compositions based on EVs can be monitored as biomarkers for determining therapeutic effects in reducing TOP.

In additional embodiments, ultrastructural features and compositions based on EVs can be utilized in devices for measuring ocular outflows. Ultrastructural features and compositions based on EVs can be monitored for determining therapeutic effects in increasing ocular outflows. Ultrastructural features and compositions based on EVs can be monitored as biomarkers for determining therapeutic effects in increasing ocular outflows.

In further embodiments, ultrastructural features and compositions based on EVs are utilized in reducing formation and presence of aggregational features, structures and particles in ocular humor.

In certain embodiments, ultrastructural features and compositions based on EVs are utilized in devices for detecting ocular conditions and parameters.

In additional embodiments, ultrastructural features and compositions based on EVs are utilized in identifying glaucoma in a subject.

In further embodiments, ultrastructural features and compositions based on EVs are utilized in methods, kits and reagents for glaucoma.

Without wishing to be bound by any particular theory, ultrastructural features and compositions based on EVs in glaucoma may have larger structures that block the TM and/or other outflows.

Glaucoma disorders, referred to herein as "glaucoma," that can be treated with the methods and compositions as described herein include, but are not limited to, preglaucoma open angle with borderline findings, open angle, low risk, anatomical narrow angle primary angle closure suspect, steroid responder, ocular hypertension, primary angle closure without glaucoma damage (PAS or high TOP with no optic nerve or visual field loss), unspecified open-angle glaucoma, primary open-angle glaucoma, chronic simple glaucoma, low-tension glaucoma, pigmentary glaucoma, capsular glaucoma with pseudo-exfoliation of lens, residual stage of open-angle glaucoma, unspecified primary angle-closure glaucoma, acute angle-closure glaucoma attack, chronic angle-closure glaucoma, intermittent angle-closure glaucoma, residual stage of angle-closure glaucoma, glaucoma secondary to eye trauma, glaucoma secondary to eye inflammation, glaucoma secondary to other eye disorders including, retinal vascular occlusions, diabetes type 1 complicated, diabetes type 2 complicated, disorders of lens, disorders of intraocular lens, disorders after other ocular symptoms, neoplasms, benign neoplasms, or malignant. Also included is glaucoma secondary to drugs, glaucoma with increased episcleral venous pressure, hypersecretion glaucoma, aqueous misdirection malignant glaucoma, glaucoma in diseases classified elsewhere, congenital glaucoma, axenfeld's anomaly, buphthalmos, glaucoma of childhood, glaucoma of newborn, hydrophthalmos, keratoglobus, congenital glaucoma macrocornea with glaucoma, macrophthalmos in congenital glaucoma, megalocornea with glaucoma, absolute glaucoma. Also included are adverse effect of ophthalmological drugs and preparations, acute follicular conjunctivitis, adverse effect of carbonic anhydrase inhibitors, and adverse effect of under dosing of ophthalmological drugs and preparations.

In some embodiments, a composition of this disclosure can be administered systemically. Systemic administration can be achieved via intravenous administration, oral administration, intraarterial administration, inhalation, intranasal administration, intra-peritoneal administration, intra-abdominal administration, subcutaneous administration, intra-articular administration, intrathecal administration, transdural administration, transdermal administration, submucosal administration, sublingual administration, enteral administration, parenteral administration, percutaneous administration, periarticular administration, or intraventricular administration.

In further embodiments, a composition of this disclosure can be administered locally. A composition may be administered locally to ocular tissue. As used herein, the term ocular tissue refers to the eye, including tissues within the sclera, e.g., the retina, and outside the sclera, e.g., ocular muscles within the orbit. Ocular tissue also includes tissues neurologically connected to, but distinct from the eye, such as the optic nerve, the geniculate nucleus and the visual cortex. Local administration to ocular tissue can be achieved via intraocular administration. Intraocular administration can be carried out via intracameral administration, intravitreal administration, or subretinal administration.

In additional embodiments, local administration to ocular tissue can be achieved via periocular administration. Periocular administration can be carried out via sub-conjunctival injection, sub-Tenon's injection, direct periocular injection, or depot periocular injection.

A subject may be administered a therapeutically effective amount of the composition. A therapeutically effective amount can be an amount effective to ameliorate, alleviate, inhibit, lessen, delay, and/or prevent at least one symptom or condition of the condition being treated.

In certain embodiments, a therapeutically effective amount can be the amount effective to ameliorate the ocular condition being treated. The dose may be determined according to various parameters, especially according to the severity of the condition, age, and weight of the patient to be treated; the route of administration; and the required regimen. A physician will be able to determine the required route of administration and dosage for any particular patient. Dosages may vary depending on the relative potency of the composition being administered, and can generally be estimated based on the half maximal effective concentration (EC50) found to be effective in in vitro and in vivo models.

Extracellular Vesicles and Aggregates in Glaucoma

Embodiments of this invention provide methods for detecting EVs in biological fluids. In certain methods, a cross-linking agent can be used to provide robust imaging of EV ultrastructures with, for example, electron microscopy. In further methods, a glutaraldehyde-alternative cross-linker can be used.

Additional embodiments of this invention contemplate detecting and characterizing EV-complexes in glaucoma. EV-complexes in glaucoma can block the TM or JCT and inhibit ocular aqueous outflow pathways.

In certain aspects, EVs in glaucoma can be aggregated together in EV-complexes. Glaucoma-associated EV-complexes may be up to multiple microns in size or diameter.

In glaucoma, EV-complexes can be an ultrastructural feature of the disease. This ultrastructural feature can be a target for characterizing glaucoma. EV-complexes can be used for detecting therapeutic parameters and modalities for glaucoma. In some embodiments, EV-complexes can be used for diagnosis, prognostication, and/or screening of glaucoma compositions. EV-complexes can also be used in devices for determining therapeutic compositions, doses and regimens.

As used herein, the term diameter refers to the longest linear dimension of an irregularly-shaped particle such as an extracellular vesicle complex. For a regularly-shaped particle, such as a spherical vesicle, the term diameter has its usual meaning as the line segment passing through the center with endpoints on the sphere.

In some aspects, this disclosure provides compositions of purified EV-complexes from glaucoma. Purified EV-complexes from glaucoma can be used in a device for assaying and detecting changes in EV ultrastructural components which can be related to intraocular pressure and ocular outflows. This invention provides devices containing purified EV-complexes which can be used for characterizing and measuring ocular blockage and ocular outflows. Purified EV-complexes from glaucoma can be used in a device for screening effects of therapeutic agents on ocular EV ultrastructural components.

In further aspects, this disclosure provides compositions of synthetic EV-complexes for characterizing glaucoma. Synthetic EV-complexes for characterizing glaucoma can be used in a device for assaying and detecting changes in EV ultrastructural components which can be related to intraocular pressure and ocular outflows. This invention provides devices containing synthetic EV-complexes which can be used for characterizing and measuring ocular blockage and ocular outflows. Synthetic EV-complexes from glaucoma can be used in a device for screening effects of therapeutic agents on ocular EV ultrastructural components.

EV ultrastructural components such as EV-complexes can be composed of complexes or aggregates of extracellular vesicles. Examples of extracellular vesicles include exomeres, exosomes, multivesicular bodies, intraluminal vesicles (ILVs), multivesicular endosomes (MVEs), oncosomes, micro-vesicles, apoptotic bodies, and vesicles originating from endosome or plasma membranes.

Complexes or aggregates of extracellular vesicles can be protein-EV structures having micrometer diameters, or diameters greater than about 1 micrometer.

Extracellular vesicle aggregates can have a size of from about 360 to about 21,000 nanometers (nm).

For example, exomeres can be about 35 nm in diameter, exosomes can be about 40-100 nm in diameter, micro-vesicles can be about 100-1000 nm in diameter, and apoptotic bodies can be about 1-5 micrometers in diameter.

Complexes or aggregates of extracellular vesicles may contain 10, 20, 30, 40, 50, 100, 200, 500 or more extracellular vesicles.

For example, a healthy subject may have free EVs, which are non-aggregated EVs, about 100-200 nm in diameter, which are mainly exosomes, along with some micrometer sized vesicles. A healthy subject may not have EV-aggregates or EV ultrastructural features larger than 0.4-20 micrometers in diameter in aqueous humor.

For example, in glaucoma, a subject may have EV-aggregates larger than 0.4-20 micrometers in diameter. A healthy subject may have small EV aggregates of about 36-300 nm, which are mainly exomeres, along with some micro-vesicles. A glaucoma subject may have reduced amounts of free EVs, or very few remaining free EVs. Free EVs in glaucoma may be of larger sizes than free EVs in a healthy subject. EV aggregates in glaucoma may be composed of any of exomeres, exosomes, micro-vesicles, and/or apoptotic bodies, as well as other kinds of vesicles or bodies.

Devices for Glaucoma Aggregational Features

A device of this invention can be used to characterize the activity of a biologically active agent toward glaucoma. A device of this invention can be used to detect or characterize ocular conditions or parameters in a model system or patient pathology.

An active agent may be capable of providing a therapeutic benefit, especially in glaucoma. In some embodiments, an active agent may be a known drug effective for treating a disease of the eye.

In some aspects, a fluid composition in a device of this invention can be analyzed by various techniques. For example, a fluid composition can be analyzed by an imaging technique.

Examples of imaging techniques include electron microscopy, stereoscopic microscopy, wide-field microscopy, polarizing microscopy, phase contrast microscopy, multiphoton microscopy, differential interference contrast microscopy, fluorescence microscopy, laser scanning confocal microscopy, multiphoton excitation microscopy, ray microscopy, and ultrasonic microscopy.

Examples of imaging techniques include positron emission tomography, computerized tomography, and magnetic resonance imaging.

Examples of assay techniques include colorimetric assay, chemiluminescence assay, spectrophotometry, and light scattering.

Figure 3:
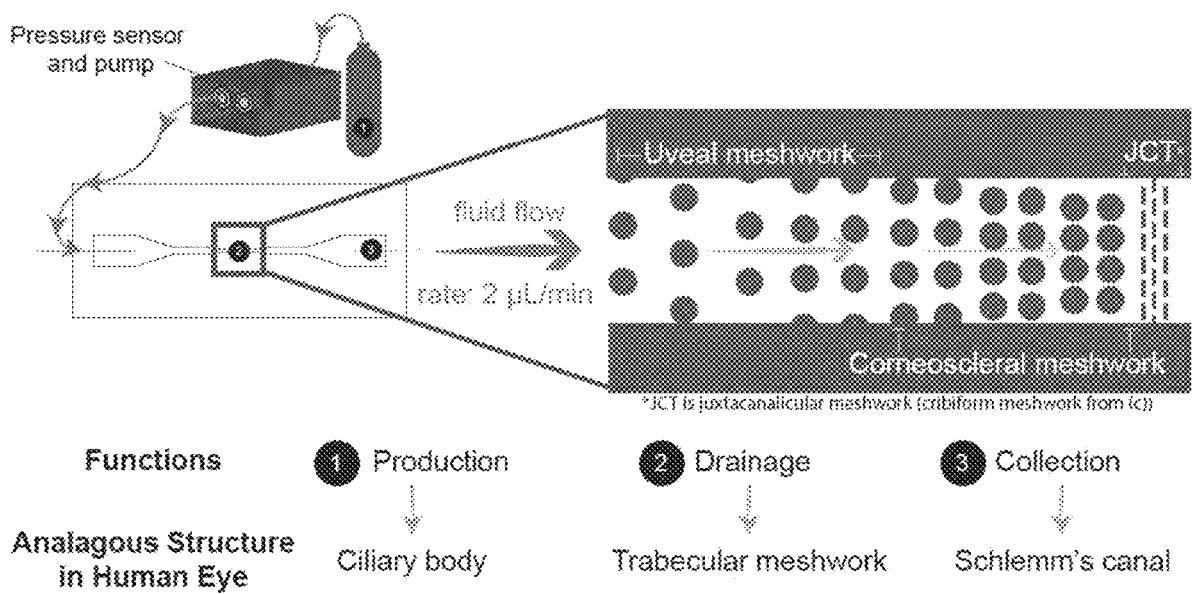
FIG. 3 shows a diagram of an embodiment of a device for detecting flow and pressure of a fluid composition in a channel. The channel may contain a meshwork having properties like a trabecular meshwork of the eye. The channel meshwork may have a uveal meshwork portion, a corneoscleral meshwork portion, and a justacanalicular meshwork portion. The channel can be a microfluidic channel.

In some embodiments, this invention can provide a device for measuring pressure and flow rate of a fluid composition. (FIG. 3) The device may have a channel having an inlet at a first end and an outlet at a second end, wherein the inlet and outlet are in fluid communication. The device can have a meshwork composition lodged in the channel for providing resistance to flow. The meshwork composition may have any one or more, or all of the following portions. A uveal meshwork, a corneoscleral meshwork, and a juxtacanalicular meshwork.

In some embodiments, a meshwork composition can be composed of glass beads, micro beads, magnetic beads, gel particles, dextran particles, or polymer particles. A meshwork composition may also be composed of glass fibers, polymeric fibers, inorganic fibers, organic fibers, or metal fibers.

In certain embodiments, a uveal meshwork may have fenestrations of about 25 micrometers. A corneoscleral meshwork may have fenestrations of about 2-15 micrometers. A juxtacanalicular meshwork may have fenestrations of about 1 to 4 micrometers or less.

A device may further include a fluid reservoir for holding the fluid composition, so that the fluid reservoir is in fluid communication with the inlet of the channel for introducing the fluid composition into the inlet of the channel.

A device of this disclosure can have a pressure source for applying pressure to the fluid composition in the fluid reservoir for introducing the fluid composition into the inlet of the channel.

A device of this invention can have a flow sensor in fluid communication with the fluid composition for measuring the flow rate and pressure of the fluid composition at the inlet of the channel and transmitting the flow rate and pressure to a processor.

Signals and data from the device can be received by a processor. The processor can display the flow rate and pressure. Memory or media can store instructions or files, such as a machine-readable storage medium. A machine-readable storage medium can be non-transitory.

A processor of this disclosure can be a general purpose or special purpose computer. A processor can execute instructions stored in a machine readable storage device or medium. A processor can include an integrated circuit chip, a microprocessor, a controller, a digital signal processor, any of which can be used to receive and/or transmit data and execute stored instructions. A processor can also transform data, and/or store data in memory, media or a file. A processor may receive and execute instructions which may include performing one or more steps of a method of this invention. A device of this invention can include one or more non-transitory machine-readable storage media, one or more processors, one or more memory devices, and/or one or more user interfaces. A processor my have an integral display for displaying data or transformed data.

In some aspects, a device may have a microfluidic channel. One or more channels can also be arranged in a microfluidic chip.

A device of this disclosure can include one or more detectors for analyzing the fluid composition within the channel or at the inlet or exiting the outlet of the channel. One or more detectors can also be arranged to detect the fluid composition within the channel.

A device of this invention may include a meshwork composition which contains extracellular vesicles or extracellular vesicle complexes. An EV-complex for use in a meshwork composition may be purified from glaucoma ocular humor. The ocular humor may be from animal or clinical sources. An EV-complex for use in a meshwork composition may be composed of extracellular vesicles, and may have a diameter from about 360 to about 21,000 nanometers.

In certain embodiments, an EV-complex for use in a meshwork composition may include a fixative, a stabilizing component, or a cross linking component which can transform the structure to a stable, uniform composition.

Examples of stabilizing components include fixatives as described herein, cross linking compounds as described herein, organic solvents, polypeptides, and pharmaceutically-acceptable organic salts.

Examples of salts include ammonium salts, alkali metal salts including sodium, lithium, and potassium salts, alkaline earth metal salts including calcium and magnesium salts, salts with organic bases, for example, organic amines, such as benzathines, dicyclohexylamines, hydrabamines formed with N,N-bis(dehydroabietyl)ethylenediamine), N-methyl-D-glucamines, N-methyl-D-glucamides, t-butyl amines, and salts with amino acids including arginine and lysine.

Examples of salts include acetates, adipates, alginates, ascorbates, aspartates, benzoates, benzenesulfonates, bisulfates, borates, butyrates, citrates, camphorates, camphorsulfonates, cyclopentanepropionates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, digluconates, dodecylsulfates, ethanesulfonates, fumarates, glucoheptanoates, glycerophosphates, hemisulfates, heptanoates, hexanoates, 3-phenylpropionates, phosphates, picrates, pivalates, propionates, salicylates, succinates, sulfates, sulfonates, tartarates, thiocyanates, toluenesulfonates, and undecanoates.

Extracellular vesicle complexes that are cross linked can be reversibly cross linked, or non-reversibly cross linked.

Extracellular vesicles that are cross linked can be reversibly cross linked, or non-reversibly cross linked.

In some embodiments, a device of this invention may contain an EV-complex meshwork composition that can be used for identifying or screening active agents for effects in reducing IOP and/or increasing ocular outflows. An EV-complex for use in a meshwork composition may include a drug delivery excipient. An EV-complex meshwork composition for a device may be a synthetic EV-complex or a purified EV-complex.

Figure 4:
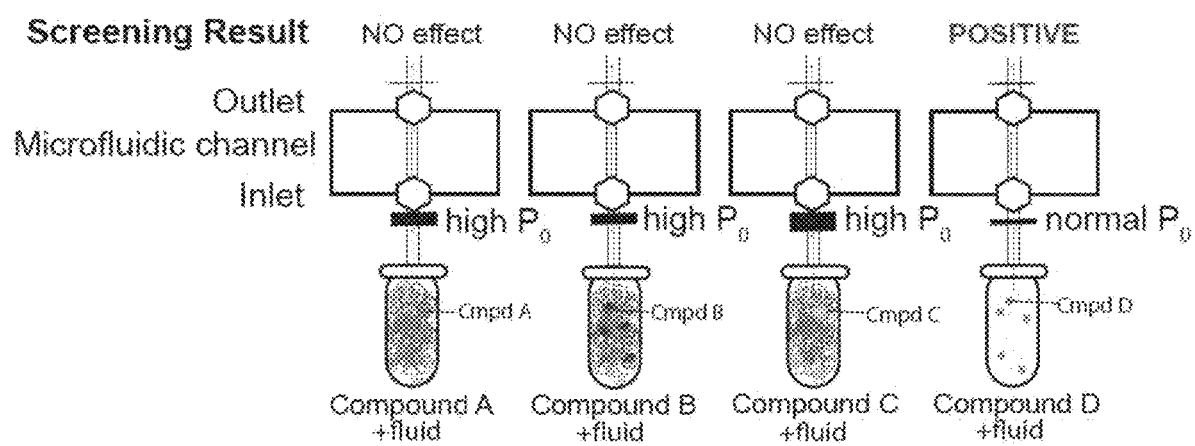
FIG. 4 shows an embodiment of a series of test channels for detecting the effect or various compounds, compositions and substances on the flow and pressure of a fluid composition in a channel.

An embodiment of an arrangement of channels of this invention is illustrated in FIG. 4.

Figure 5:
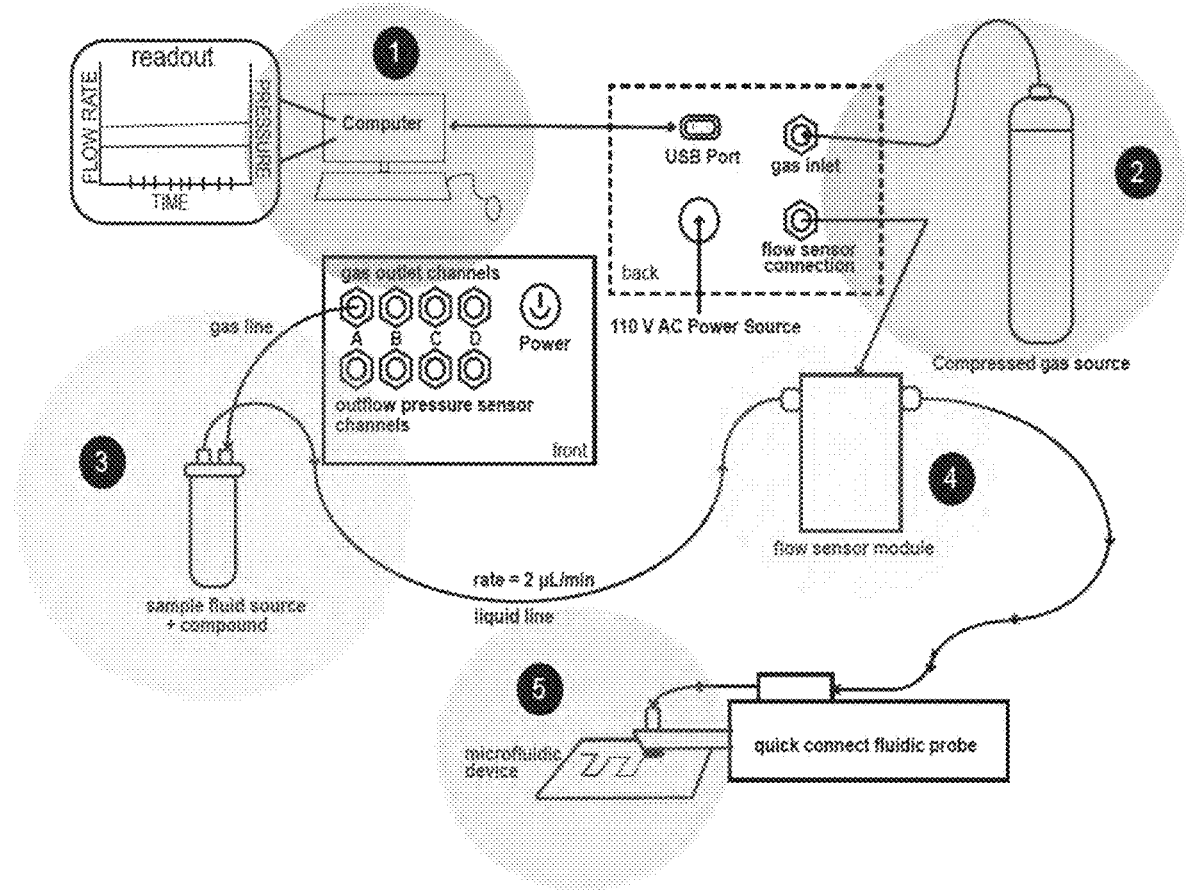
FIG. 5 shows an embodiment of a device and system for detecting flow and pressure of a fluid composition in a channel. A channel may contain a meshwork having properties like a trabecular meshwork of the eye. Alternatively, the device may utilize a reservoir for a test sample of a fluid composition. The channel can be a microfluidic channel.

An embodiment of a device of this invention is illustrated in FIG. 5.

In additional embodiments, a device of this invention may be used for measuring the quantity or level of an EV-complex in a test sample. Measuring the quantity or level of an EV-complex in a test sample can provide a diagnostic marker level for the test sample. A device of this invention can be used to identify glaucoma or pre-glaucoma in a subject.

In further embodiments, a device of this invention may be used for measuring a pressure which can be related to a quantity or level of an EV-complex in a test sample. A pressure value in a channel can be related directly to a quantity or level of an EV-complex in a test sample.

In certain embodiments, a device of this invention may be used for measuring an assay value which can be related to a quantity or level of an EV-complex in a test sample. An assay value of a composition in a channel can be related directly to a quantity or level of an EV-complex in a test sample. For example, an assay may be a colorimetric assay, a chemiluminescence assay, a spectrophotometry assay, or a light scattering assay.

In some aspects, an aqueous humor sample from a subject can be provided and analyzed for a quantity of glaucoma extracellular vesicle complexes. The subject can be identified as having glaucoma or pre-glaucoma based on the quantity exceeding a reference value. A reference value can be a quantity or level of glaucoma extracellular vesicle complexes in a reference population of healthy individuals. The subject can be diagnosed as having glaucoma or pre-glaucoma. Subsequent test samples from the subject can be used to monitor a quantity or level of glaucoma extracellular vesicle complexes exceeding or not exceeding a previous test sample, which can be related to reducing IOP and/or increasing ocular outflows in the subject.

In certain embodiments, a quantity or level of glaucoma extracellular vesicle complexes may include one or more of the number, size, density, morphology, and spatial distribution of the extracellular vesicle complexes.

In some embodiments, a reference value can be a quantity or level of glaucoma extracellular vesicle complexes in a reference population of healthy individuals. The reference value can be the average value in samples from the reference population.

Glaucoma may be found in a subject where a test sample from the subject contains a quantity or level of glaucoma extracellular vesicle complexes exceeding a glaucoma reference value.

In certain embodiments, a glaucoma reference value can be a number of extracellular vesicle complexes which contain 10 or more aggregated extracellular vesicles is zero per sample. In certain embodiments, a glaucoma reference value can be a number of extracellular vesicle complexes which contain 10 or more aggregated extracellular vesicles is 10 per sample. In certain embodiments, a glaucoma reference value can be a number of extracellular vesicle complexes which contain 10 or more aggregated extracellular vesicles is 50 per sample. In certain embodiments, a glaucoma reference value can be a number of extracellular vesicle complexes which contain 10 or more aggregated extracellular vesicles is 100 per sample.

In certain embodiments, a glaucoma reference value can be that the number of extracellular vesicle complexes which contain 10 or more aggregated extracellular vesicles, wherein the complexes are larger than 360 nm, is zero per sample. In certain embodiments, a glaucoma reference value can be that the number of extracellular vesicle complexes which contain 10 or more aggregated extracellular vesicles, wherein the complexes are larger than 360 nm, is 10 per sample. In certain embodiments, a glaucoma reference value can be that the number of extracellular vesicle complexes which contain 10 or more aggregated extracellular vesicles, wherein the complexes are larger than 360 nm, is 50 per sample. In certain embodiments, a glaucoma reference value can be that the number of extracellular vesicle complexes which contain 10 or more aggregated extracellular vesicles, wherein the complexes are larger than 360 nm, is 100 per sample.

In certain embodiments, a glaucoma reference value can be the number of extracellular vesicle complexes larger than 360 nm is 10 per sample. In certain embodiments, a glaucoma reference value can be the number of extracellular vesicle complexes larger than 360 nm is 50 per sample. In certain embodiments, a glaucoma reference value can be the number of extracellular vesicle complexes larger than 360 nm is 100 per sample. In certain embodiments, a glaucoma reference value can be the number of extracellular vesicle complexes larger than 360 nm is 200 per sample.

In additional aspects, a meshwork composition in a device of this invention can be an anterior half or portion of an animal eye with lens, wherein the TM of the eye is oriented in between the inlet and the outlet of the channel.

Methods

Extracellular vesicles in the aqueous humor in patients with POAG may be compared to a population of healthy controls. EV complex ultrastructure in the aqueous humor in subjects with ocular pathology such as glaucoma can be compared to healthy controls such as subjects with no ocular pathology aside from cataracts. The level of EV complexes in the aqueous humor in glaucoma subjects can exceed the level in healthy subjects.

The kind of EVs in glaucoma aqueous humor can be larger than in healthy subjects. In some embodiments, the level of larger EV structures can be reduced to un-block the aqueous humor meshwork and increase humor outflows. The EV complexes in glaucoma aqueous humor can be larger than any EV in a healthy subject. In some embodiments, the level of EV complexes can be reduced to un-block the aqueous humor meshwork and increase humor outflows.

In certain embodiments, EVs in healthy human aqueous humor can be diffusely and evenly distributed without aggregation. Healthy control aqueous humor may contain EVs that are non-aggregated and have diffuse distribution.

Glaucoma EV-complexes can be larger than EVs observed in healthy controls and may block the trabecular meshwork.

In some embodiments, purified EV-complexes can be obtained from aqueous humor in POAG. The purified EV-complexes may be several microns in size. The glaucoma EV-complex can be larger than the opening of the JCT (1 to 4 µm, or up to 2 to 20 µm), which may be large enough to block the juxtacanalicular tissue. The EV-complexes in POAG may be used to block the trabecular meshwork and reduce aqueous outflow. In certain embodiments, the level of EV-complexes can be reduced to un-block the trabecular meshwork and increase aqueous outflow.

For example, EV complexes can be contacted with a composition containing an active agent such as bimatoprost. In these embodiments, the level of EV-complexes can be reduced to un-block a trabecular meshwork and increase aqueous outflow.

In certain aspects, the level or quantity of glaucoma EV-complexes can be reduced in a POAG subject by administering an active agent such as bimatoprost.

In further embodiments, purified EV-complexes can have a size from about 360 nm to 21,000 nm. A purified EV-complex can be substantially larger than any particle found in healthy aqueous humor.

In additional embodiments, a purified EV-complex can have a size from about 360 nm to about 21,000 nm, or 360 nm to about 10,000 nm, or 360 nm to about 5,000 nm, or 360 nm to about 3,000 nm, or 360 nm to about 2,000 nm, or 360 nm to about 1,000 nm.

In a purified EV complex, the number of EVs contacting each other can be from about 5 to about 300, or from 10 to 300, or from 10 to 200, or from 10 to 100, or from 10 to 50, or from 10 to 40, or from 10 to 20.

In a purified EV complex, the number of EVs contacting each other can be from 20 to 300, or from 30 to 300, or from 40 to 300, or from 50 to 300.

In a purified EV complex, the number of EVs contacting each other can be from 20 to 200, or from 20 to 100, or from 30 to 200, or from 30 to 100, or from 40 to 200, or from 40 to 100, or from 50 to 200, or from 50 to 100.

In some embodiments, purified EV-complexes can provide particles of a size for a uveal meshwork. Purified EV-complexes for a uveal meshwork can be about 10,000 nm to about 25,000 nm, or 15,000 nm to 25,000 nm, or 20,000 nm to 25,000 nm.

In further embodiments, purified EV-complexes can provide particles of a size for a corneoscleral meshwork. Purified EV-complexes for a corneoscleral meshwork can be about 1,000 nm to about 15,000 nm, or 2,000 nm to 10,000 nm, or 2,000 nm to 5,000 nm.

In additional embodiments, purified EV-complexes can provide particles of a size for a juxtacanalicular meshwork. Purified EV-complexes for a juxtacanalicular meshwork can be about 360 nm to about 1,000 nm, or 360 nm to 2,000 nm, or 260 nm to 3,000 nm, or 1,000 nm to 3,000 nm.

The region of the TM that may be implicated in establishing IOP is next to Schlemm's canal and is called the juxtacanalicular tissue (JCT) or cribriform region.

EV complexes can be synthesized by contacting EVs with reagents to form larger structures. Reagents can include fixatives, cross linkers, and buffer suspensions. Synthesized EV complexes may be composed of many EVs contacting each other to form aggregates.

In a synthesized EV complex, the number of EVs contacting each other can be from about 5 to about 300, or from 10 to 300, or from 10 to 200, or from 10 to 100, or from 10 to 50, or from 10 to 40, or from 10 to 20.

In a synthesized EV complex, the number of EVs contacting each other can be from 20 to 300, or from 30 to 300, or from 40 to 300, or from 50 to 300.

In a synthesized EV complex, the number of EVs contacting each other can be from 20 to 200, or from 20 to 100, or from 30 to 200, or from 30 to 100, or from 40 to 200, or from 40 to 100, or from 50 to 200, or from 50 to 100.

In additional embodiments, a synthesized EV-complex can have a size from about 360 nm to about 25,000 nm, or 360 nm to 21,000 nm, or 360 nm to about 10,000 nm, or 360 nm to about 5,000 nm, or 360 nm to about 3,000 nm, or 360 nm to about 2,000 nm, or 360 nm to about 1,000 nm.

In some embodiments, synthesized EV-complexes can provide particles of a size for a uveal meshwork. Synthesized EV-complexes for a uveal meshwork can be about 10,000 nm to about 25,000 nm, or 15,000 nm to 25,000 nm, or 20,000 nm to 25,000 nm.

In further embodiments, synthesized EV-complexes can provide particles of a size for a corneoscleral meshwork. Synthesized EV-complexes for a corneoscleral meshwork can be about 1,000 nm to about 15,000 nm, or 2,000 nm to 10,000 nm, or 2,000 nm to 5,000 nm.

In additional embodiments, synthesized EV-complexes can provide particles of a size for a juxtacanalicular meshwork. Synthesized EV-complexes for a juxtacanalicular meshwork can be about 360 nm to about 1,000 nm, or 360 nm to 2,000 nm, or 260 nm to 3,000 nm, or 1,000 nm to 3,000 nm.

Synthesis and Purification of Extracellular Vesicles and EV-Complexes

In some embodiments, extracellular vesicles including exosomes and EV-complexes can be synthesized, isolated, and/or purified by size exclusion chromatography or gel filtration chromatography.

In certain embodiments, extracellular vesicles including exosomes and EV-complexes can be synthesized, isolated, and/or purified by centrifugation, differential centrifugation, density gradient centrifugation, or ultracentrifugation.

In additional embodiments, extracellular vesicles including exosomes and EV-complexes can be synthesized, isolated, and/or purified using precipitation reagents, for example polymeric precipitation reagents, protamine, sodium acetate, or organic solvents.

In some embodiments, extracellular vesicles including exosomes and EV-complexes can be synthesized, isolated, and/or purified using immunoaffinity capture techniques.

In further embodiments, extracellular vesicles including exosomes and EV-complexes can be synthesized, isolated, and/or purified using microfluidic devices, acoustic fluidic devices, and microfluidic chips.

In additional embodiments, extracellular vesicles including exosomes and EV-complexes can be synthesized, isolated, and/or purified using sequential filtration techniques.

In further embodiments, extracellular vesicles including exosomes can be detected by resistive pulse sensing using a tunable pore sensor, or tunable resistive pulse sensing.

In certain embodiments, extracellular vesicles including exosomes can be detected by electron microscopy, light microscopy and flow cytometry.

In additional embodiments, extracellular vesicles including exosomes can be detected by dynamic light scattering and/or mass spectrometry.

In some aspects, extracellular vesicles including exosomes and EV-complexes can be synthesized, isolated, and/or purified by first isolating the vesicles from cell culture.

In certain aspects, extracellular vesicles including exosomes and EV-complexes can be synthesized, isolated, and/or purified by first isolating the vesicles from bodily fluids, such as ocular humor. The isolated vesicles can be diluted, filtered and protected with protease inhibitors.

In further embodiments, steps for purification of extracellular vesicles including exosomes and EV-complexes include contacting with a fixative.

In some aspects, extracellular vesicles including exosomes can be synthesized by controlled biogenesis and release from in vitro grown cell lines.

Active Agents

Examples of active agents include small molecule drugs, proteins, nucleic acids, polysaccharides, biologics, and combinations thereof.

Examples of active agents include cytokines, growth factors, proteins, peptides, anti-metabolites, signaling modulators, antibiotics, antibodies, chemotherapeutic compounds, and combinations thereof.

Examples of active agents include antiinfective agents, anesthetic agents, anti-VEGF agents, anti-inflammatory agents, an intraocular pressure reducing agent, and combinations thereof.

Examples of active agents include anesthetics, analgesics, and combinations thereof.

Examples of active agents include cell transport or mobility impending agents such as colchicine, vincristine, cytochalasin B, and combinations thereof.

Examples of active agents include antiglaucoma drugs.

Examples of active agents include beta-blockers such as timolol, betaxolol, atenolol, prostaglandins, and combinations thereof.

Examples of active agents include lipid-receptor agonists or prostaglandin analogues such as bimatoprost, travoprost, tafluprost, latanoprost, unoprostone, and combinations thereof.

Examples of active agents include alpha-adrenergic agonists including brimonidine, dipivefrine, and combinations thereof.

Examples of active agents include carbonic anhydrase inhibitors such as acetazolamide, methazolamide, dichlorphenamide, diamox, and combinations thereof.

Examples of active agents include and neuroprotectants such as nimodipine.

Examples of active agents include agents for dry AMD such as rapamycin, glatiramer acetate, complement C5aR blocker, ciliary neurotrophic factor, fenretinide, rheopheresis, and combinations thereof.

Examples of active agents include agents for wet AMD such as mecamylamine; VEGF trap eye, complement inhibitor POT-4.

Examples of active agents include kinase inhibitors such as bevacizumab, BIBW 2992, cetuximab, imatinib, trastuzumab, gefitinib, ranibizumab, pegaptanib, sorafenib, dasatinib, sunitinib, erlotinib, nilotinib, lapatinib, panitumumab, vandetanib, E7080, and combinations thereof.

Examples of active agents include antibiotics such as tetracycline, chlortetracycline, bacitracin, neomycin, polymyxin, gramicidin, oxytetracycline, chloramphenicol, gentamycin, and erythromycin.

Examples of active agents include antibacterials such as sulfonamides, sulfacetamide, sulfamethizole and sulfisoxazole.

Examples of active agents include anti-fungal agents such as fluconazole, nitrofurazone, amphotericin B, and ketoconazole.

Examples of active agents include anti-viral agents such as trifluorothymidine, acyclovir, ganciclovir, DDI, AZT, foscarnet, vidarabine, trifluorouridine, idoxuridine, ribavirin, protease inhibitors, and anti-cytomegalovirus agents.

Examples of active agents include antiallergenics such as methapyriline; chlorpheniramine, pyrilamine and prophenpyridamine.

Examples of active agents include anti-inflammatories such as hydrocortisone, dexamethasone, fluocinolone, prednisone, prednisolone, methylprednisolone, fluorometholone, betamethasone and triamcinolone.

Examples of active agents include decongestants such as phenylephrine, naphazoline, and tetrahydrazoline; miotics, and muscarinics.

Examples of active agents include anti-cholinesterases such as pilocarpine, carbachol, di-isopropyl fluorophosphate, phospholine iodine, and demecarium bromide.

Examples of active agents include mydriatics such as atropine sulfate, cyclopentolate, homatropine, scopolamine, tropicamide, eucatropine.

Examples of active agents include sympathomimetics such as epinephrine.

Examples of active agents include ranibizumab, bevacizamab, and triamcinolone.

Examples of active agents include antiinflammatories, such as non-steroidal anti-inflammatories (NSAID) including acetylsalicylic acid, ibuprofen, indomethacin; and COX-2 inhibitors.

Examples of active agents include immunosuppressive agents including sirolimus.

Examples of active agents include matrix metalloproteinase (MMP) inhibitors such as tetracycline.

Examples of active agents include anticlotting agents such as heparin, antifibrinogen, fibrinolysin, and anti-clotting activase.

Examples of active agents include antidiabetic agents including acetohexamide, chlorpropamide, glipizide, glyburide, tolazamide, tolbutamide, insulin, and aldose reductase inhibitors.

Examples of active agents include amines such as Thonzonium.

Examples of active agents include detergents such as Taurocholic acid, Glycocholic acid, Glycochenodeoxycholic Acid, Benzalkonium, Cetylpyridinium, Taurochenodeoxycholic acid, Polidocanol, and Tyloxapol.

Examples of active agents include lipids such as Sodium lauryl sulfate.

Examples of active agents include antibacterials such as Polymyxin B.

Examples of active agents include amines such as Thonzonium and related compounds Thonzylamine, mepyramine and Piribedil.

Examples of active agents include Ophthalmics such as Aceclidine, Acetazolamide, Acetylcysteine, Acyclovir, Aflibercept, Alcaftadine, Alclometasone, Alteplase, Ampicillin, Anecortave, Ascorbic acid, Atropine, Azelastine, Azithromycin, Befunolol, Bendazac, Benzylpenicillin, Besifloxacin, Betamethasone, Betaxolol, Bibrocathol, Bimatoprost, Brimonidine, Brinzolamide, Bromfenac, Carbamoylcholine, Carteolol, Cefuroxime, Cenegermin, Chloramphenicol, Chlorhexidine, Chlortetracycline, Chymotrypsin, Cinchocaine, Ciprofloxacin, Clobetasone, Clonidine, Cocaine, Cortisone, Cromoglicic acid, Cyclopentolate, Cyclosporine, Cysteamine, Dapiprazole, Demecarium, Desonide, Dexamethasone, Dexpanthenol, Dibrompropamidine, Diclofenac, Diclofenamide, Dihydrostreptomycin, Dipivefrin, Dorzolamide, Echothiophate, Edetate sodium, Emedastine, Ephedrine, Epinastine, Epinephrine, Erythromycin, Ethylmorphine, Famciclovir, Fludrocortisone, Fluocinolone acetonide, Fluocortolone, Fluorescein, Fluorometholone, Flurbiprofen, Fomivirsen, Formocortal, Framycetin, Fusidic acid, Ganciclovir, Gatifloxacin, Gentamicin, Guaiazulen, Guanethidine, Heparin, Hexamidine, Homatropine, Hyaluronic acid, Hydrocortisone, Hypromellose, Ibopamine, Idoxuridine, Indomethacin, Inosine, Kanamycin, Ketorolac, Ketotifen, Latanoprost, Levobunolol, Levocabastine, Levofloxacin, Lidocaine, Lifitegrast, Lodoxamide, Lomefloxacin, Loteprednol, Medrysone, Methazolamide, Methscopolamine, Methylprednisolone, Metipranolol, Micronomicin, Moxifloxacin, Nandrolone, Naphazoline, Natamycin, Nedocromil, Neomycin, Neostigmine, Nepafenac, Netarsudil, Netilmicin, Nitrofural, Norfloxacin, Ocriplasmin, Ofloxacin, Olopatadine, Oxybuprocaine, Oxymetazoline, Oxyphenbutazone, Oxytetracycline, Paraoxon, Pegaptanib, Phenylephrine, Physostigmine, Picloxydine, Pilocarpine, Piroxicam, Polymyxin B, Potassium Iodide, Povidone-iodine, Pranoprofen, Prednisolone, Procaine, Propamidine, Propanoic acid, Proparacaine, Ranibizumab, Resorcinol, Riboflavin, Rifamycin, Rimexolone, Rose bengal free acid, Salicylic acid, Scopolamine, Sirolimus, Sodium borate, Spaglumic Acid, Sulfacetamide, Sulfadicramide, Sulfamethizole, Sulfaphenazole, Sulfisoxazole, Synephrine, Tafluprost, Tetracaine, Tetracycline, Tetryzoline, Timolol, Tobramycin, Travoprost, Triamcinolone, Trifluridine, Tropicamide, Tyrothricin, Unoprostone, Verteporfin, Vidarabine, Vitamin A, and Xylometazoline.

Examples of active agents include anti-cancer agents such as 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levamisole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine.

Examples of active agents include hormones, peptides, steroids, nucleic acids, saccharides, lipids, glycolipids, and glycoproteins.

Examples of active agents include endocrine hormones such as pituitary, insulin, insulin-related growth factor, thyroid, and growth hormones.

Examples of active agents include heat shock proteins.

Examples of active agents include immunological response modifiers such as muramyl dipeptide, cyclosporins, interferons, interleukin-2, cytokines, tacrolimus, tumor necrosis factor, pentostatin, thymopentin, transforming factor beta2, and erythropoietin.

Examples of active agents include brain nerve growth factor (BNGF), ciliary nerve growth factor (CNGF), and vascular endothelial growth factor (VEGF).

Examples of active agents include anti-coagulants, anti-proliferatives, quinoxalines, and potassium channel blockers.

Examples of active agents include guanylate cyclase inhibitor, such as methylene blue, butylated hydroxyanisole, N-methylhydroxylamine, 2-(4-methylaminobutoxy) diphenylmethane, and apraclonidine.

Examples of active agents include prostaglandins such as metabolite derivatives of arachidonic acid.

Examples of active agents include sugars, such as trehalose.

Examples of active ingredients include viscoelastic agents including hyaluronic acid, dimethicone, and Hypromellose.

Examples of active ingredients include ophthalmic viscosurgical devices, sodium hyaluronate, chondroitin sulfate, hydroxypropyl methycellulose, hydroxy-propyl-methylcellulose, hyaluronic acid, dimethicone, and hypromellose.

Examples of active agents include detergents, purifying or cleansing agents, for example salts of long-chain aliphatic bases or acids, which can have cleansing, oil-dissolving, and/or antimicrobial effects. Examples of active agents include Glycochenodeoxycholic Acid, Glycocholic acid, Peanut oil, Benzalkonium, Cetylpyridinium, Taurochenodeoxycholic acid, Polidocanol, Tyloxapol, Taurocholic acid, and N-Dodecyl-N,N-Dimethyl-3-Ammonio-1-Propanesulfonate.

Embodiments of this invention further contemplate use of active agents for treating glaucoma disorders. In some aspects, a glaucoma disorder may be treated by administering a surface active agent for affecting EV-complexes. An effective amount a surface active agent can be administered for ameliorating, alleviating, inhibiting, lessening, delaying, and/or preventing at least one symptom or condition of a glaucoma disorder. As used herein, the term surface active agent refers broadly to surfactants, detergents, purifying or cleansing agents, soaps, and modified variations thereof.

Examples of active agents include surfactants including Lucinactant, Calfactant, Beractant, Tyloxapol, Sodium lauryl sulfoacetate, Thonzonium, Nonoxynol-9 Cetalkonium, Dimethicone, Polyethylene glycol 400, Sinapultide, Palmitoyloleoyl-phosphatidylglycerol, Lapyrium, Sodium Lauryl Sulfate (SLS), Polyethylene glycol 300, Trolamine, Polysorbate 80, Poloxamer 407, Sodium tetradecyl sulfate, Polysorbate 20, Docusate, Poractant alfa, Colfosceril palmitate, Castor oil, Benzalkonium, N-alkyl ethylbenzyl dimethyl ammonium (c12-c14), Quaternium-15, Ambroxol, Pumactant, Ethanolamine, Lecithin, soybean, and Cocamidopropyl betaine.

Examples of active agents include agents as described herein can be modified for delivery or metabolic acceptability, or can be PEGylated with a polyethylene glycol chain, or have a polypropylene glycol chain attached. This disclosure includes the agents described above as modified active agents, or PEGylated, or with other chain modifications.

Examples of active agents include antibodies, antibody fragments, VEGF inhibitors, small molecules, corticosteroids, and combinations thereof.

Examples of active agents include tyrosine kinase inhibitors, monoclonal antibodies, and combinations thereof.

Examples of active agents include antibodies and antibody fragments. The term "antibody" as referred to herein includes whole antibodies, e.g., two heavy chains and two light chains, antibody binding fragments thereof, e.g., single chain antibodies (scFv), single domain antibodies, e.g., nanobodies or Fv, Fab, Fab', F(ab')2, and, variants thereof, e.g., tandem scFv, Fd fragments, diabodies, triabodies. Antibody fragments may be obtained using conventional techniques known to those of skill in the art, and the fragments may be used in the same manner as intact antibodies.

Antibody and antibody fragments as disclosed herein can be mono-valent, bi-valent, or tri-valent with regard to binding domains, and the binding domains may be mono-specific, bi-specific, or tri-specific in binding specificity by design. Suitable antibodies include monoclonal antibodies or a polyclonal antibody mixture. The antibody may be a chimeric antibody, a CDR-grafted antibody, a humanized antibody or an antigen binding portion of any of the foregoing thereof. Therapeutic antibodies may be derived from a variety of species, including, without limitation, mouse, human, camel, llama, goat, rabbit, bovine, and cartilaginous fish.

In some embodiments, an antibody or antigen binding fragment thereof can be used for the treatment of an ocular disease or condition. Examples of antibodies or antigen binding fragments include those that bind to and preferentially block or reduce the activity of integrins associated with disease, such as an anti-$\alpha v\beta 3$ integrin antibody and an anti-$\alpha 4\beta 1$ integrin antibody, anti-epidermal growth factor receptor antibody, anti-vascular endothelial growth factor (VEGF) receptor antibody, anti-VEGF antibodies, e.g., bevacizumab, ranibizumab, anti-TNF$\alpha$ antibodies, e.g., infliximab and adalimumab, an anti-fibroblast growth factor antibody, an anti-epidermal growth factor antibody, an anti-CD20 antibody, an anti-CD52 antibody, an anti-CD11a antibody, and anti-IL-2 antibody.

In further embodiments, a therapeutic protein can be an antibody mimetic.

As used herein, the term "antibody mimetic" encompasses any organic compound, e.g., a peptide or polypeptide, that can specifically bind an antigen like an antibody and is about 3-20 kDa. An antibody mimetic may comprise a scaffold which binds its target antigen via amino acids in exposed loops similar to the CDR loops of an antibody. Antibody mimetics include adnectins, lipocalins, Kunitz domain-based binders, avimers, knottins, fynomers, atrimers, and cytotoxic T-lymphocyte associated protein-4 (CTLA4)-based binders. Some examples are given in Weidle et al., *The Emerging Role of New Protein Scaffold-based Agents for the Treatment of Cancer*, Cancer Genomics & Proteomics 10:155-168 (2013).

Examples of active agents include agents used for Parkinson's such as Benzatropine, Ropinirole, Tolcapone, Trihexyphenidyl, Procyclidine, Pramipexole, Entacapone, Biperiden, Amantadine, Selegiline, Bromocriptine, Levodopa, Dexetimide, Piribedil, Budipine, Melevodopa, Profenamine, Cabergoline, Lisuride, Progabide, Gabapentin, Memantine, Orphenadrine, 3,5-Dinitrocatechol, Pimavanserin, Ifenprodil, Opicapone, Benserazide, Metixene, Apomorphine, Pergolide, Rasagiline, Rotigotine, Etilevodopam, Tropatepine, Dihydroergocryptine, Phenglutarimide, Mazaticol, Etybenzatropine, Bornaprine, Etanautine, Carbidopa, Safinamide, and Dexpramipexole Examples of active agents include prostaglandins such as Epoprostenol, Dinoprost, Carboprost tromethamine, Dinoprost tromethamine, Dinoprostone, Prostaglandin D2, Prostalene, Reidispongiolide C, Unoprostone, Gemeprost, Limaprost, Iloprost, Latanoprost, Cloprostenol, Sepetaprost, Bimatoprost, Fenprostalene, Latanoprostene Bunod, Travoprost, Carboprost Tromethamine, Dinoprost, Tafluprost, Cabazitaxel, Cloprostenol Sodium, Bimatoprost, (−)-Corey Lactone 4-Phenylbenzoate Alcohol, Dutasteride, Isopropyl Unoprostone, Beraprost Sodium, Prostaglandin E1, Cloprostenol, Remodulin, Trenbolone Cyclohexylmethylcarbonate, Prostaglandin F2a, Iloprost, Misoprostol Acid, Gemeprost, 9-deoxy-9-methylene-16,16-dimethyl Prostaglandin E2, Enoprostil, Ornoprostil, epoprostenol, Sulprostone, Iloprost, Rosaprostol, (+)-Cloprostenol sodium, Carboprost tromethamine, Carboprost, Misoprostol, Prostacyclin sodium salt, Prostaglandin E2, and Limaprost.

Examples of active agents include vitamins such as 1-alpha, 25-dihydroxyl-20-epi-22-oxa-24, 26, 27-trihomovitamin D3.

Examples of active agents include antibotics such as Brefeldin A, Fusidic acid, Ovalicin, Narasin, and Salinomycin.

Examples of active agents include steroids such as Hydrocortisone cypionate, Hydrocortisone valerate, Hydrocortisone butyrate, Hydrocortisone probutate, Hydrocortisone aceponate, Prednisolone tebutate, Trilostane Hydrocortisone acetate, Cholesteryl Linoleate, Methylprednisolone aceponate, Eldecalcitol Pregnenolone acetate, Testosterone propionate Drospirenone Clascoterone Norethindrone enanthate, Prednisolone hemisuccinate, Hydroxyprogesterone caproate, Trenbolone acetate, Fluprostenol Anecortave acetate Oleandrin Cortisone acetate, Calcipotriol Gestodene Dimethyl carbate, Calcipotriol 1alpha,24S-Dihydroxyvitamin D2, Ethynodiol diacetate, Nandrolone decanoate, Testosterone cypionate, Testosterone undecanoate, Carbenoxolone, progesterone-11-alpha-ol-hemisuccinate, Eplerenone, Testosterone succinate, and Boldenone undecylenate.

Examples of active agents include statins such as Lovastatin, atorvastatin, pravastatin, rosuvastatin, fluvastatin, and simvastatin.

Examples of active agents include aggregation inhibitors such as Pentoxifylline, Argatroban, and Von Willebrand Factor Human.

Examples of active agents include prostacyclin such as Treprostinil.

Examples of active agents include amyloid targeting agents such as caprospinol and similar compounds including Cholesteryl Linoleate, Pregnenolone acetate, and P-57AS3.

Examples of active agents include lactones such as Reidispongiolide A and Soraphen A, and Canrenone.

Examples of active agents include Benzoquinones such as Antroquinonol.

Examples of active agents include Oxepanes such as Triptolide PG-701.

Examples of active agents include Lipids such as gibberellin A4 and Fumagillin.

Examples of active agents include blood glucose lowering agents such as Mitiglinide.

Examples of active agents include central nervous system depressant such as Glutethimide.

Examples of active agents include benzenoids such as sildenafil, udenafil, and vardenafil.

Examples of active agents include carbohydrates such as Fusicoccin and treholose.

Examples of active agents include Cholinergic Agents such as Biperiden, Cycrimine, Procyclidine, and Trihexyphenidyl.

Examples of active agents include Terpenes such as Cyclohexanes.

The molecules, compounds and/or compositions of this disclosure may be asymmetric, having one or more chiral stereocenters. A compound containing one or more chiral centers can include substances described as an "isomer," a "diastereomer," a "stereoisomer," an "optical isomer," an "enantiomer," or as a "racemic mixture." Conventions for stereochemical nomenclature, for example the stereoisomer naming rules of Cahn, Ingold and Prelog, as well as methods for the determination of stereochemistry and the separation of stereoisomers are known in the art. See, e.g., March's Advanced Organic Chemistry (7th ed., 2013). The compounds, composition and structures of this disclosure are intended to encompass all possible isomers, stereoisomers, diastereomers, enantiomers, and/or optical isomers that exist for the compound, composition and/or structure, including any mixture, or racemic mixture thereof.

A compound can exist in un-solvated and solvated forms, or hydrated forms. In this disclosure, solvated forms, with pharmaceutically acceptable solvents, such as water or ethanol, are to be taken as equivalent to the un-solvated forms. Compounds and salts, or solvates thereof, may also exist in tautomeric forms, which are to be taken as equivalent.

Compositions and Formulations

An active agent of this disclosure can include drugs and agents for diseases of the eye, including small molecule drugs, peptides, antibodies and protein agents.

A formulation of an active agent may be prepared by dissolving a composition in water to produce an aqueous solution and rendering the solution sterile.

A formulation of this disclosure can be in the form of a sterile injectable aqueous or oily suspension. A suspension can be formulated including a dispersing or wetting agent. A sterile injectable preparation can be a sterile injectable solution or suspension in a non-toxic, pharmaceutically acceptable diluent or solvent.

Examples of solvents include water, water for injection, Ringer's solution, balanced salt saline, isotonic sodium chloride solution, 1,3-butanediol, synthetic mono- or diglycerides, and fatty acids such as oleic acid.

A formulation of this disclosure can be in the form of eye drops for topical delivery.

An ophthalmic formulation can be a solution or suspension for topical administration. A composition can be a viscous or semi-viscous gel, or other solid or semi-solid compositions.

An ophthalmic formulation can be locally delivered by direct injection or by use of an infusion pump.

An ophthalmic formulation can include artificial tears carriers.

An ophthalmic formulation can include a phospholipid carrier.

An ophthalmic formulation can include a surfactant, a preservative, an antioxidant, a tonicity adjusting excipient, a buffer, a co-solvent, and a viscosity excipient.

An ophthalmic formulation may include an excipient to adjust osmolarity of the formulation.

An ophthalmic formulation can include a viscosity excipient such as a polysaccharide, hyaluronic acid, chondroitin sulfate, a dextran, a cellulose polymer, a vinyl polymer, and an acrylic acid polymer.

An ophthalmic formulation may have a viscosity of from 1 to 400 centipoises, or from 1 to 100 centipoises, or from 2 to 40 cps. An ophthalmic formulation may have a viscosity of about 15, 20, 25, 30, 40, or 50 centipoises.

A dosage form of a composition of this invention can be liquid or an emulsion. A dosage form of the composition of this invention can be solid, which can be reconstituted in a liquid prior to administration.

A composition of this disclosure can also be in the form of an oil-in-water emulsion. The oily phase can be a vegetable oil or a mineral oil.

Examples of emulsifying agents include naturally-occurring gums, gum acacia, gum tragacanth, phosphatides, esters of fatty acids, hexitol, sorbitan monooleate, and polyoxyethylene sorbitan monooleate.

Embodiments of this invention can advantageously provide effective activity of an active agent at dosage levels significantly lower than conventional dosage levels.

An effective amount of an active agent composition of this disclosure can be an amount sufficient to ameliorate or reduce a symptom of the disease treated.

A composition may be administered as a single dosage or may be administered in a regimen with repeated dosing.

An appropriate dosage level of an active agent can be determined by a skilled artisan. In some embodiments, an active agent can be present in a composition in an amount from about 0.001% to about 40%, or from about 0.01% to about 20%, or from about 0.1% to 10% by weight of the total formulation.

An active agent of this disclosure can be combined with one or more pharmaceutically acceptable carriers. A carrier can be in a variety of forms including fluids, viscous solutions, gels, or solubilized particles. Examples of carriers include pharmaceutically acceptable diluents, solvents, saline, and various buffers.

Some examples of carriers, excipients and additives are given in U.S. Pharmacopeia National Formulary (2014); Handbook of Pharmaceutical Excipients (7th ed., 2013); Remington: The Science and Practice of Pharmacy (22nd ed. 2013); Remington's Pharmaceutical Sciences (Mack Publishing Co. 1990). Some examples of drugs and delivery are given in Goodman and Gilman, The Pharmacological Basis of Therapeutics (13th ed. 2018, McGraw Hill, N.Y.).

In certain embodiments, an active agent may be delivered without a carrier for reducing extracellular vesicle complexes in glaucoma ocular humor.

Examples of carriers include pyrogen free water; isotonic saline, Ringer's solution, ethyl alcohol, and phosphate buffer solution.

A formulation of this disclosure may include a polymer such as a polyethylene glycol (PEG), polypropylene glycol, or poly(lactic-co-glycolic acid) having a molecular weight of about 0.2 to about 50 kDa.

Examples of carrier polymers include polyvinyl acetate, polyvinyl alcohol, polyvinylpyrrolidone, chitosan, collagen, sodium alginate, gelatin, hyaluronic acid, polylactic acid, poly(lactic acid-glycolic acid) copolymer, polyhydroxybutyric acid, poly(hydroxybutyric acid-glycolic acid) copolymer, cellulose, hydroxymethylcellulose, hydroxypropylcellulose, fatty acid esters, and polyglycerins.

Examples of additives include saccharides, sucrose, mannitol, lactose, L-arabinose, D-erythrose, D-ribose, D-xylose, D-mannose, D-galactose, lactulose, cellobiose, gentibiose, glycerin, polyethylene glycol, N-methylpyrrolidone, oligovinyl alcohol, ethanol, ethylene glycol, and propylene glycol.

Examples of solubility enhancing agents include cyclodextrins.

A formulation can include galactose, lactose, mannitol, monosaccharide, fructose, maltose, galactose, glucose, D-mannose, sorbose, disaccharide, lactose, sucrose, trehalose, cellobiose, polysaccharide, maltodextrin, dextran, starch, mannitol, or xylitol.

An ophthalmic formulation may include a lipid such as dipalmitoylethylphosphocholine, dioleoyl phosphatidylethanolamine, or 3β-[N—(N',N'-Dimethylaminoethane)-carbamoyl] cholesterol.

An ophthalmic formulation may include a lipid such as 1,2-Dioleoyl-sn-Glycero-3-[Phospho-L-Serine], 1,2-Dioleoyl-sn-Glycero-3-Phosphate.

An ophthalmic formulation may include a lipid such as 1,2-Dipalmitoyl-sn-Glycero-3-Phosphocholine, distearoylphosphatidylcholine, diarachidoylphosphatidylcholin, dipalmitoyl phosphatidylethanolamine.

An ophthalmic formulation may include a fatty acid, oleic acid, myristoleic, or aracadonic acid.

An ophthalmic formulation may include a phospholipid such as phosphatidylcholine, lecithin, phosphatidylglycerol, phosphatidylinositol, phosphatidylserine, and phosphatidylethanolamine.

An ophthalmic formulation may include a polymer such as polyvinylpyrrolidone, hydroxymethylcellulose, hydroxyethylcellulose, hydroxypropylmethylcellulose, hydroxyethylstarch, cyclodextrin, 2-hydroxypropyl-β-cyclodextrin, sulfobutylether-β-cyclodextrin, polyethylene glycol, pectin, poly(lactide-co-glycolide), polylactide, polyethylene imine, or poly-L-lysine.

In some embodiments, an ophthalmic formulation may include one or more of a pH adjusting excipient, a buffering excipient, a tonicity excipient, a viscosity excipient, or a wetting excipient. In certain embodiments, an ophthalmic formulation may include an acidifying excipient, a preservative, an antioxidant, a solubilizing excipient, a humectant, or a suspending excipient.

An ophthalmic formulation may include additives, diluents, delivery vehicles, or carrier materials such as a polymer, a polyethylene glycol, a dextran, a diethylaminoethyl dextran, a cyclodextrin, or a carboxymethyl cellulose.

Examples of excipients include sodium chloride, sodium dihydrogen phosphate monohydrate, and disodium hydrogen phosphate anhydrous.

Examples of formulation additives include vegetable oils, olive oil, sesame oil, coconut oil, mineral oil, and paraffin.

Examples of dispersing or wetting agents include lecithin, polyoxyethylene stearate, heptadecaethyleneoxycetanol, polyoxyethylene sorbitol monooleate, and polyethylene sorbitan monooleate.

Examples of antioxidants include ascorbic acid, cysteine hydrochloride, sodium bisulfite, sodium metabisulfite, sodium sulfite, ascorbyl palmitate, butylated hydroxyanisole, butylated hydroxytoluene, lecithin, propyl gallate, alpha-tocopherol, citric acid, ethylenediamine tetraacetic acid, sorbitol, tartaric acid, and phosphoric acid.

Examples of formulation additives include a thickening agent, for example beeswax, paraffin, or cetyl alcohol.

Examples of formulation excipients include a suspending excipient, sodium carboxymethylcellulose, methylcellulose, hydropropyl-methylcellulose, sodium alginate, polyvinylpyrrolidone, gum tragacanth, or gum acacia.

An ophthalmic formulation may include a preservative such as benzalkonium chloride, chlorobutanol, benzododecinium bromide, methyl paraben, propyl paraben, phenylethyl alcohol, edetate disodium, sorbic acid, polyquaternium-1, and hydroxybenzoate.

Examples of preservatives include sodium benzoate, phenol, cresol, p-chloro-m-cresol, benzyl alcohol, thimerosal, sorbic acid, and benzethonium chloride.

A unit dose composition can be sterile, but may not contain a preservative.

An ophthalmic formulation may include a pH adjusting excipient such as citric acid buffer, acetic acid buffer, succinic acid buffer, malic acid buffer, and gluconic acid buffer.

An ophthalmic formulation may include an additional acid such as hydrochloric acid, or and additional base, such as sodium hydroxide for pH adjustment.

Examples of pH control agents include arginine, sodium hydroxide, glycine, hydrochloric acid, and citric acid.

An ophthalmic formulation may include a buffer such as citric acid, ascorbic acid, gluconic acid, carbonic acid, tartaric acid, succinic acid, acetic acid, phthalic acid, tris, tromethamine hydrochloride, and phosphate buffer.

An ophthalmic formulation may include a surfactant.

Examples of a surfactant include nonionic surfactants, polysorbate-80, polysorbate-20, polysorbates, sorbitan esters, a lipid, a phospholipid, lecithin, a phosphatidylcholine, a phosphatidylethanolamine, a phosphatidylglycerol, a fatty acid, a fatty ester, a cholesterol.

Examples of surfactants include oleic acid, sorbitan trioleate, and long chain diglycerides.

Examples of surfactants include beractant, poractant alfa, and calfactant.

An ophthalmic formulation may include a tonicifier tonicity adjusting excipient.

Examples of a tonicity adjusting excipient, isotonizing excipient, include sodium chloride, mannitol, and sorbitol.

Examples of a tonicity adjusting excipient include sugars, polyols, amino acids, and organic and inorganic salts.

Embodiments of this invention include kits containing any of reagents, pharmaceutical excipients, active agents, and instructions for use.

A kit may include a container or formulation that contains one or more active agents formulated in a pharmaceutical preparation for delivery. An ophthalmic formulation kit can be a multidose form.

A kit may include a dispenser or dropping device for topical delivery and use.

A kit can include one or more unit doses of a composition for delivery. A unit dose can be hermetically sealed to preserve sterility.

Sample Preparation and Detection of Ultrastructural Target

Sample preparation and processing is described. Aqueous humor or vitreous humor specimens collected for EV isolation were processed immediately without fixation. EVs were isolated from bovine vitreous humor or aqueous humor; or 4T1 cells by using ultracentrifugation protocols described below. EVs were isolated using methods described. Patients aqueous humor was NOT isolated and imaged without processing. The samples were diluted as described.

Extracellular vesicle isolation and purification is described. We adapted methods for isolating extracellular vesicles from fluids. For bovine vitreous or aqueous humor, approximately 8 ml of vitreous (or 100 µl of aqueous humor) was placed in 15 ml tubes and centrifuged in Sorvall legend RT Swinging bucket (Sorvall) at 2,000 g (2500 rpm) at 4° C. for 30 minutes. The supernatant was then transferred to a new 15 ml tube. Then the centrifugation step was repeated. The supernatant was then transferred to new tube and centrifuged at 10,000 g in a Sorvall RC-58 centrifuge (Sorvall) using an SS-34 rotor (DuPont) for 30 min at 4° C. The supernatant was then transferred and the step was repeated. The sample was transferred to an ultracentrifuge tube (Beckman) and in a swinging bucket rotor (SW-41, Beckman) and centrifuged at 100,000 g in an L7-55 ultracentrifuge (Beckman) at 4° C. for 1 hour. The supernatant was transferred to a new tube. The step was repeated. Samples were resuspended in 50 μl of sterile tris buffered saline (TBS, pH 8) and placed in a siliconized tube. Samples for imaging were immediately processed, and remaining sample was frozen at −80° C.

Nanoparticle tracking analysis is described. The NanoSight NS300 system (Malvern) was used to perform nanoparticle tracking analysis to characterize particles from 30-800 nm in solution. We re-suspended extracellular vesicles isolated from vitreous humor, aqueous humor, or 4T1 cells in 100 μl of tris buffered saline (TBS, pH 7.0). Particles were loaded, the camera was focused, and 5 videos were captured for 60 sec each. Videos were recorded and then analyzed using NanoSight software (Version 3.0) to determine the size distribution and particle concentration of EVs. Graphs were created. The Brownian motion of each particle is tracked between frames, ultimately allowing calculation of the size through application of the Stokes-Einstein equation.

Conventional glutaraldehyde only fixation of liquid samples for electron microscopy is described. EV solutions that were processed with conventional TEM fixation methods are referred to as, "glutaraldehyde only," or "Glut only". EVs were obtained and resuspended in buffered solution as described above. We obtained Formvar/carbon-coated EM grids (Electron Microscopy Sciences) and coated the surface with Poly-L-lysine solution (%, Sigma Aldrich). We applied approximately 15 μl of poly-L-lysine to the formvar/carbon-coated surface of the EM grid and incubated the sample in a humidified chamber for 15 min at room temperature. We removed the poly-L-lysine solution with a pipette. We allowed the grid to dry for 10 minutes at room temperature.

Next, 5 μL of EV-containing solution was pipetted onto a poly-L-lysine-formvar/carbon-coated EM grid and incubated in a humidified chamber for 30 minutes at room temperature. Next, EV solution was removed with a pipette. The samples were fixed in a "glutaraldehyde fixation solution"; consisting of 2.5% glutaraldehyde, 4% paraformaldehyde, 0.02% picric acid in 0.1M sodium cacodylate buffer. We pipetted 15 μl of glutaraldehyde solution on the EM grid and incubated the sample for 15 min at room temperature19. After, the glutaraldehyde fixation solution was removed with a pipette. Grids were washed with 15 μl of double distilled water for 5 minutes at room temperature. Samples were washed 2 times for 5 min each at room temperature. Samples were dried at room temperature and viewed on a JEM 1400 electron microscope (JEOL, USA, Inc) as described below. EDC-formalin fixed specimens were processed further as described below.

EDC-ETT solution preparation is described. Methods for EDC solution fixation were adapted from previous reports17, 18. We prepared 0.1 M 1-Methylimidazole buffer solution (0.1 M 1-methylimidazole, 300 mM NaCl, with an adjusted pH to 8.0 with 12 N NaOH) and stored the solution for up to 3 months at room temperature. Next, we freshly prepared the EDC solution for each experiment. We measured 0.96 ml of 0.1 M 1-Methylimidazole buffer solution and added 13 mg of 5-(Ethylthio)-1H-tetrazole (ETT, Sigma Aldrich, final concentration was 0.1 M). The pH was adjusted to 8.0 with 12 N NaOH. Next, we added 19.2 mg of 1-ethyl-3-(3-dimethylaminopropyl) carbodiimide (EDC) (Sigma Aldrich, final concentration 0.10 M) and then readjusted the pH to 8.0 using 12 M HCl. The EDC-ETT solution was placed on ice until use.

EDC-glutaraldehyde fixation of liquid samples on electron microscopy is described. All isolated EVs were resuspended in 20 μl of TBS (pH 8.0) and kept at 4° C. We obtained Formvar/carbon-coated EM grids (Electron Microscopy Sciences) and coated the surface with Poly-L-lysine solution (%, Sigma Aldrich). We applied approximately 15 μl of poly-L-lysine to the formvar/carbon-coated surface of the EM grid and incubated the sample in a humidified chamber for 15 min at room temperature. We removed the poly-L-lysine solution with a pipette and set aside the grid in a humidified chamber until it is ready for use. Next, we combined equal parts of freshly made EDC/ETT solution and the EVs solution, by adding 5 μl of ice cold EDC/ETT solution with 5 μl of ice-cold EVs suspended in TBS (pH 8.0) into a 1.5 ml pre-chilled siliconized tube. The sample was incubated for 30 min on ice. We then applied 10 μl of the EDC/ETT-EV solution to the surface of the formvar/carbon-coated EM grids and incubated the sample for 30 min at 4° C. in a humidified chamber. In order too active the EDC regent's crosslinking capability, we placed the samples in a humidified chamber in an incubator for 3 h at 50° C. The samples were removed from the incubator and the EDC-solution was removed using a pipette. The samples were fixed with a secondary fixation using a glutaraldehyde-based crosslinking solution containing; 2.5% glutaraldehyde, 4% paraformaldehyde, 0.02% picric acid in 0.1M sodium cacodylate buffer and incubated for 15 min at room temperature. The glutaraldehyde solution was removed by pipetting the bubble from the EM grid. The grid was washed by placing 15 μl of double distilled water onto the grid and incubating for 5 minutes at room temperature. The water was removed and washed a second time. Finally, the samples were negatively stained or stained for DNA, RNA and protein as described below. For negative staining, the samples were contrasted successively in 2% uranyl acetate, pH 7, and 2% methylcellulose/0.4% uranyl acetate, pH 4. After staining with the respective stain(s), the EM grids were then mounted for imaging on the electron microscope as described below.

Transmission electron microscope imaging is described. All EM grids were viewed on a JEM 1400 electron microscope (JEOL, USA, Inc) operated at 100 kV. Digital images were captured on a Veleta 2K×2K CCD camera (Olympus-SIS). Electron microscopy images were recorded and analyzed for size and frequency of EVs using ImageJ software.

Transmission Electron microscopy of vitreous humor and ocular tissues is described. Human or bovine vitreous tissue was obtained as described above. Samples were cleared of cells with low speed centrifugation and whole mount specimens tested with H and E staining and imaging as described below. For vitreous, 2 μL was pipetted onto a block and fixed in a solution of 2.5% glutaraldehyde, 4% paraformaldehyde, 0.02% picric acid in 0.1M sodium cacodylate buffer and incubated for 60 min at room temperature19. Specimens were washed with excess volume of buffer (pH 7.3) for 5 minutes each at room temperature. Samples were post-fixed with 1% OsO4-1.5% K-ferricyanide (aqueous) for 60 min at room temperature20. Samples were washed with buffer 3 times for 5 min each at room temperature. Samples were set en bloc and stained with 1.5% uranyl acetate for 60 min at room temperature. Samples were dehydrated through graded ethanol series and transitioned through acetonitrile. Samples were infiltrated and embedded in Embed 812 resin (Electron Microscopy Sciences). Tissue sections were cut at 60-65 nm using a Diatome diamond knife (Diatome) on Leica Ultracut T ultramicrotome (Leica Microsystems). Sections were contrasted with lead citrate21 and viewed on a JEM 1400 electron microscope (JEOL, USA, Inc) operated at 100 kV. Digital images were captured on a Veleta 2K×2K CCD camera (Olympus-SIS). Electron microscopy images were recorded and analyzed for size and frequency of EVs using ImageJ software. For TEM staining of nucleic acids, we incubated Acridine Orange stain solution (Exo-Red Exosome RNA Fluorescent Label, System Biosciences) with 5 µl of ultracentrifuge purified EVs for 30 min at 25° C. For ethidium bromide (EtBr) stained EVs, we mixed 5 µg/ml of EtBr solution with 5 µl of ultracentrifuge purified EVs for 30 min at 25° C. For protein staining on TEM, we mixed 500 µM CFSE diluted in TBS (pH 7.4) with 5 µl of ultracentrifuge purified EVs for 30 min at 25° C. All samples above were then fixed, mounted, and imaged with TEM as above.

Statistical analyses are described. Graph visualization and calculations were performed using Excel (version 2011, Microsoft). All experiments, unless otherwise stated, were performed with n≥3. For nanoparticle tracking analysis we calculated particle size, concentration, and distribution using Stokes-Einstein equation. Statistical analyses were carried out using unpaired Student's t-test using SPSS software, and p values <0.05 were taken to be significant.

Methods for imaging healthy control aqueous humor samples and POAG aqueous humor samples are described. Samples are shown in Table 1.

TABLE 1

Reagents/Samples

| Experiment Sample number | Sample Name | Storage | Stain | Notes |
| --- | --- | --- | --- | --- |
| WCM1-8-1 | ME-2-1 | Cold Room | UA | 1:10 dilution (technical repeat) |
| WCM1-8-2 | ME-2-1 | Cold Room | AO | 1:10 dilution, -Label nucleic acids |

Methods:

For 1 mls of EDC/ETT solution in 0.1 M 1-Methylimidazole buffer (pH 8.0):
1. EDC-HCl powder should be stored at −20° C. under argon. To avoid condensation of humidity, only open bottles after they reached room temperature, i.e. take the bottle out of freezer 1 h before weighing out sample.
2. EDC/5-ETT solution should be made at most 1 h prior to use.
3. Pipette 5.76 ml of 0.1 M 1-Methylimidazole buffer (pH 8.0) into a 15 ml tube, vortex vigorously.
4. Carefully spoon out the 0.078 g of ETT found in the "G" group, onto a piece of paper. Carefully pour the 0.078 g into the tube.
5. Using the pH paper and pipet to check to be pH 8.0
6. Use a weighing paper to measure out 0.12 g of EDC. Carefully pour into the tube. Vortex vigorously.
7. Discard unused solution.
8. Using the pH paper and pipet to check to be pH 8.0

Poly L-lysine grids, EDC fixation, Glut-fixation, UA stain
1. Use formvar coated grids.
2. Place them facing formvar side down to poly-lysine drops and let them sit for 5-10 min.
3. Then you will withdraw the Poly-L-lysine
4. Fasten down a piece of parchment paper to a 100 mm dish with tape or weight. Place grid down on parchment paper. Mix EDC solution with EVs.
1. Mix 10 ul of (Cold) EVs with 10 ul of (Cold) EDC solution in 1.5 ml siliconized tube.
2. In the cold room, apply 10 µl sample (Aqueous humor) to the grid and wait 30 minutes to dry and for the EVs to settle to the bottom of the grid.
3. Place in a humidified chamber and incubate at 50 deg for at least 3 hours.

Secondary Fixation with Glut.
1. Remove EDC-EV solution from the sample using a pipette.
2. Fix with Glut, add 2-5 ul of glut fix and wait for 5 min
3. Remove Glut with Pipet or lens paper Rinse Glut and EDC
1. Apply water bubble to grid for 5 min
2. Remove water bubble with pipette
3. Add 5 ul of uranyl acetate onto grid (4 drops, blotting between each drop)
4. Let grid dry, and place in grid box
5. Take off stain with pipette Imaging with TEM. Image shortly after completion at 25 k (about 50 pictures) with few 50K magnifications.

Methods for treating POAG aqueous humor samples with bimatoprost, and fixation of fluid with EDC, negative staining and TEM imaging. We sought to determine the effect of bimatoprost on EVs in aqueous humor of patients with glaucoma. To do this, we diluted the POAG aqueous humor sample with tris buffered saline (1:10 dilution) and added 1:1 volume of diluted POAG sample with either tris buffered saline (control) or bimatoprost.

Lumigan was obtained directly from the dispensing bottle and was NOT diluted. 10 ul of POAG sample was mixed with 10 ul of TBS or 10 ul POAG sample was mixed with 10 ul of undiluted Lumigan. The tubes were then incubated in a thermocycler PCR machine and were allowed to sit for 72 hours at 37° C. The samples were then diluted (1:10). Next, we fixed with EDC on an electron microscopy grid using the following protocol.

For 1 mls of EDC/ETT solution in 0.1 M 1-Methylimidazole buffer (pH 8.0).
1. EDC-HCl powder should be stored at −20° C. under argon. To avoid condensation of humidity, only open bottles after they reached room temperature, i.e. take the bottle out of freezer 1 h before weighing out sample.
2. EDC/5-ETT solution should be made at most 1 h prior to use.
3. Pipette 5.76 ml of 0.1 M 1-Methylimidazole buffer (pH 8.0) into a 15 ml tube, vortex vigorously.
4. Carefully spoon out the 0.078 g of ETT found in the "G" group, onto a piece of paper. Carefully pour the 0.078 g into the tube.
5. Using the pH paper and pipet to check to be pH 8.0
6. Use a weighing paper to measure out 0.12 g of EDC. Carefully pour into the tube. Vortex vigorously.
7. Discard unused solution.
8. Using the pH paper and pipet to check to be pH 8.0

Poly L-lysine grids, EDC fixation, Glut-fixation, UA stain.
1. Use formvar coated grids.
2. Place them facing formvar side down to poly-lysine drops and let them sit for 5-10 min.
3. Then you will withdraw the Poly-L-lysine
4. Fasten down a piece of parchment paper to a 100 mm dish with tape or weight. Place grid down on parchment paper. Mix EDC solution with EVs
1. Mix 2.5 ul of (Cold) EVs with 5 ul of (Cold) EDC solution in 1.5 ml siliconized tube.
2. In the cold room, apply 5 µl sample (Aqueous humor) to the grid and wait 15 minutes to dry and for the EVs to settle to the bottom of the grid.
3. Place in a humidified chamber and incubate at 50 deg for at least 3 hours.

Secondary Fixation with Glut
1. Remove EDC-EV solution from the sample using a pipette.
2. Fix with Glut, add 2-5 ul of glut fix and wait for 5 min
3. Remove Glut with Pipet or lens paper
   Rinse Glut and EDC
1. Apply water bubble to grid for 5 min
2. Remove water bubble with pipette
3. Add 5 ul of uranyl acetate onto grid (1 drop, blotting after the drop)
4. Let grid dry, and place in grid box
5. Take off stain with pipette
   Samples were then imaged with TEM.

Additional embodiments of this invention are as follows.

A method of identifying glaucoma or pre-glaucoma in a subject, said method comprising: providing an aqueous humor sample from a subject potentially having glaucoma; analyzing the sample for glaucoma-associated-extracellular vesicle-complexes which are either: aggregates of extracellular vesicles, or individual extracellular vesicles having a diameter greater than 300 nanometers, or from 300 to 3,000 nm, or from 300 to 5,000 nm, or from 300 to 10,000 nm; and identifying, based on said analyzing, the subjects having glaucoma or pre-glaucoma.

The glaucoma-associated-extracellular vesicle complexes are complexes of extracellular vesicles selected from the group consisting of exomeres, exosomes, multivesicular bodies, intraluminal vesicles (ILVs), multivesicular endosomes (MVEs), oncosomes, micro-vesicles, apoptotic bodies, and vesicles originating from endosome or plasma membranes.

The glaucoma-associated extracellular vesicle complexes are complexes of individual extracellular vesicles, where the complexes may have a diameter of from 360 to 21,000 nanometers.

The glaucoma-associated extracellular vesicle complexes can be aggregates of 10, 20, 30, 40 or more extracellular vesicles.

The glaucoma-associated extracellular vesicle complexes can be aggregates of 50, 100 or 200 or more extracellular vesicles.

The method above, further comprising: fixing the glaucoma-associated extracellular vesicles in the sample prior to said analyzing. The fixing the glaucoma-associated extracellular vesicles comprises: contacting the sample with a non-reversible cross-linking agent; and contacting the sample with an aldehyde-containing fixative before, after, or at the same time as said contacting the sample with a non-reversible cross-linking agent to fix the glaucoma-associated-extracellular vesicle-complexes.

The method above, wherein the non-reversible cross-linking agent is selected from the group consisting of a water-soluble carbodiimide, cyanogen halide, and mixtures thereof.

The method above, wherein the non-reversible cross-linking agent is 1-ethyl-3-(3-dimethylaminopropyl)-carbodiimide.

The method above, wherein the non-reversible cross-linking agent is a cyanogen halide selected from the group consisting of cyanogen bromide, cyanogen fluoride, cyanogen chloride, and cyanogen iodide.

The method above, further comprising: contacting the sample with a further cross-linking agent, independently of, and before, after, or at the same time as said contacting with said non-reversible cross-linking agent and as said contacting with said aldehyde-containing fixative, said further cross-linking agent being selected from the group consisting of ethylene glycol di(meth)acrylate, ethylene glycol diacrylate, di(ethylene glycol) diacrylate, tetra(ethyleneglycol) diacrylate, ethylene glycol dimethacrylate, di(ethylene glycol) dimethacrylate, tri(ethylene glycol) dimethacrylate, derivatives of methylenebisacrylamide, N,N-methylenebisacrylamide, N,N-methylenebisacrylamide, N,N-(1,2-dihydroxyethylene)bisacrylamide, formaldehyde-free cross-linking agents, N-(1-hydroxy-2,2-dimethoxyethyl) acrylamide, divinylbenzene, formalin fixatives, formal calcium, formal saline, zinc formalin (unbuffered), Zenker's fixative, Helly's fixative, B-5 fixative. Bouin's solution. Hollande's solution, Gendre's solution. Clarke's solution, Camey's solution, methacam, alcoholic formalin, and formol acetic alcohol.

The method above, wherein said analyzing comprises: imaging the fixed glaucoma-associated-extracellular vesicle-complexes.

The method above, wherein said imaging is carried out by transmission electron microscopy, scanning electron microscopy, cryoelectron microscopy, binocular stereoscopic microscopy, wide-field microscopy, polarizing microscopy, phase contrast microscopy, multi-photon, microscopy, differential interference contrast microscopy, fluorescence microscopy, laser scanning confocal microscopy, multiphoton excitation microscopy, ray microscopy, ultrasonic microscopy, color metric assay, chemiluminescence assay, spectrophotometry, positron emission tomography, computerized tomography, and magnetic resonance imaging.

The method above, further comprising: detecting the glaucoma-associated-extracellular vesicle-complexes in the aqueous humor sample based on said imaging.

The method above, wherein said identifying is based on said detecting.

The method above, wherein said identifying comprises: providing a standard image of a clinical aqueous humor sample containing the glaucoma-associated-extracellular vesicle-complexes fixed with the non-reversible cross-linking agent and the aldehyde containing fixative, from a subject having glaucoma; comparing the image of the clinical sample of the subject to the standard image with regard to size, density, morphology, or spacial distribution of the fixed glaucoma-associated-extracellular vesicle-complexes; and determining if the subject has glaucoma or pre-glaucoma based on said comparing.

The method above, further comprising: administering a therapeutic agent to the subject based on said determining.

The method above, wherein the therapeutic agent reduces the size of glaucoma-associated extracellular-vesicle complexes by disrupting two or more extracellular vesicles that are in contact with each other.

The method above, wherein said identifying involves monitoring progression or regression of glaucoma and comprises: providing a prior image of a clinical aqueous humor sample of the subject, containing glaucoma-associated-extracellular vesicle-complexes fixed with a non-reversible cross-linking agent and the aldehyde containing fixative; comparing the image of the clinical aqueous humor sample of said subject containing the glaucoma-associated-extracellular vesicle-complexes fixed with the non-reversible cross-linking agent and the aldehyde containing fixative to the prior image with regard to size, density, morphology, or spacial distribution of the fixed glaucoma-associated-extracellular vesicle-complexes; and determining if the glaucoma is progressing or regressing based on said comparing.

The method above, wherein said identifying of glaucoma or pre-glaucoma is carried out before the subject providing the aqueous humor sample experiences any vision loss.

A method of screening compounds for their ability to treat glaucoma, said method comprising: providing candidate agents potentially useful in treating glaucoma; providing a sample containing glaucoma-associated extracellular vesicle-complexes, wherein the extracellular vesicles are either: aggregates of extracellular vesicles, or individual extracellular vesicles, having a diameter greater than 300 nanometers; contacting the candidate agents with the glaucoma-associated extracellular vesicle-complexes; and identifying candidate compounds which are effective in reducing the size of glaucoma-associated-extracellular vesicle-complexes based on said contacting.

The method above, wherein the glaucoma-associated extracellular vesicle-complexes are in aqueous humor.

The method above, further comprising: contacting a second sample containing the glaucoma-associated extracellular vesicle-complexes with a placebo and comparing size reduction of the glaucoma-associated extracellular vesicle-complexes of the samples contacted with the placebo versus that achieved with the candidate agent, to identify candidate compounds which are effective in reducing the size of glaucoma-associated-extracellular vesicle-complexes.

A reagent for detection of glaucoma comprising: an isolate sample comprising glaucoma-associated-extracellular vesicle-complexes which are either: aggregates of extracellular vesicles, or individual extracellular vesicles having a diameter over 300 nanometers.

The reagent above, wherein the glaucoma-associated extracellular vesicle-complexes are in aqueous humor.

All publications including patents, patent application publications, and non-patent publications referred to in this description are each expressly incorporated herein by reference in their entirety for all purposes.

Although the foregoing disclosure has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation. This invention includes all such additional embodiments, equivalents, and modifications. This invention includes any combinations or mixtures of the features, materials, elements, or limitations of the various illustrative components, examples, and claimed embodiments.

The terms "a," "an," "the," and similar terms describing the invention, and in the claims, are to be construed to include both the singular and the plural.

EXAMPLES

Example 1

Using improved fixation to enhance imaging of extracellular vesicles in biological fluids. EV ultrastructure in fluids can be detected with transmission electron microscopy (TEM) combined with negative staining. However, in our laboratory, we found that this technique led to inconsistent or often negative results. When examining known quantities of EVs applied to a solution, we observed a substantial discrepancy between the high number of EVs applied and the few EVs that were ultimately imaged. Often, the results were inconsistent and technical replicates would vary. Therefore, a methodological gap exists and hinders efficient, consistent and representative EV imaging in solutions. Therefore, we evaluated each step of the EV imaging protocol and attempted to identify points at which EVs may be lost. We found that conventional TEM protocols result in inefficient binding of EVs to the electron microscopy grid surface and that the majority of EVs fail to adhere. To more efficiently attach EVs, we crosslink with 1-ethyl-3-(3-dimethylaminopropyl) carbodiimide (EDC), which retains EVs and enables robust TEM imaging. Finally, we demonstrate that this method can be used to image EVs in a variety of biological fluids, including: blood (plasma); cerebrospinal fluid; nipple aspirate fluid; aqueous humor, or isolated EVs suspended in buffers.

Example 2

Figure 6:
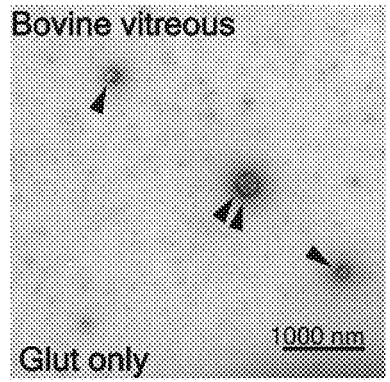
FIG. 6 shows imaging of extracellular vesicles with conventional fixation techniques result in inefficient EV imaging due to failure of EVs to adhere. Imaging is surprisingly improved using a non-reversible crosslinking reagent. (a) Representative photomicrographs of isolated bovine vitreous EVs, 4 million loaded, fixed to the copper grid with glutaraldehyde and subsequent UA and lead citrate solution, show few negatively stained EVs (arrowhead) at low (left) magnification, and in other photographs no EVs are visualized (middle and right). Negatively stained EVs are shown with signal (black) surrounding the perimeter of the EV and lower signal (white or grey) in the center. (b) Schematic diagram shows that EVs in solution that were applied to the electron microscopy grid surface fail to attach. The EVs are present in the discarded solution (black box) and we quantitated the size and number of EVs using nanoparticle tracking analysis (NTA). (c) NTA shows the size and concentration of EVs applied to the TEM grid surface. (d) NTA shows the size and concentration of EVs that were present in the discarded solution. This number represents the size and number of EVs that fail to adhere to the TEM grid surface. (g) Graphical representation comparing the amount of EVs applied to the electron microscopy grid surface (black bar) and the size and concentration of EVs present in the discarded solution (grey bars, n=3). (f) Representative TEM photomicrographs of isolated bovine vitreous EVs after EDC-glutaraldehyde-fixation, negative staining and TEM imaging reveal substantially more EVs visualized at low (left), medium (middle) and high (right) magnification. (g) Graphical representation (log 2) of the mean and ±standard deviation that shows significantly more EVs counted per image from EDC fixed specimens (350-fold), when compared to Glut fixed grids (n=3, counted on average seven images per biological replicate, *p<0.05). (h) Representative TEM photomicrographs of isolated bovine aqueous humor after EDC-glutaraldehyde-fixation show robust negative staining surrounding the border of the EV. (i) TEM images from human aqueous humor, without performing EV isolation, show multiple EVs present, in situ. Scale bars are (a) 1000 nm (left), 600 nm (middle), 125 nm (right); (f) 600 nm (left), 125 nm (right); (h) 500 nm; and (i) 1 μm.
Figure 6:
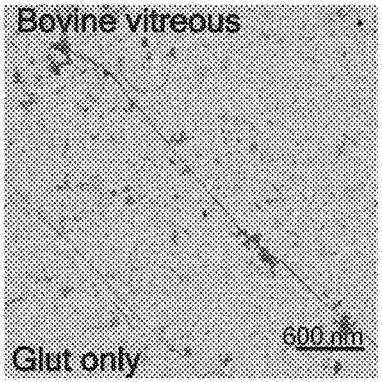
Figure 6:
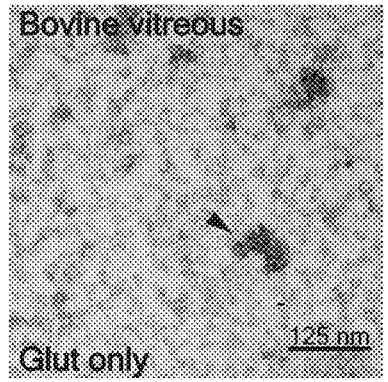
Figure 6:
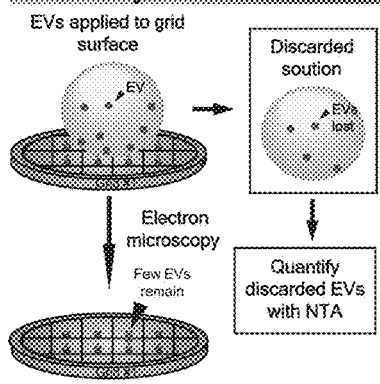
Figure 6:
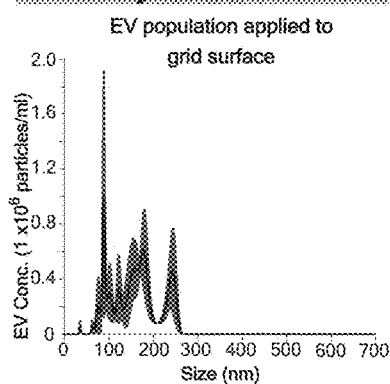
Figure 6:
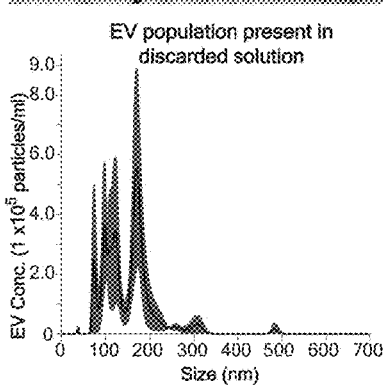
Figure 6:
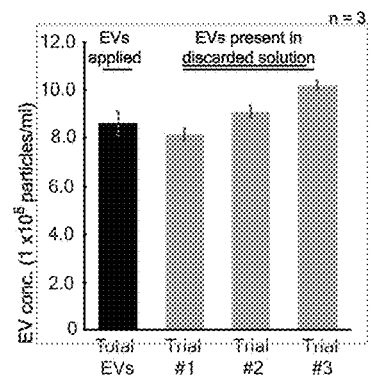
Figure 6:
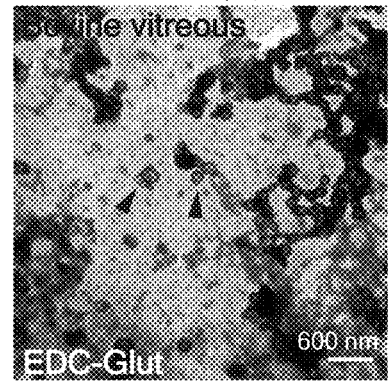
Figure 6:
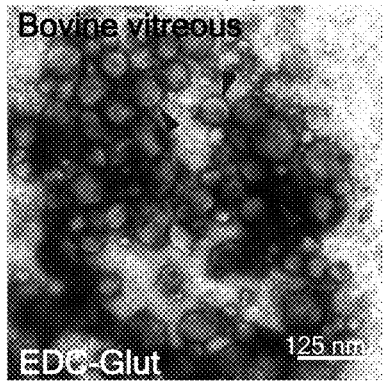
Figure 6:
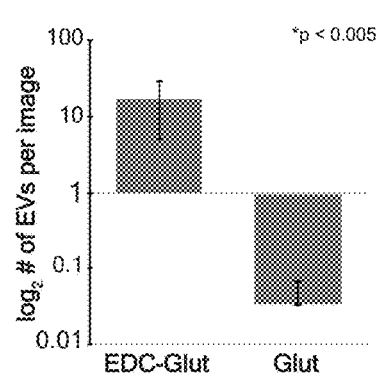
Figure 6:
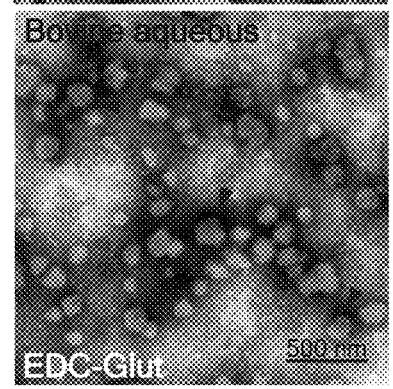
Figure 6:
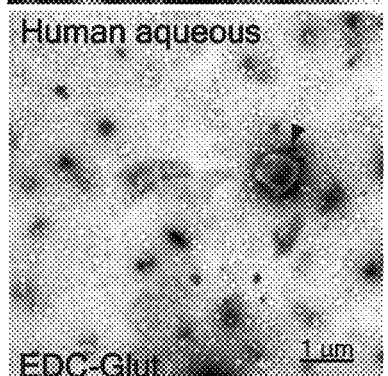

Imaging EVs suspended in liquids with conventional methods has a low yield due to massive loss of vesicles to the discarded solution. To improve established TEM and negative staining procedures, we used EVs isolated from the bovine vitreous humor (gel-like matrix, located between the lens and the retina of the eye) and aqueous as a model system. First, we dissected the vitreous humor from the posterior chamber of the eye, homogenized the sample, isolated EVs using ultracentrifugation, and re-suspended the sample in buffered saline. Next, we quantified the number and size of EVs using nanoparticle-tracking analysis (NTA; 3.98×108 EVs per ml). To visualize the ultrastructure of vitreous EVs suspended in a fluid, we followed conventional glutaraldehyde-based TEM imaging protocols (FIG. 6, top row). We applied approximately 4×106 EVs to an electron microscopy grid and followed standard protocols for glutaraldehyde fixation and negative staining with a uranyl acetate solution. We subsequently imaged the specimens using TEM and the results showed few EVs were present (0.033±0.182 EVs observed per 25,000× high-powered micrographic field, n=3 biological replicates, and 10 photos captured), which is an unexpectedly low number and incongruent with loading 4 million EVs. At low power, we observed sparsely spaced EVs (FIG. 6, top row, left) and in most photographic frames, we were unable to identify clearly negatively stained EVs (FIG. 6, top row, middle and right). These results suggest that EVs were either destroyed during specimen processing, failed to adhere to the surface of the TEM grid or were lost during the protocol. To verify that EVs were present in the vitreous specimen, we imaged the vitreous base, a tightly adherent section of the gel-like matrix attached to the retina, sectioned the sample, and prepared it for TEM. Indeed, we observed many EV shaped electron dense signals in vitreous tissue sections (data not shown), confirming that EVs should be present in our sample prepared for TEM. Therefore, we hypothesized that the millions of EVs applied to the surface of the electron microscopy grid were discarded in the cast off solution and not attached to the grid surface (FIG. 6, $2^{nd}$ row, left diagram). To determine if there were significant amounts of EVs present in the discarded solution, we measured and compared the number and size of EVs that were isolated from 4T1 breast cancer cell lines and re-suspended in a buffered saline. We found that the concentration of 4T1 EVs was 8.63×108 particles per ml (±4.96×108 particles per ml), and we applied 8.63×106 EVs to the grid surface (FIG. 6, $2^{nd}$ row, middle and Table 2). Next, we measured the amount of EVs present in the cast-off solution using nanoparticle tracking analysis (NTA) and found that in 3 separate trials, at least 8.16×108 particles per ml (±2.43×107 particles per ml) or 8.16×106 particles were lost to the wash buffer (FIG. 6, $2^{nd}$ row, right, FIG. 6, $3^{rd}$ row, left and Table 2). These data show that a majority of the EVs applied to the surface of the grid failed to adhere to the electron microscopy grid surface and were lost to the cast-off solution (FIG. 6, $3^{rd}$ row, left). Therefore, we have inferred that imaging EVs suspended in liquids using conventional fixation, negative staining and electron microscopy is severely hindered by poor cross-linking for EV to the grid surface.

Table 2 shows extracellular vesicles poorly adhere to electron microscopy grids. We determined the size and concentration of EVs that were applied over the grid surface and compared this value to the EVs present in the discarded fraction. We isolated EVs from mouse mammary tumor cell line, 4T1 cell media using ultracentrifugation methods and measurements were conducted using nanoparticle tracking analysis (NTA), using identical settings for all variables in NTA 2.3 build 17 software. The mean size, mode size and mean concentration of EVs applied over the TEM grid surface, and EVs present in the discarded fraction are shown (n=3).

TABLE 2

Extracellular vesicles and electron microscopy grids

| | Sample/vesicle type | | | | | |
|---|---|---|---|---|---|---|
| EVs isolated from media, mouse mammary tumor cell line (4T1) | Mean size (nm) | Standard error | Mode size (nm) | Standard error | Mean concentration E8 Particles/mL | SD |
| EVs applied to grid surface | 198.5 | +/−8.6 | 123.4 | +/−3.6 | 8.63e+08 | +/−4.96e+07 |
| EVs present in discarded solution, Trial #1 | 156.3 | +/−12.9 | 119.2 | +/−6.0 | 8.16e+08 | +/−2.43e+07 |
| EVs present in discarded solution, Trial #2 | 154.6 | +/−2.1 | 118.9 | +/−3.3 | 9.12e+08 | +/−2.54e+07 |
| EVs present in discarded solution, Trial #3 | 163.3 | +/−6.2 | 117.0 | +/−9.5 | 1.02e+09 | +/−1.95e+07 |

Samples were analyzed using NTA 3.1 build 54 software (Malvern).

Example 3

Using formalin-EDC fixation retains EVs and allows for robust imaging of EVs suspended in liquids. We assumed that EVs were poorly bound to the TEM grid and attempted to permanently adhere EVs suspended in a liquid on the grid by adding a heat stable fixative, EDC, a carbodiimide that creates a non-reversible crosslink between positively charged amino group side chains and carboxyl groups of proteins. To test our hypothesis, we combined 4 million isolated bovine vitreous EVs and EDC fixation solution, applied this to the surface of a poly-1-lysine coated formvar TEM grid, and activated the EDC solution by applying heat (50° C.) for 3 hr (FIG. 6, $3^{rd}$ row, middle). After crosslinking, we removed the EDC solution, applied glutaraldehyde fixation solution, washed the sample, and conducted negative staining. The images show an abundant number of EVs in each photographic frame with 16.5 EVs (±16.9) per 25,000× high-powered field under matching conditions of conventional negative staining and TEM imaging. Moreover, we identified at least 357-fold more EVs in EDC fixed samples, when compared to glutaraldehyde only (FIG. 6, $4^{th}$ row, left, p<0.05, n=3). To broaden the scope of this technique to other fluids, we visualized EVs isolated from bovine aqueous humor, which shows robust detection of EVs with electron dense negative stain surrounding the EV perimeter (FIG. 6, $4^{th}$ row, middle). We also imaged native aqueous humor fluid from a healthy patent to visualize the EVs in situ. We define in situ imaging as, "imaging a solution without EV isolation, and visualizing the contents of the biological fluid, in place." This is method of visualizing EVs is fluids differs from previous methods to images EVs, since we do not concentrate the EVs. Here, the images show a heterogeneous population of EVs with well-defined negative staining (FIG. 6, $4^{th}$ row, right). Overall, we found that cross-linking EVs suspended in multiple fluids with EDC resulted in substantial improvement transmission electron microscopy imaging. These data show that for imaging EVs in a fluid, EDC fixation significantly improves the number of EV observed, when compared to conventional aldehyde fixation.

Example 4

Comparing extracellular vesicles in the aqueous humor from healthy controls and patients with POAG. The aqueous humor is a transparent, water-like biological fluid that is like plasma, but contains 98% water, along with amino acids, electrolytes, ascorbic acid, glutathione, and immunoglobulins. Aqueous humor has been shown to contain EVs. In these studies, the EVs were isolated using ultracentrifugation protocols and they did not observe any glaucoma-associated-EV-aggregates. We hypothesized that there are differences in the EV ultrastructure of the aqueous in subjects with ocular pathology (such as glaucoma), as compared to healthy controls (subjects with no ocular pathology aside from cataracts). We choose to study the aqueous because it is normally lost during cataract surgery and obtaining the samples did not pose any additional risk to the subjects. To observe the most natural state of the aqueous humor, we did not isolate EVs using ultracentrifugation or other EV-related protocols. We collected aqueous humor from healthy patient cohorts and those with a clinical diagnosis of POAG. We predicted that EVs in glaucoma patients' aqueous humor shall be larger, thus allowing these structures to block the aqueous humor outflow. To complete this study, we obtained aqueous humor specimens from 1) healthy control patients undergoing elective cataract surgery (control cohort) or 2) from patients with a diagnosis of glaucoma (POAG cohort). The study design is listed below.

Example 5

Study design; obtaining aqueous humor from healthy and glaucoma patients. To determine the ultrastructure of EVs from aqueous humor donated by healthy controls or glaucoma patients, we conducted a prospective clinical trial.

Control samples were those with a diagnosis of cataracts, but no other ocular comorbidity, nor another systemic comorbidity. All patients in the control cohort were undergoing elective outpatient, ambulatory cataract surgery and were generally healthy. We collected a small sample (50 to 100 µl) of the aqueous (which would normally be lost as medical waste) at the beginning of the cataract surgery. We then fixed the samples with EDC crosslinking agent, negatively stain the samples, and performed transmission electron microscopy. Study samples will be those who in addition to the cataract also have POAG and none of the following conditions: diabetic retinopathy, or age-related macular degeneration. The pool of glaucoma patients will be chosen from patients who will have cataract extraction and lens implantation surgery. Inclusion criteria include the following; outpatient cataract surgery patients, age 18 years or older, who have either no ocular co-morbidities besides cataract, or who also have a documented clinical diagnosis of POAG. Exclusion criteria include ocular comorbidities, other than cataracts. An Institutional Review Board approved the protocol to collect samples and complete these studies.

Example 6

Obtaining aqueous humor samples from patients with and without glaucoma: During cataract surgery, incisions are made to enter the anterior chamber and access the cataractous lens. The aqueous egresses from the eye during the surgery and is replaced by irrigation solution infused through the instruments. We collected a small sample the aqueous, which would normally be lost as medical waste, at the beginning of the cataract surgery. The sample was assigned a numerical study ID code to de-identify it and transferred immediately from the OR to the laboratory for TEM imaging analysis. Patients did not undergo surgery or additional interventions for the purposes of this study, but were instead those individuals who were scheduled to undergo cataract surgery for therapeutic purposes. The cataract surgical schedule was reviewed to identify those patients that meet the inclusion and exclusion criteria delineated above, for control or POAG cohorts. Informed consent was obtained from each patient prior to inclusion in the study. Patients then underwent standard cataract surgery with the following exception. At the beginning of the cataract surgery a 30-gauge needle on a TB syringe was be inserted through the clear cornea to aspirate 0.05-0.1 cc of aqueous humor. The wound self-sealed. Subsequently, the corneal paracentesis incision was made as per standard cataract surgery as per the surgeon. We collected samples and transported the sample on ice to the laboratory. The study sample was identified a random study ID code to ensure it is de-identified. For all experiments, we did not isolate EVs using ultra-centrifugation methods, rather imaged the biological fluid in situ.

Example 7

Figure 7:
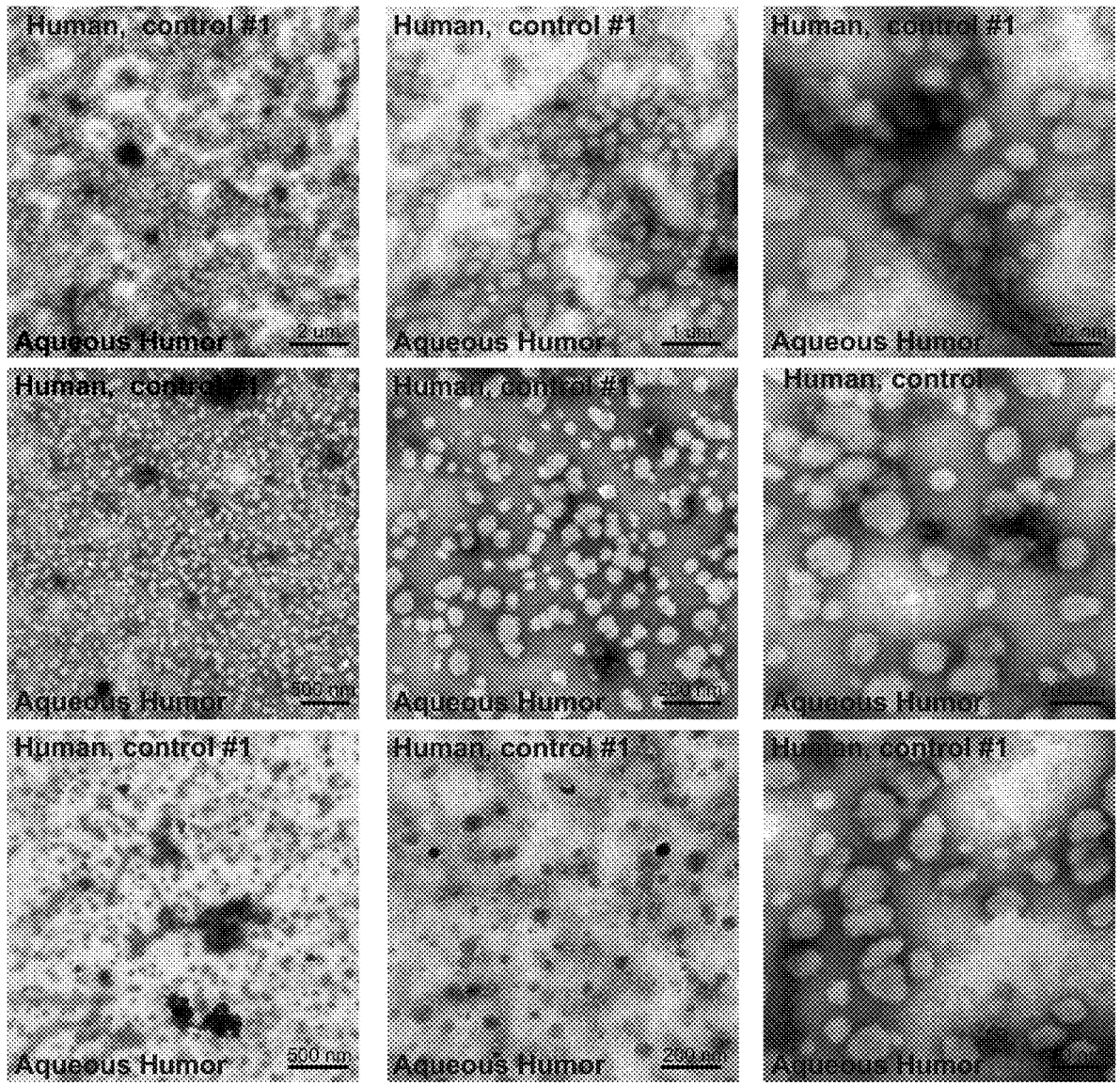
FIG. 7 shows healthy human aqueous humor, control, Patient #1, shows a diffuse distribution of non-aggregated EVs. (a-c) Representative photomicrographs of diluted human healthy control aqueous humor EVs (EVs were NOT isolated with ultracentrifugation, only diluted with buffered saline), fixed to the copper grid with EDC, glutaraldehyde and subsequently stained with UA solution. Photographs were captured with transmission electron microscopy and recorded. The images show many negatively stained EVs of various sizes, and the majority of EVs exist in the fluid independent without aggregation. One EV-aggregate was observed and was in the minority of samples imaged. Scale bars are marked on the photographs.
Figure 8:
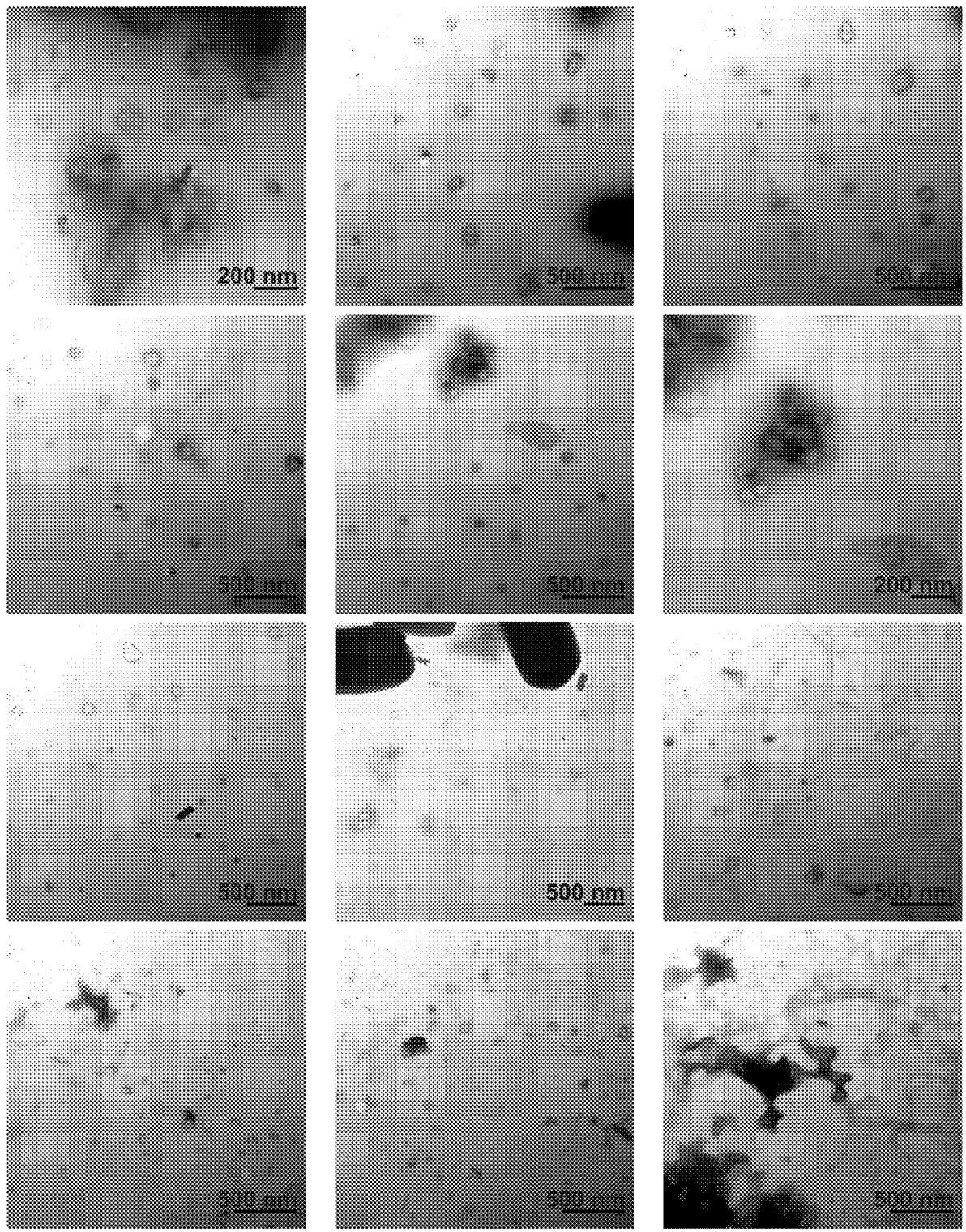
FIG. 8 shows healthy human aqueous humor, control, Patient #2, shows a diffuse distribution of non-aggregated EVs. (a-d) Representative photomicrographs of diluted human healthy control aqueous humor EVs (EVs were NOT isolated with ultracentrifugation, only diluted with buffered saline), fixed to the copper grid with EDC, glutaraldehyde and subsequently stained with UA solution. Photographs were captured with transmission electron microscopy and recorded. The images show many negatively stained EVs of various sizes. No EV-aggregates larger than 2 μm were observed, nor were large clumps of EVs visualized. Scale bars are marked on the photographs.

Imaging the ultrastructure of healthy control aqueous humor in situ shows a diffuse distribution of EVs: To understand the morphology of EVs in the normal physiological state, we imaged healthy patients aqueous humor in situ. No prior glaucoma studies have used the EDC fixation to visualize EVs in aqueous humor in situ. To understand the ultrastructural content of aqueous humor, we diluted the sample 1:10 with buffered saline (note: we did not isolate EVs), fixed the sample with EDC, then glutaraldehyde, negatively stained the specimen, and imaged with TEM. The data showed that healthy human aqueous humor contains an abundant number of EVs from multiple control human subjects (FIG. 7-8). These studies suggest that EVs in healthy human aqueous humor are present, diffusely distributed and there is no evidence of aggregating of the EVs. Moreover, most EVs were not attached to another and had a relatively even distribution. Therefore, healthy control aqueous humor contains EVs that are non-aggregated and diffuse distribution.

Example 8

Figure 9:
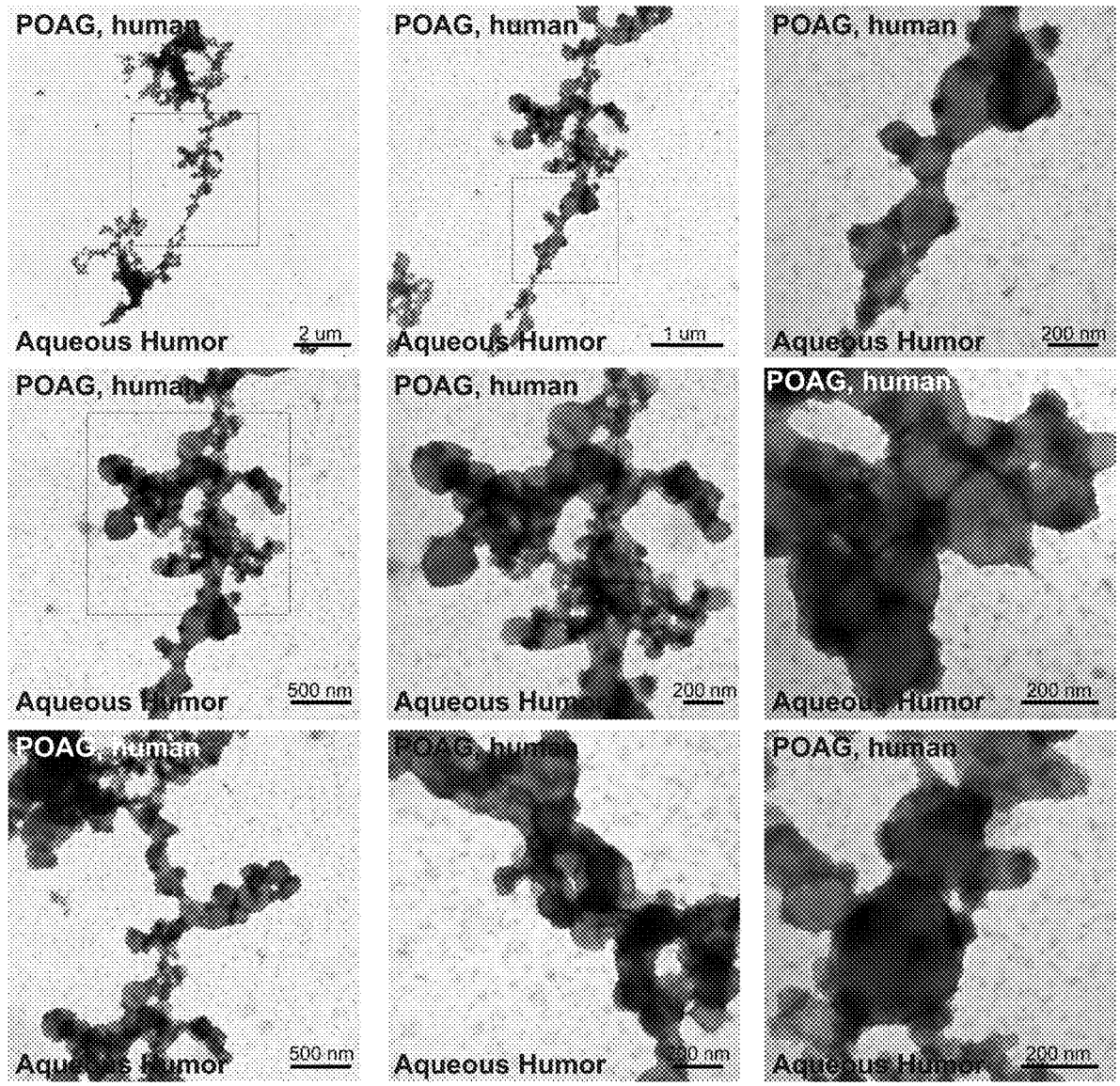
FIG. 9 shows POAG aqueous humor and shows large glaucoma-associated-EV-aggregates in Patient #1. (a-c) Representative transmission electron microscopy photographs show POAG aqueous humor samples (EVs were NOT isolated with ultracentrifugation, only diluted with buffered saline), fixed to the copper grid with EDC, glutaraldehyde and subsequently stained with UA solution. Photographs were captured with transmission electron microscopy and recorded. The diluted POAG specimens show evidence of glaucoma-associated-EV-aggregates present in the fluid that are large in size. Images show few free EVs observed (a-c). Scale bars are marked on the photographs.
Figure 10:
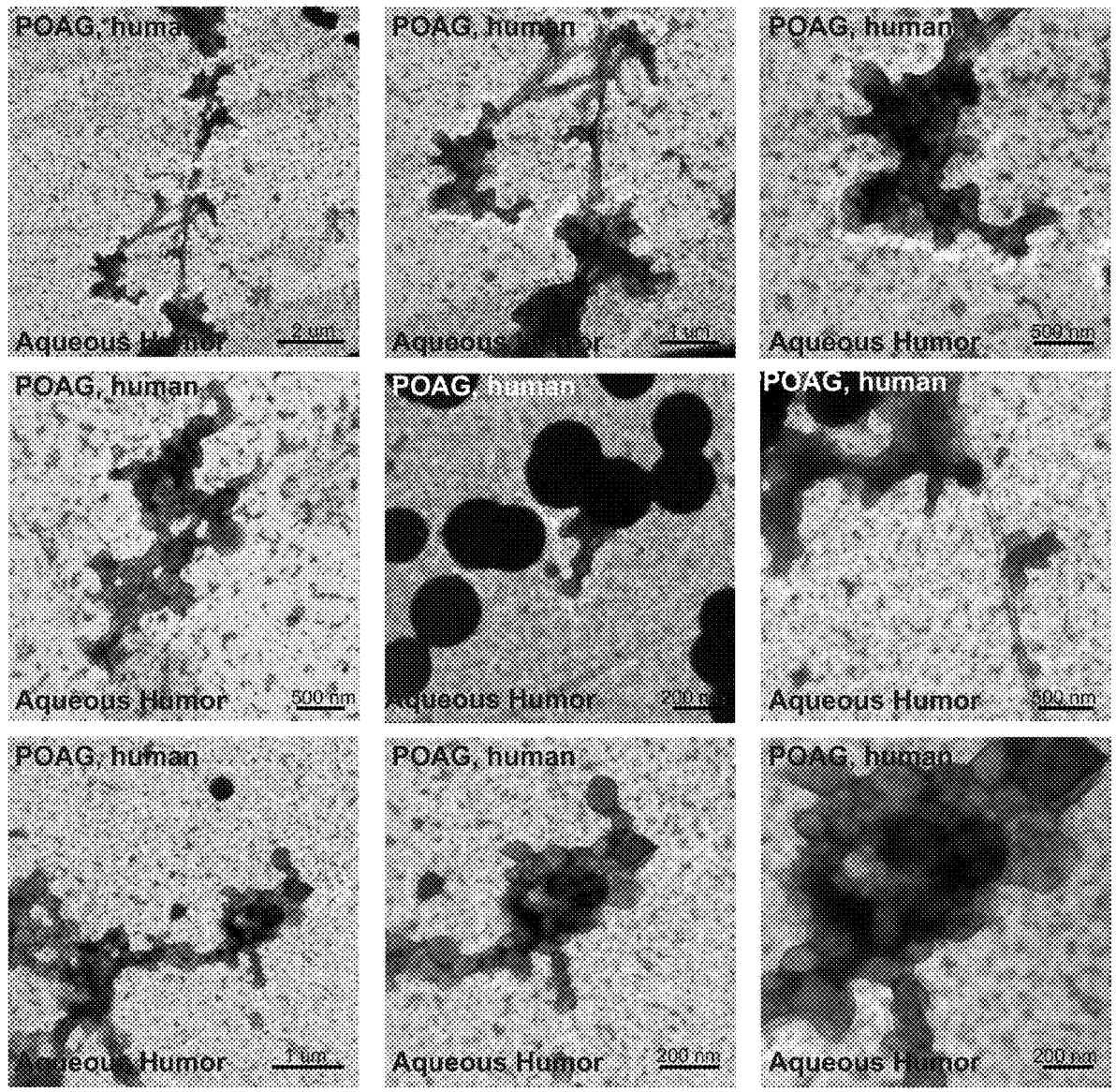
FIG. 10 shows POAG aqueous humor and shows large glaucoma-associated-EV-aggregates in Patient #2. (a-c) Representative transmission electron microscopy photographs from a second POAG sample (EVs were NOT isolated with ultracentrifugation, only diluted with buffered saline), fixed to the copper grid with EDC, glutaraldehyde and subsequently stained with UA solution. Photographs were captured with transmission electron microscopy and recorded. The second POAG aqueous humor specimens show evidence of sizeable glaucoma-associated-EV-aggregates and larger free EVs. Scale bars are marked on the photographs.

Imaging the ultrastructure of POAG aqueous humor in situ shows a sizeable glaucoma-associated-EV-complex that is larger than EVs observed in healthy controls. We hypothesized that POAG patients have a previously unidentified material present in the aqueous humor that is responsible for blocking the trabecular meshwork. We hypothesize that this unidentified material has yet to be described, because it has been below the threshold of detection using current imaging technology. Therefore, we applied EDC fixation, negative staining, and transmission electron microscopy imaging to observe the morphology of EVs in the aqueous humor of a POAG patient. The aqueous humor imaged from two different POAG patients was imaged in situ, without processing (no EV isolation), under identical conditions that were used for healthy controls. Surprisingly, the aqueous humor of patients with POAG showed numerous groups of EVs aggregated together in large EV-complexes, which are several microns in size, which we term "glaucoma-associated-EV-complex" (FIG. 9 and FIG. 10). The glaucoma-associated-EV-complex was present is two different patient samples and measure larger than the opening of the JCT (1 to 4 µm, or up to 2 to 20 µm), which is large enough to block the juxtacanalicular tissue. These data suggest that patients with POAG have an ultrastructural material present in the aqueous humor that could be responsible for blocking the trabecular meshwork, reducing aqueous outflow, and potentially causing vision loss. We propose that the glaucoma-associated-EV-complex is the unidentified material that contributes to the pathology of glaucoma.

Example 9

Figure 11:
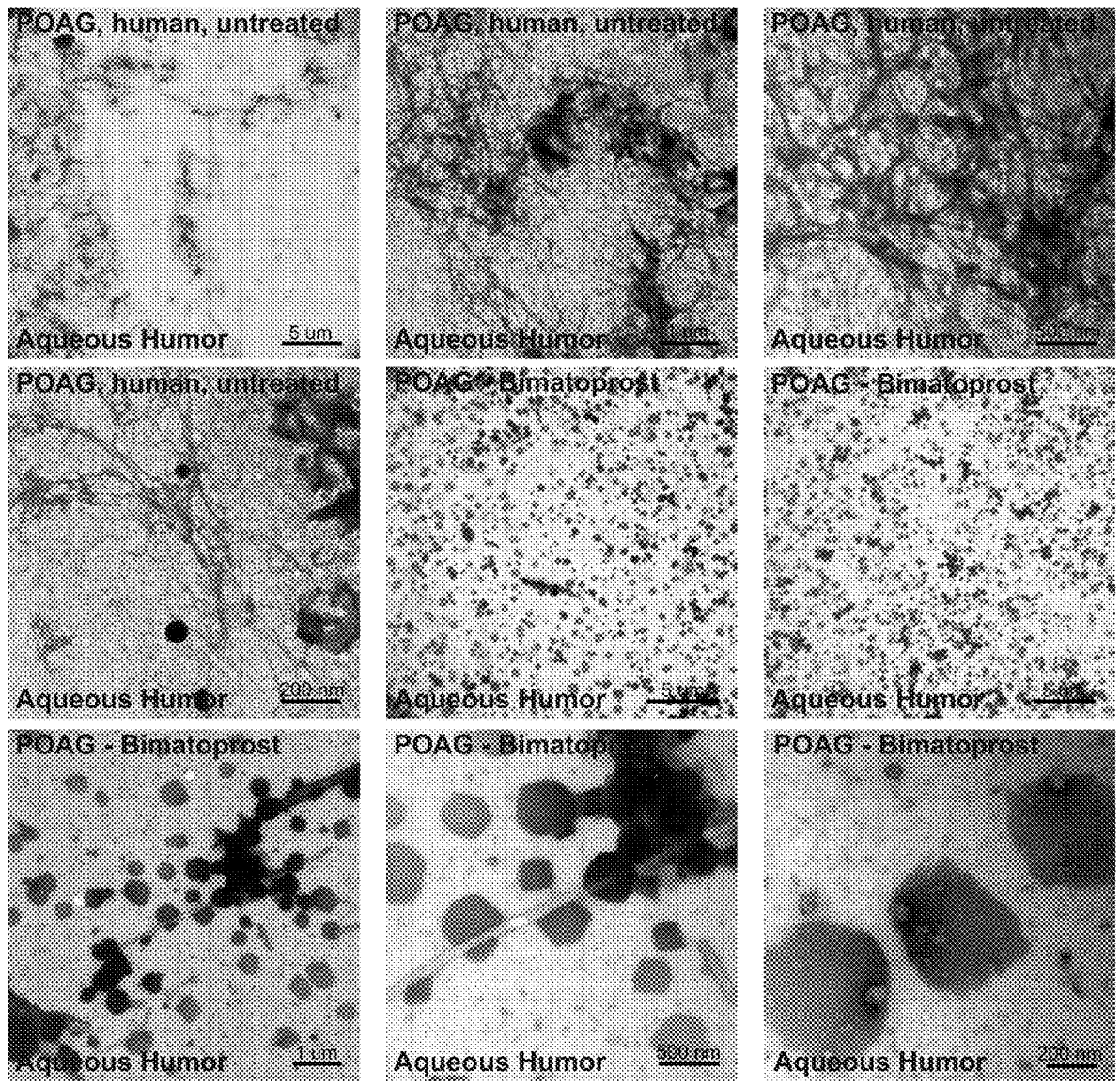
FIG. 11 shows a known glaucoma treatment, bimatoprost, reduces the size of POAG-associated EV complexes in the aqueous humor of a patient with glaucoma, when compared to untreated glaucoma samples. (a-b) Representative transmission electron microscopy photographs show human aqueous humor collected from a patient with POAG and no treatment (placebo, control, buffered saline) shows evidence of extracellular matrix and glaucoma associated-EV-complexes in the aqueous humor. Images show large collagen-like matrix in all panels and these electron dense structures measure several microns in size. (c-d) Representative photographs show POAG aqueous humor samples treated with a glaucoma medication, bimatoprost, and show no evidence of large extracellular matrix nor glaucoma-associated-EV-aggregates. On high power imaging, there appears to be larger globules that are not aggregated. Scale bars are marked on the figures.
Figure 12:
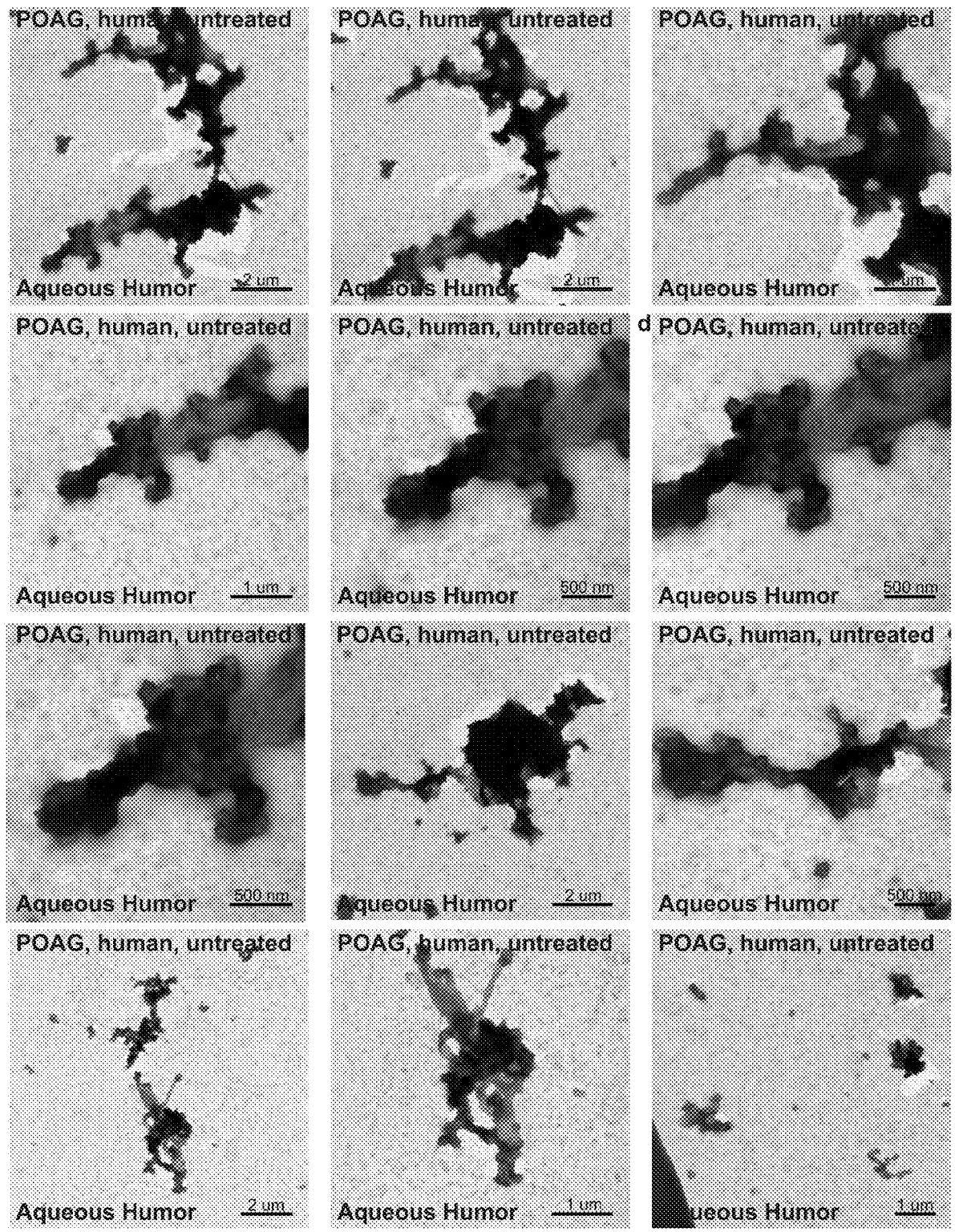
FIG. 12 shows treatment of a glaucoma patient's aqueous humor with buffered saline has no effect on POAG-associated EV complexes of a second subject diagnosed with glaucoma.
Figure 13:
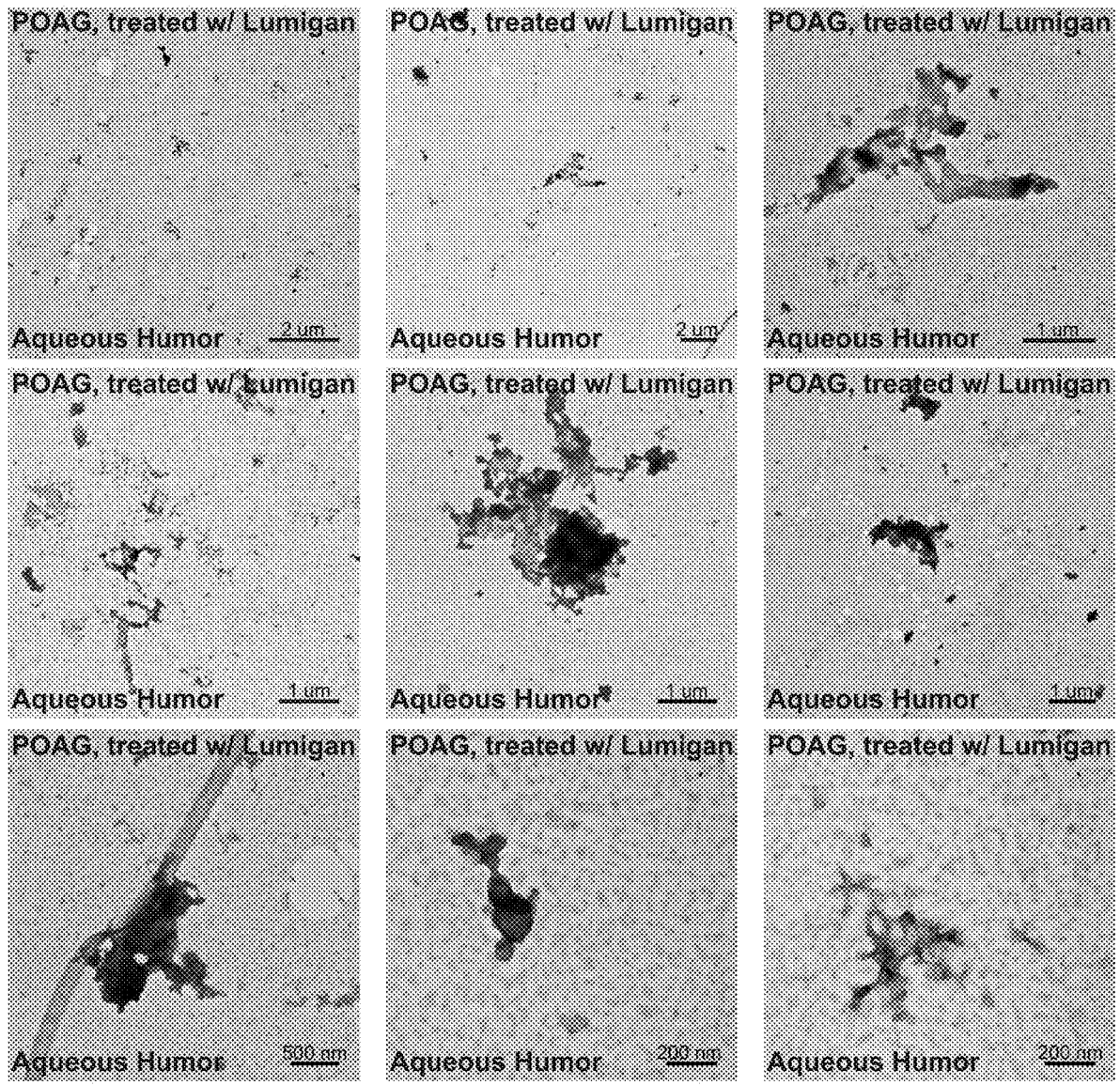
FIG. 13 shows bimatoprost reduces the size of POAG-associated EV complexes in the aqueous humor of a second subject diagnosed with glaucoma, when compared to control-treated glaucoma samples.

Treating large EV complexes with Bimatoprost breaks up the EV-complex, when compared to controls. To determine if glaucoma-associated-EV-aggregates visualized using the EDC fixation method were indeed a potential mediator of POAG, we hypothesized that treating it with a known glaucoma medication would change the morphology of the glaucoma-associated-EV-aggregates. Therefore, we opted to use Bimatoprost (lumigan), which is a ocular hypotensive agent that lowers IOP in normal, ocular hypertensive, and glaucomatous eyes. Moreover, bimatoprost is known to enhance the outflow of aqueous humor by remodeling the extracellular matrix, via regulation of matrix metallo-proteinases and remodeling of extracellular matrix. Here, we hypothesized that the glaucoma-associated-EV-complex would be reduced in size by the addition of bimatoprost. To test this, we incubated a POAG patient's aqueous humor with bimatoprost or buffered saline (placebo or control condition) at 37° C. for 72 hours, and imaged the EV ultrastructure using EDC fixation, negative staining and transmission electron microscopy (FIG. 11-13). After bimatoprost treatment, we noted a substantial reduction in the number of glaucoma-associated-EV-complex in the POAG-bimatoprost sample, when compared to POAG sample with placebo treatment (FIG. 11). In a second human subject with a diagnosis of glaucoma, repeated the experiment and mixed POAG aqueous humor with placebo (buffered saline), incubated the sample at 37° C. for 72 hours and we observed many glaucoma-associated-EV-complexes (FIG. 12). However, under identical conditions, except we used bimatoprost, we observed a substantial reduction in the number of glaucoma-associated-EV-complexes (FIG. 13). These data suggest that a known treatment for POAG reduces size and alters the morphology of the glaucoma-associated-EV-complex, suggesting that this complex may be a potential pathological mediator of POAG.

Example 10

Figure 14:
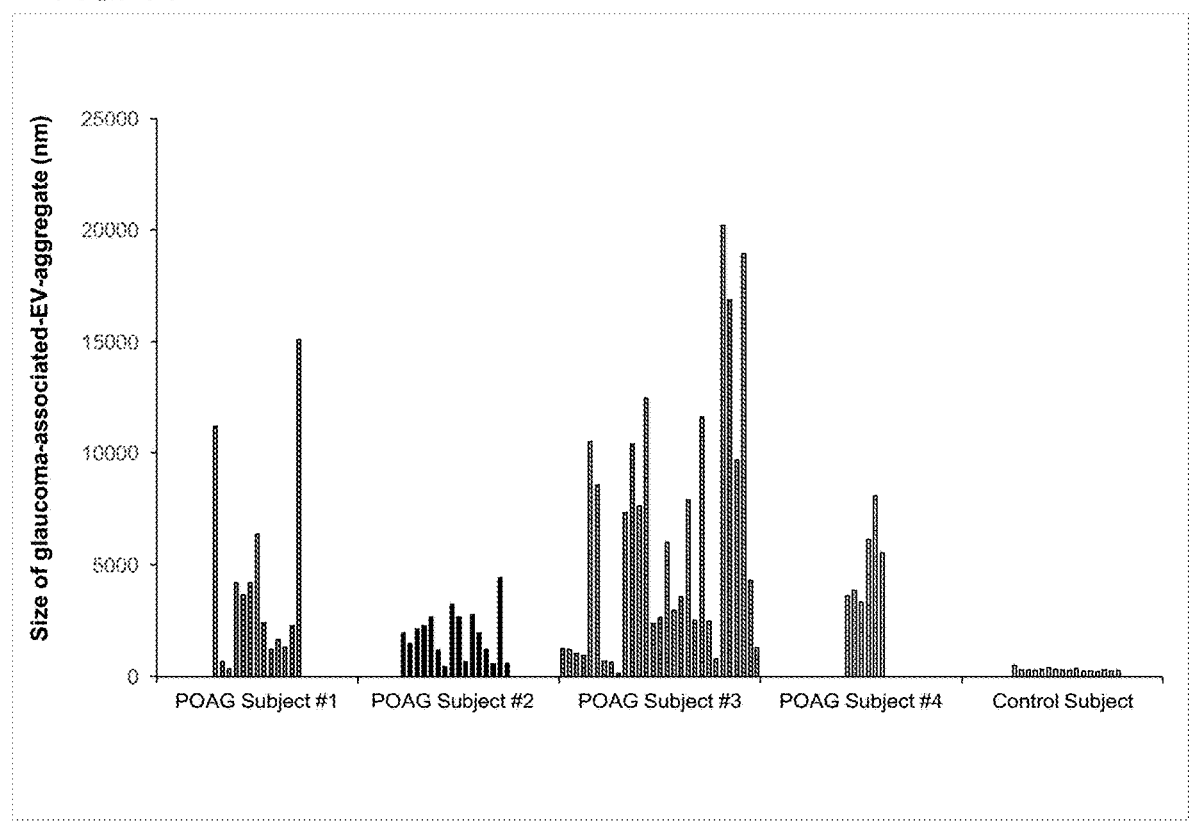
FIG. 14 shows glaucoma patients' aqueous humor contains larger electron dense structures in the aqueous humor that are not present in healthy controls. Graphical representation that depicts the size and number of an unidentified material that we termed, "glaucoma-associated-EV-aggregates" in healthy controls or POAG specimens. We obtained healthy control or POAG human aqueous humor, fixed the samples with EDC, and imaged the specimens with transmission electron microscopy. Photographs were analyzed and the number of glaucoma-associated-EV-aggregates were identified and plotted for each variable. In aqueous humor obtained from a single healthy control subject, the data shows that most EVs did not have glaucoma-associated-EV-aggregates. The data show that three subjects with a diagnosis of POAG had numerous glaucoma-associated-EV-aggregates that are several micrometers in size. Theses aggregates were not observed in healthy controls. The graph shows a substantial difference in the size of the glaucoma-associated-EV-aggregates in POAG, when compared to healthy controls.

Glaucoma patients' aqueous humor contains larger electron dense structures in the aqueous humor that are not present in healthy controls. The electron microscopy images showed large electron dense structure in the POAG specimen aqueous humor that were not present in the healthy controls. We hypothesized that the POAG glaucoma-associated-EV-aggregates were larger in size and present in higher numbers when compared to healthy controls. Therefore, we obtained the electron microscopy photographs from healthy controls or POAG samples and measured the number and size of glaucoma-associated-EV-aggregates. The data showed that POAG aqueous humor has substantially larger glaucoma-associated-EV-aggregates that measure from 361 nm to 20,214 nm (FIG. 14). Moreover, we observed substantially more glaucoma-associated-EV-aggregates in the POAG samples when compared to healthy controls. These data suggest that POAG aqueous humor EVs contain a large ultrastructural complex that is not present in healthy controls (FIG. 14). Moreover, the glaucoma-associated-EV-aggregates are large enough to block the drainage system of the eye, the trabecular meshwork. It has been postulated that abnormal aqueous humor outflow causes elevated IOP, which is a major risk factor for glaucoma. The region of the TM implicated in establishing IOP is next to Schlemm's canal and is called the juxtacanalicular tissue (JCT) or cribriform region. The site of most resistance to the aqueous outflow is the JCT, and it measures approximately 2-20 µm (J. Ocular Biology 2013 Jun. 1(1):3), with fenestrations of 1 to 4 µm or larger. JCT is composed of the loosely arranged extracellular matrix (ECM) into which cells are embedded. ECM of JCT has been implicated as a barrier that may isolate the ocular fluid outflow. Therefore, we hypothesize that this material (glaucoma-associated-EV-aggregate) in the aqueous humor of patients with glaucoma, that is physically larger than the diameter of the JCT outlet, may block the aqueous outflow and be related to glaucoma pathology.

Example 11

Figure 15:
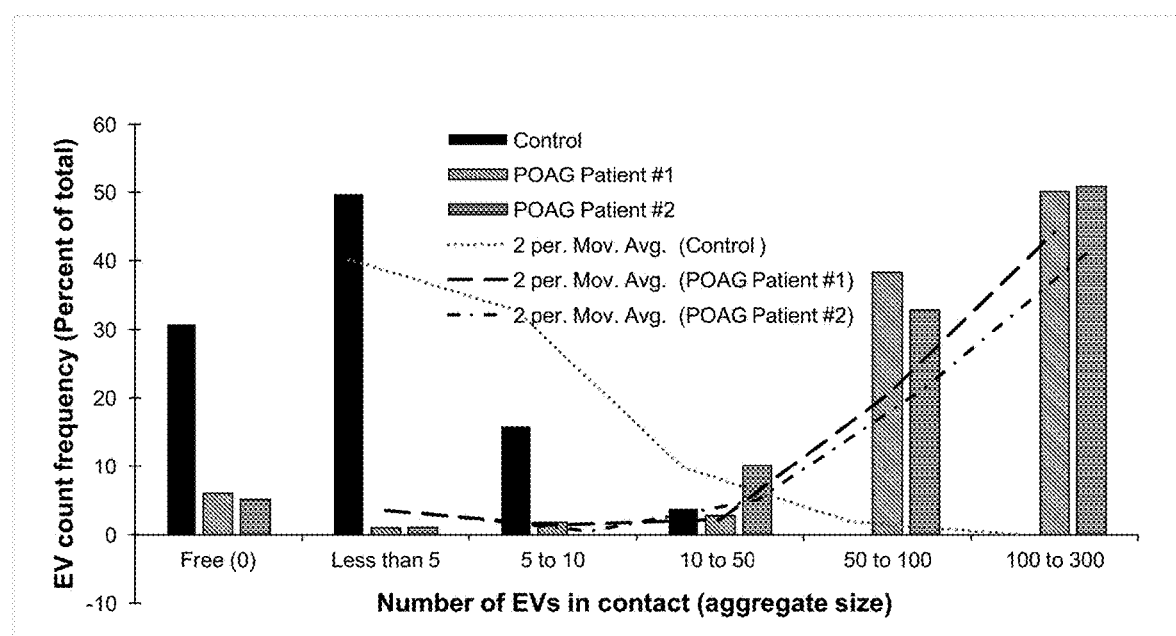
FIG. 15 shows glaucoma patients' aqueous humor contains EVs that aggregate and contact each other, when compared to healthy controls that have fewer EVs touching each other. Graphical representation that depicts the number of EVs that are in contact with each other (X-axis) and the count frequency (percent of total). We obtained healthy control or POAG human aqueous humor, fixed the samples with EDC, and imaged the specimens with transmission electron microscopy. Photographs were analyzed and the number of EVs contacting each other as determined for each variable. In aqueous humor obtained from a single healthy control subject, the data shows that most EVs are free and not present in aggregates. The data shows that two subjects with a diagnosis of POAG have aqueous humor that contains EVs that contact a large number of other EVs. The graph shows a substantial difference between the number of EVs contacting each other in POAG, when compared to healthy controls.
Figure 16:
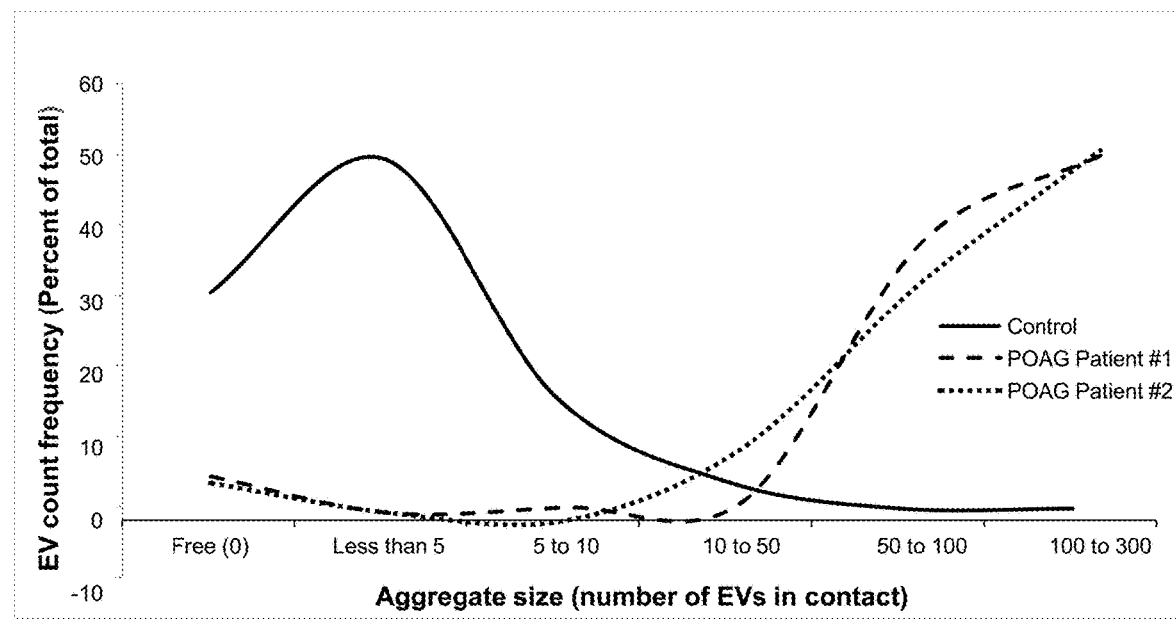
FIG. 16 shows a curvilinear chart of the data in FIG. 15. Glaucoma patients' aqueous humor contains EVs that aggregate and contact each other, when compared to healthy controls that have fewer EVs touching each other.

Glaucoma patients' aqueous humor contains EVs that contact each other that form larger structures called, "glaucoma-associated-EV-aggregates", that are not present in healthy control aqueous humor. To determine the composition of the glaucoma-associated-EV-aggregates we analyzed the TEM images and found that these ultra-structures are composed of many EVs contacting each other to form larger aggregates. To quantify the number of EVs found within the glaucoma-associated-EV-aggregates, we counted the total number of EVs present in the image, quantified the number of EVs in each aggregate, or calculated the number of EVs that were not contacting another EV (Free EVs). We classified the number of EVs contacting each other from 0 (free EVs, without contact), less than 5 EVs contacting each other, 5 to 10 EVs contacting each other, 10 to 50 EVs contacting each other, 50 to 100 EVs contacting each other, or 100 to 300 EVs contacting each other. The data showed that in healthy controls, few EVs were found in aggregates (FIG. 15 and FIG. 16), with most EVs contacting less than 5 other EVs. The data suggest that in healthy controls most EVs are "free EVs." Interestingly, for patients with glaucoma, a substantial amount of EVs contacted between 50 to 300 other EVs. The data suggests that most EVs in glaucoma are found within the glaucoma-associated-EV-aggregate, more than the healthy control sample (FIG. 15 and FIG. 16). These data suggest that patients with glaucoma have EVs that contact each other, in stark contrast to healthy controls, in which the majority of EVs are free.

Example 12

Figure 17:
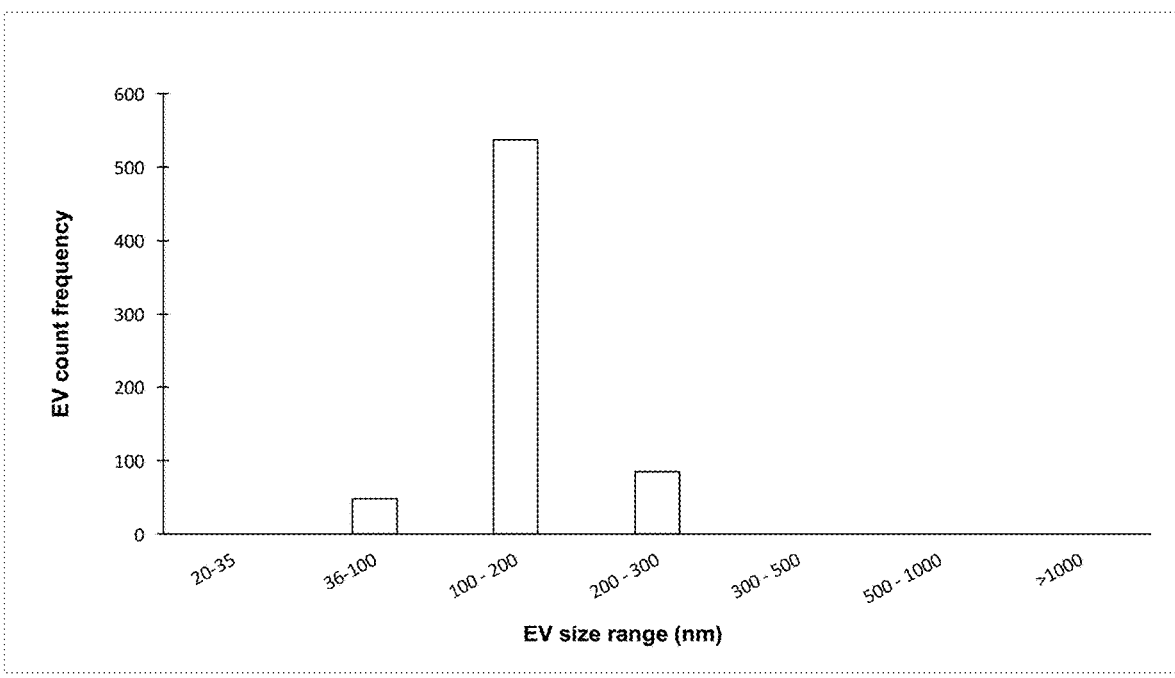
FIG. 17 shows extracellular vesicles are present in human aqueous humor obtained from healthy control patients and have a dominant population of EVs between 100 to 200 nm. Graphical representation that depicts the EV population in human aqueous humor obtained from a single healthy control patient. The EV count frequency is shown as a function of size. We fixed healthy control human aqueous humor after measuring EVs diameter after fixing human aqueous humor from a healthy control that was fixed with EDC fixation and imaged with transmission electron microscopy. The data shows that healthy control human aqueous humor contains EVs. The majority of EVs between 100-200 nm in diameter for this patient. All EVs that were visualized were free from contact with other EVs (not aggregated).

Extracellular vesicles in the aqueous humor of healthy control subjects exist as "Free-EVs" and with a majority of EVs between 100 to 200 nm in size. We sought to determine and quantify the EV population in healthy controls aqueous humor. To determine the size distribution of EVs in healthy control aqueous humor, we characterized the EV population in human aqueous humor obtained from a single healthy control patient (FIG. 17). We fixed healthy control human aqueous humor using EDC, negatively stained the sample and imaged with TEM. We analyzed the photographs and measured the EVs diameter. The data shows that healthy control human aqueous humor contains EVs with a majority of EVs between 100-200 nm in diameter for this patient (FIG. 17). Furthermore, we observed that most EVs in the control cohort were free from contact from other EVs. This data suggests that healthy control aqueous humor contain exosomes and some microvesicles. We did not observe larger apoptotic bodies in these samples, nor glaucoma-associated-EV-aggregates.

Example 13

Figure 18:
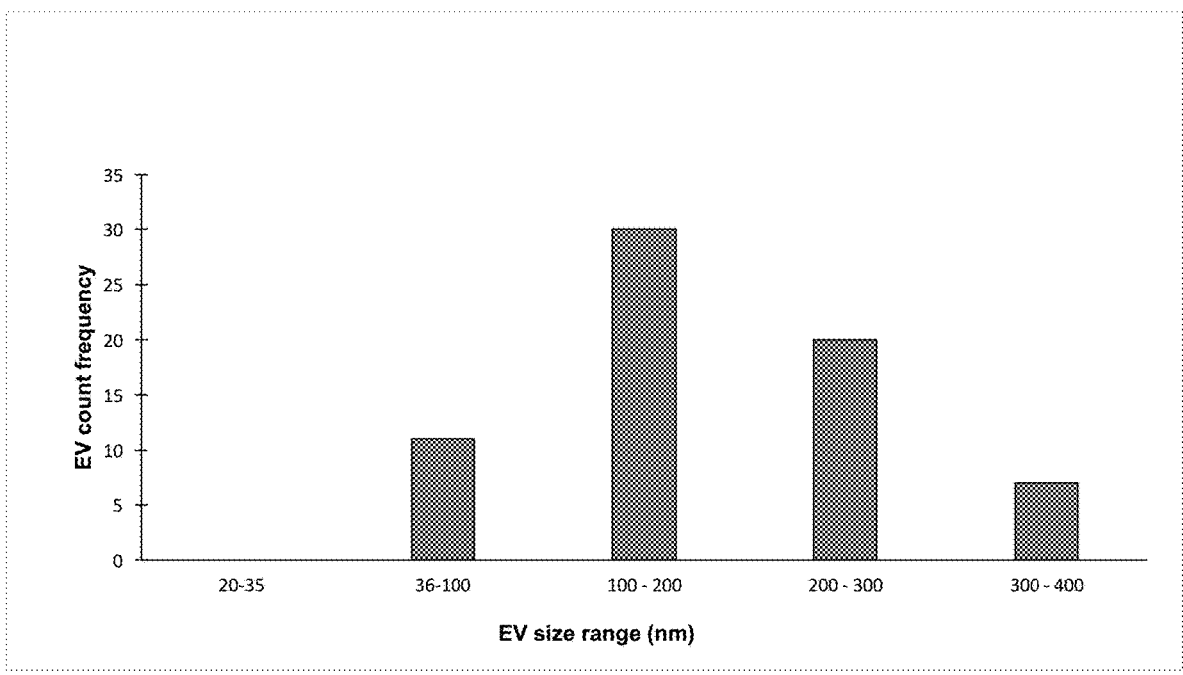
FIG. 18 shows extracellular vesicles in the aqueous humor of subject #1 with the diagnosis of POAG are located within the "glaucoma-associated-EV-aggregates," shows all EVs located within the glaucoma-associated-EV-aggregate. (a) Graphical representation of the EV population in human aqueous humor obtained from subject #1 with the diagnosis of POAG. We fixed the aqueous humor with EDC fixation and imaged with transmission electron microscopy. The photographs were analyzed and EV size and number were quantitated and graphed. We observed that EVs were present within an aggregate (defined as EVs that contact each other or glaucoma-associated-EV-aggregate). The data show the number and size of individual EVs present within the glaucoma-associated-EV-aggregate (gray bar) as a function of the total number EVs counted. A substantial number of EVs are between 36 nm and 300 nm with a high number of EVs 100-200 nm in size. In Subject #1's aqueous humor, we did not observe free EVs (EVs that do not contact each other).
Figure 19:
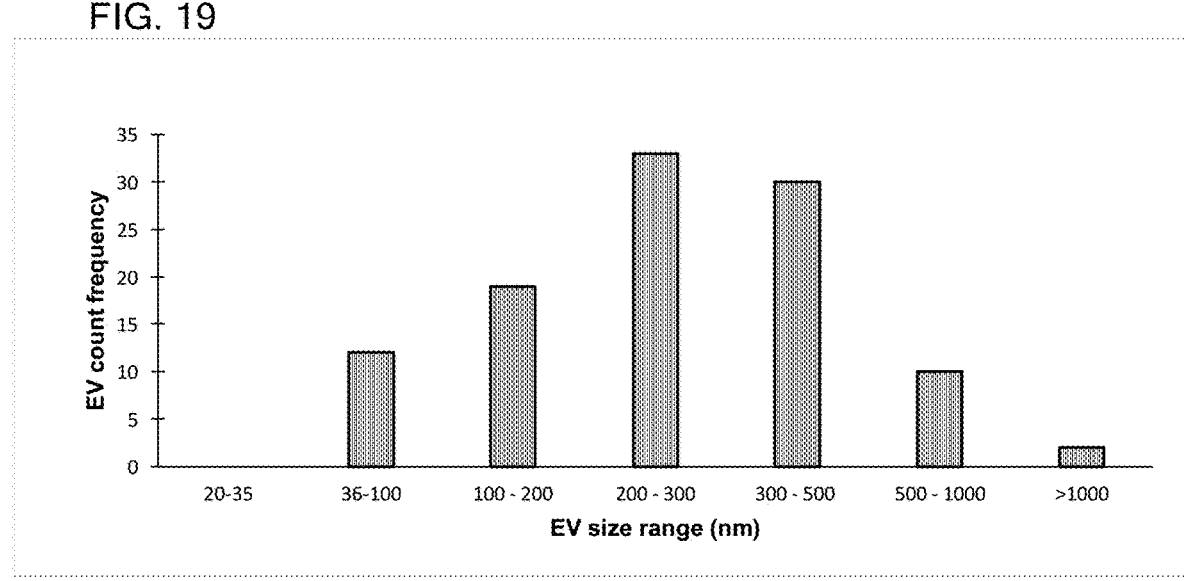
FIG. 19 shows extracellular vesicles in aqueous humor obtained from human subjects with the diagnosis of primary open angle glaucoma (POAG) are contacting each other to create an aggregate or the EVs were present as free EVs (non-aggregated). (a-b) Graphical representation of the EV population in human aqueous humor obtained from a single subject with the diagnosis of POAG. We fixed the aqueous humor with EDC fixation and imaged with transmission electron microscopy. The photographs were analyzed and EV size and number were quantitated. We observed EVs that were present within an aggregate (defined as EVs that contact each other) or a free EVs (EVs that do not contact each other). The data shows that a population of EVs that are free from contact with each other (non-aggregated EVs). There was a substantial number of EVs between 100-500 nm, and some that are larger in size.
Figure 20:
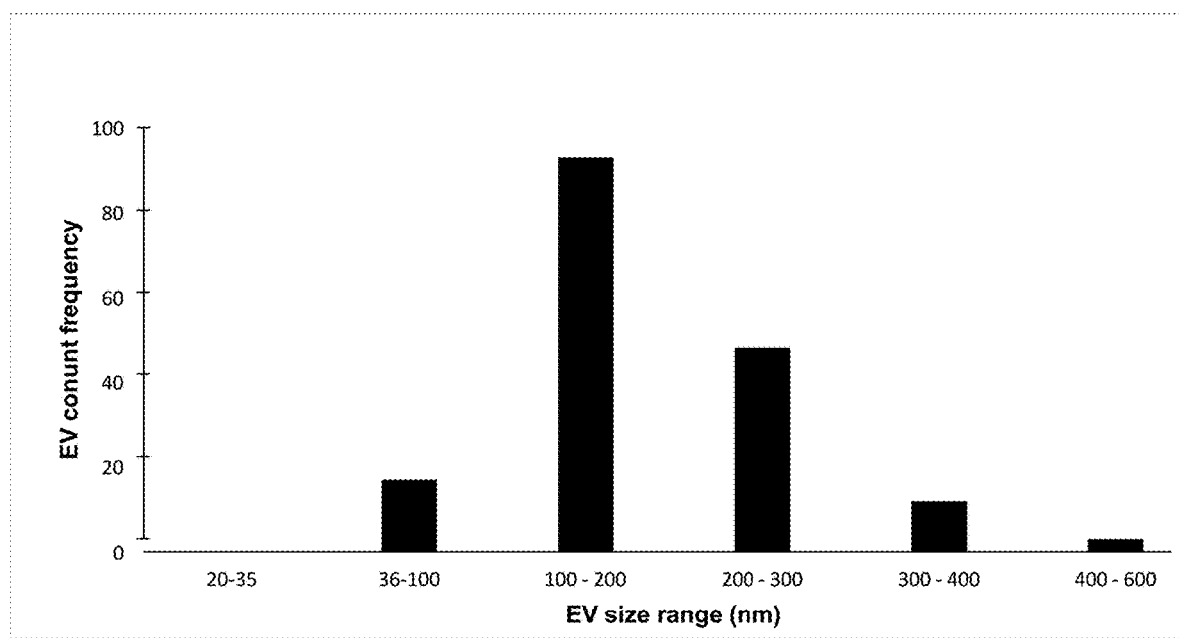
FIG. 20 shows a graph representing the size and frequency of EVs that are contacting other EVs and were located within a "glaucoma-associated-EV-aggregate" for the patient of FIG. 19. A substantial amount of the EVs were between 36 nm and 300 nm, with a few larger free EVs observed.
Figure 21:
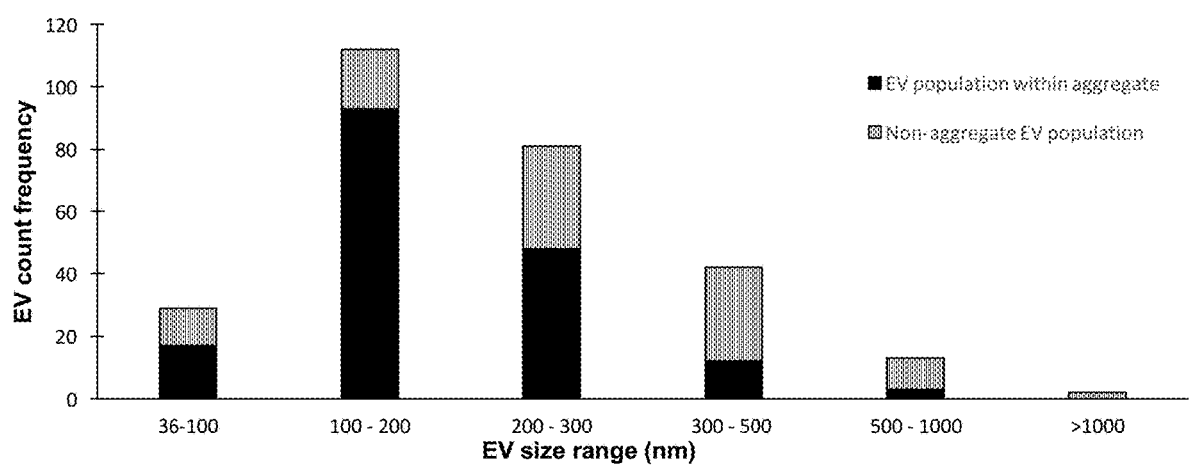
FIG. 21 shows extracellular vesicles in the aqueous humor of a single subject with the diagnosis of POAG are located within the "glaucoma-associated-EV-aggregates," with a substantial population of EVs present within the glaucoma-associated-EV-aggregate. (a) Graphical representation of the EV population in human aqueous humor obtained from a single subject with the diagnosis of POAG. We fixed the aqueous humor with EDC fixation and imaged with transmission electron microscopy. The photographs were analyzed and EV size and number were quantitated. We observed EVs that were present within an aggregate (defined as EVs that contact each other) or a free EVs (EVs that do not contact each other). The data show the number and size of individual EVs present within the glaucoma-associated-EV-aggregate (black bar) or the number and size of EVs that are not aggregated (free EVs, black and white stripe bar), as a function of the total number EVs counted. A substantial number of EVs were located within the glaucoma-associated-EV-aggregate. A substantial number of EVs within the aggregate, show a diameter from 100-300 nm in size. The larger EVs had higher populations show a substantial number of free EVs (non-aggregate EVs) in the larger size range.
Figure 22:
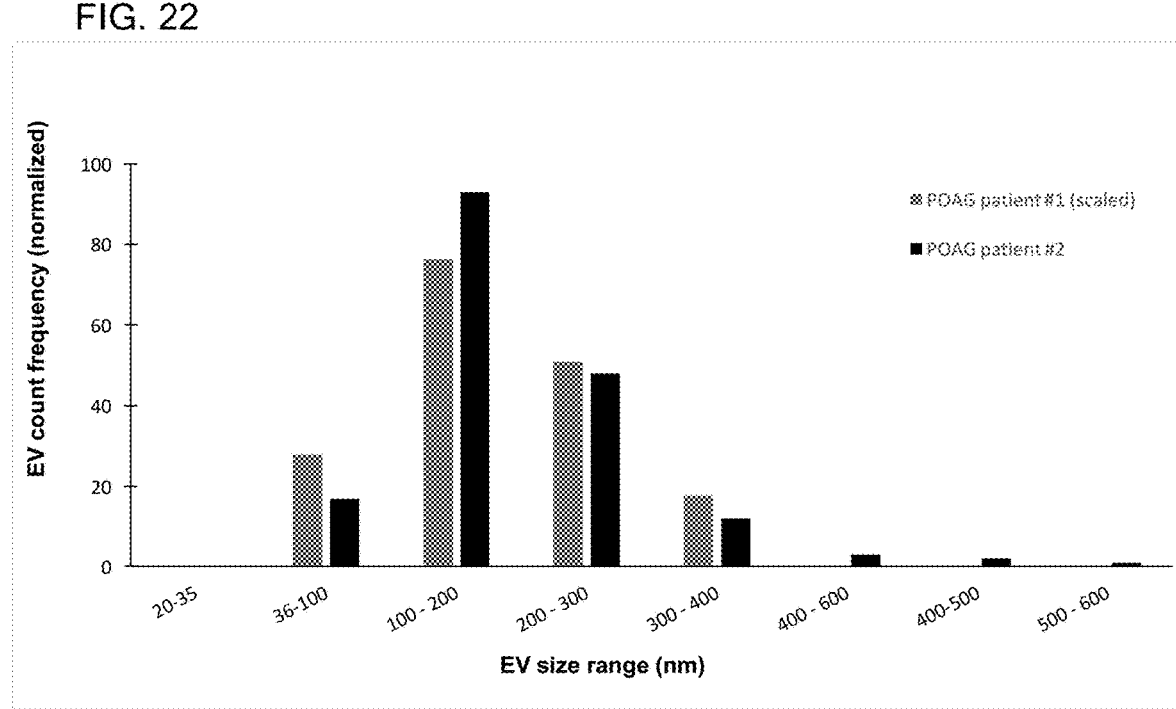
FIG. 22 shows extracellular vesicles in two separate glaucoma patient shows similar sizes and number of EVs that are located within the "glaucoma-associated-EV-aggregate." (a) Graphical representation of the EV population in human aqueous humor obtained from two subjects with the diagnosis of POAG. We fixed the aqueous humor of each subject with EDC and imaged with the specimen with transmission electron microscopy. The photographs were analyzed and EV size and number were quantitated. We observed EVs that were present within an aggregate (defined as EVs that contact each other). The data show the size and number of EVs present within the glaucoma-associated-EV-aggregate from Subject #1 (grey bar) or Subject #2 (black bar). The data was normalized and shows that both samples have a similar distribution of EVs present within the glaucoma-associated-EV-aggregate.

Extracellular vesicles in the aqueous humor of subjects with the diagnosis of POAG are located within the glaucoma-associated-EV-aggregates are similar in size to "Free-EVs" found in healthy controls. To study the EV population in the aqueous humor of human subject #1 who has a diagnosis of POAG, we obtained the aqueous humor, fixed the sample with EDC, negatively stained the specimen and imaged with TEM. We analyzed the photographs and measured the EV size and count frequency of those EVs located within the glaucoma-associated-EV-aggregate or we counted the free EVs. In POAG specimen #1, we did not observe "free-EVs." We then counted and measured the number and size of EVs that were located in the glaucoma-associated-EV-aggregate (FIG. 18). The data shows that a substantial number of EVs located within the glaucoma-associated-EV-aggregate measure in size between 36 nm and 300 nm in size with a peak number of EVs measuring 100-200 nm in size (FIG. 18). In a second human subject with the diagnosis of POAG, we again found that the POAG aqueous humor has several glaucoma-associated-EV-aggregates. We observed EVs that were present within an aggregate (defined as EVs that contact each other) or as free EVs (EVs that do not contact each other, FIG. 19-20). Furthermore, we found that a substantial number of EVs located within the glaucoma-associated-EV-aggregate were 36-300 nm in size (FIG. 21). Next we compared the number and size of EVs that were present in the glaucoma-associated-EV-aggregate and the two sample EV populations were similar (FIG. 22). These data suggest that the EV size population in patients with POAG are located within the glaucoma-associated-EV-aggregate and the data is consistent between samples.

Example 14

Figure 23:
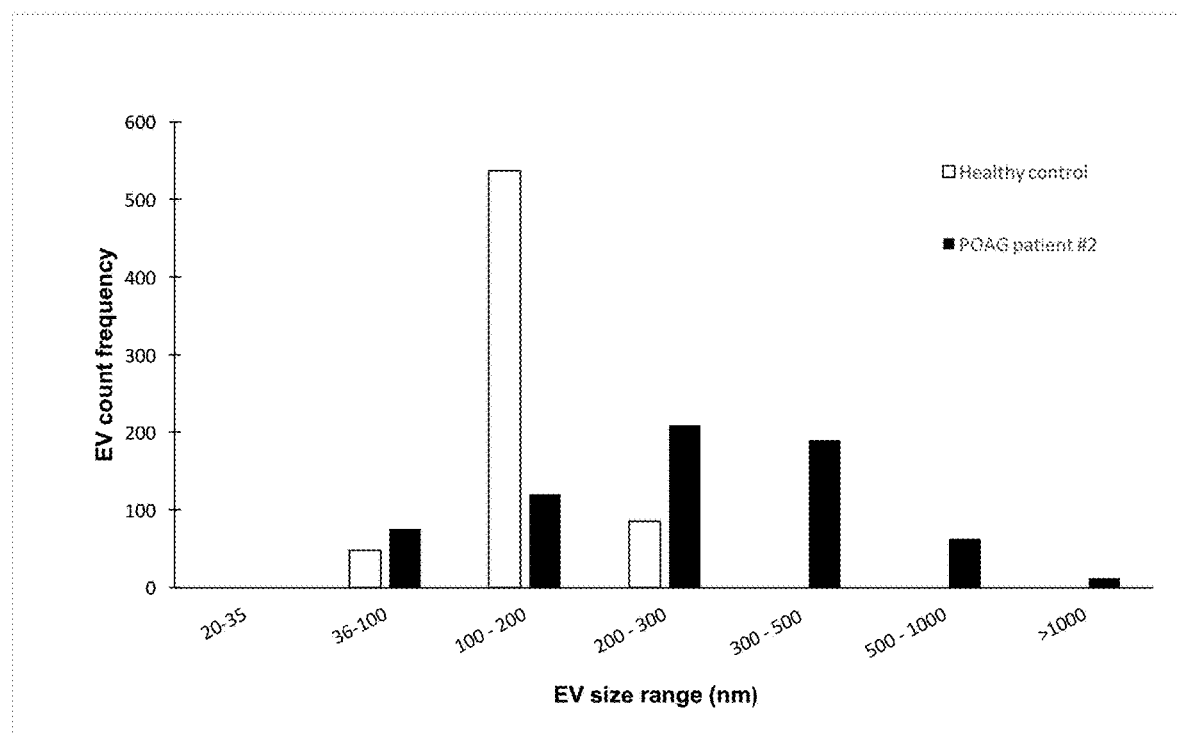
FIG. 23 shows extracellular vesicles in the aqueous humor of human subjects with the diagnosis of POAG differ in size and frequency, when compared to aqueous humor of healthy control subjects. (a) Graphical representation of the EV population in human aqueous humor obtained from a subject with the diagnosis of POAG and normal healthy control. We fixed the aqueous humor of each subject with EDC and imaged with the specimen with transmission electron microscopy. The photographs were analyzed and EV size and number were quantitated. We observed EVs that were free (non-aggregate, defined as EVs that do not contact each other) were different is size and frequency when compared to healthy controls. The data show the size and number of free EVs from healthy controls (white bar) or POAG from Subject #2 (black bar). We observed that free EVs present in patient #2's aqueous humor has substantially larger EVs, when compared to healthy controls.

Free-EVs in the aqueous humor of human subjects with the diagnosis of POAG differ in size and frequency, when compared to aqueous humor of healthy control subjects. To determine if there is a difference in free EVs in the aqueous humor of patients with glaucoma and healthy controls, we compared the size and count frequency of glaucoma and control conditions. We found that the EVs differ in size and frequency between POAG patients and healthy controls (FIG. 23). These data suggest that the EVs that do not contact other EVs are larger in POAG patients, relative to the healthy controls. These data may have implications for the function of the free EVs.

Example 15

Figure 24:
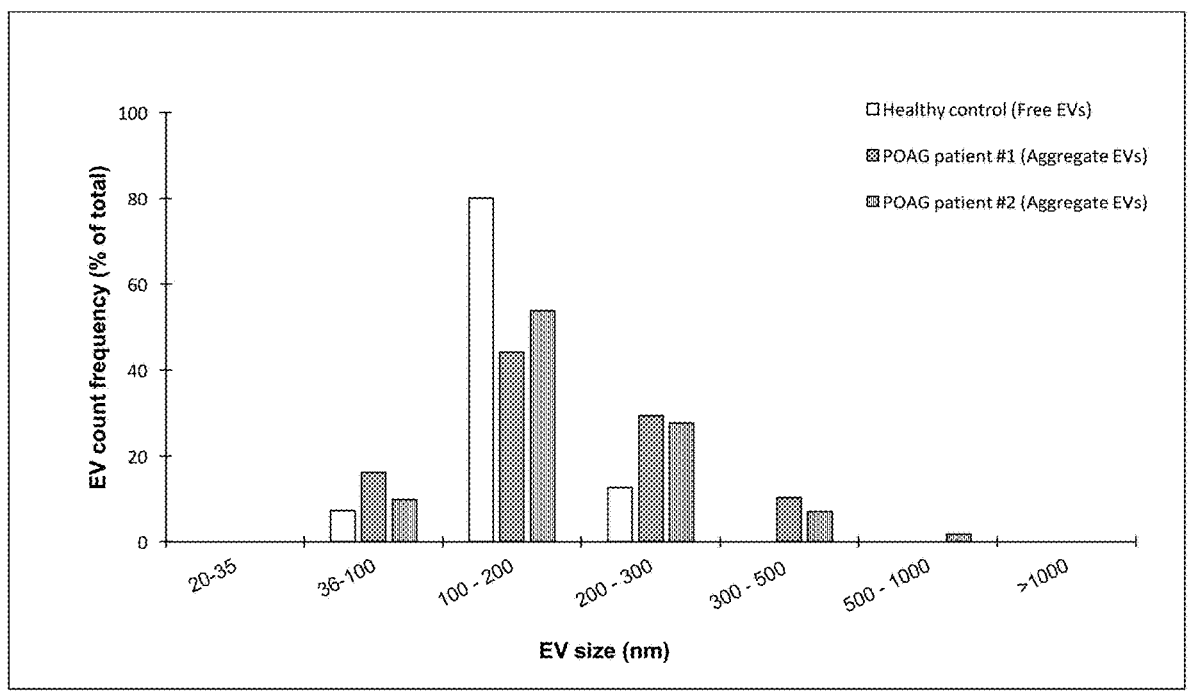
FIG. 24 shows extracellular vesicles POAG aggregates are similar in size and frequency to healthy human subjects. (a) Graphical representation of the EV population from human subject's aqueous humor obtained from healthy controls (free EVs) or POAG subjects (aggregated EVs). We fixed the aqueous humor of each subject with EDC and imaged with the specimen with transmission electron microscopy. The photographs were analyzed and EV size and number were quantitated. We observed that free-EVs (non-aggregate, defined as EVs that do not contact each other) were similar in size and frequency when compared to EVs located within the aggregates of two separate POAG subjects. The data show the size and number of free EVs from healthy controls (white bar), aggregate-EVs from POAG Subject #1 (grey bar), aggregate-EVs from POAG Subject #2 (stripe bar).

Extracellular vesicles from POAG aqueous humor that are present with the glaucoma-associated-EV-aggregates are similar in size and frequency too free EVs obtained from healthy human subjects. We hypothesized that the EVs present in the glaucoma-associated-EV-aggregate are similar in size and count frequency to the healthy control EVs. To test this, we compared the count frequency and size of EVs from POAG and healthy control specimens. The EVs from POAG aqueous humor located within the glaucoma-associated-EV-aggregate are similar in size and frequency to the non-aggregated EVs in healthy human subjects (FIG. 24). These data suggest that the normal population of EVs from healthy controls may be blocked from functioning due to the EVs in POAG being caught in the glaucoma-associated-EV-aggregates.

What is claimed is:

1. A composition, consisting of extracellular vesicle aggregate complexes isolated from a glaucoma ocular humor, wherein the extracellular vesicle aggregate complexes are present in native glaucoma ocular humor, and wherein the extracellular aggregate complexes have at least 10 extracellular vesicles.

2. The composition of claim 1, wherein the composition is isolated from animal or clinical sources.

3. The composition of claim 1, wherein the extracellular vesicle aggregate complexes comprise one or more of exomeres, exosomes, multivesicular bodies, intraluminal vesicles (ILVs), multivesicular endosomes (MVEs), oncosomes, micro-vesicles, apoptotic bodies, or vesicles originating from endosome or plasma membranes.

4. The composition of claim 1, wherein the extracellular vesicle aggregate complexes have a size from 1,000 nm to 15,000 nm.

5. The composition of claim 1, wherein the extracellular vesicle aggregate complexes have a size from 2,000 nm to 10,000 nm.

6. The composition of claim 1, wherein the extracellular vesicle aggregate complexes have a size from 2,000 nm to 5,000 nm.

7. The composition of claim 1, wherein the extracellular vesicle aggregate complexes have a size from 360 nm to 3,000 nm.

8. The composition of claim 1, wherein the extracellular vesicle aggregate complexes have a size from 360 nm to 1,000 nm.

9. The composition of claim 1, wherein at least 50% of the extracellular vesicle aggregate complexes have a diameter from 360 to 21,000 nanometers.

* * * * *